(12) United States Patent
Bur et al.

(10) Patent No.: US 8,674,111 B2
(45) Date of Patent: Mar. 18, 2014

(54) OXAZOLE AND THIAZOLE DERIVATIVES AS ALX RECEPTOR AGONISTS

(75) Inventors: Daniel Bur, Allschwil (CH); Olivier Corminboeuf, Allschwil (CH); Sylvaine Cren, Allschwil (CH); Corinna Grisostomi, Allschwil (CH); Xavier Leroy, Allschwil (CH); Sylvia Richard-Bildstein, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 13/377,793

(22) PCT Filed: Jun. 11, 2010

(86) PCT No.: PCT/IB2010/052601
§ 371 (c)(1),
(2), (4) Date: Dec. 12, 2011

(87) PCT Pub. No.: WO2010/143158
PCT Pub. Date: Dec. 16, 2010

(65) Prior Publication Data
US 2012/0115916 A1    May 10, 2012

(30) Foreign Application Priority Data
Jun. 12, 2009    (WO) .................. PCT/IB2009/052526

(51) Int. Cl.
| A61K 31/421 | (2006.01) |
| A61K 31/422 | (2006.01) |
| A61K 31/426 | (2006.01) |
| A61K 31/427 | (2006.01) |
| C07D 263/48 | (2006.01) |
| C07D 277/46 | (2006.01) |
| C07D 413/06 | (2006.01) |
| C07D 417/06 | (2006.01) |

(52) U.S. Cl.
USPC ........... 548/195; 548/196; 548/200; 548/233; 514/371; 514/377

(58) Field of Classification Search
USPC .................. 548/195, 196, 200, 233
See application file for complete search history.

(56) References Cited

U.S. PATENT DOCUMENTS

| 3,290,326 A * | 12/1966 | Hoffer ............. 548/233 |
| 2004/0043904 A1 | 3/2004 | Yamaguchi et al. |
| 2010/0331378 A1 | 12/2010 | Bur et al. |
| 2011/0034516 A1 | 2/2011 | Bur et al. |
| 2012/0101138 A1 | 4/2012 | Bur et al. |
| 2012/0115841 A1 | 5/2012 | Bur et al. |

FOREIGN PATENT DOCUMENTS

| JP | 62-234018 | 10/1987 |
| WO | WO 03/082314 | 10/2003 |
| WO | WO 2005/047899 | 5/2005 |
| WO | WO 2007/055941 | 5/2007 |
| WO | WO 2009/025793 | 2/2009 |
| WO | WO 2009/077954 | 6/2009 |
| WO | WO 2009/077990 | 6/2009 |
| WO | WO 2010/134014 | 11/2010 |
| WO | WO 2010/143116 | 12/2010 |

OTHER PUBLICATIONS

Thompson et al., Current Medicinal Chemistry, Oct. 2002, 9(19), pp. 1751-1762.*
Brown, Neurology, Jun. 25, 2002, 58(12), pp. 1720-1725.*
Burli, R. W. et al.; "Potent hFPRL1 (ALXR) agonists as potential anti-inflammatory agents;" Bioorganic & Medicinal Chemistry Letters, Pergamon, Elsevier Science, GB LNKD-DOI: 10.1016/J.BMCL; vol. 16, No. 15, pp. 3713-3718; XP025106261; ISSN: 0960-894X; Jul. 15, 2006.
Chiang, Nan et al.; "The Lipoxing Receptor ALX: Potent Ligand-Specific and Stereoselective Actions in Vivo"; Pharmacological Reviews, vol. 58, No. 3, pp. 463-487; 2006.
Gould, Philip L.; "Salt selection for basic drugs"; International Journal of Pharmaceutics, vol. 33, pp. 201-217; 1986.
Greene, Theodora W. et al.; "Protective Groups in Organic Synthesis"; Wiley-Interscience Publication; Third Edition; 1999; ISBN 0-471-22057-4, Chapter 7, pp. 494-653.
Xinglong Jiang et al., "A Practical Synthesis of a Chiral Analogue of FTY720" Org. Process Res. Dev., 2008, 12 (6), pp. 1164-1169.
Le, Yingying et al.; "Biologically Active Peptides Interacting with the G Protein-Coupled Formylpeptide Receptors"; Protein & Peptide Letters, vol. 14, pp. 846-853; 2007.
Mallamo et al., "Antiandrogenic Steroidal Sulfonyl Heterocyles. Utility of Electrostatic Complementarity in Defining Bioisosteric Sulfonyl Heterocycles"; Journal of Medicinal Chemistry, vol. 35, No. 10, 1992, pp. 1663-1670.
Obushak, N. D. et al.; "Heterocyclic syntheses on the basis of arylation products of unsaturated compounds: X.3-Aryl-2-chloropropanals as reagents for the synthesis of 2-amino-1,3-thiazole derivatives;" Russian Journal of Organic Chemistry, Consultants Bureau, US LNKD-DOI: 10.123/B:RUJO.0000034976.75646.85, vol. 40, No. 3, pp. 383-389; XP009097222; ISSN: 1070-4280; Jan. 1, 2004.
Remington; "Pharmaceutical Manufacturing"; The Science and Practice of Pharmacy, 21$^{st}$ Edition, Part 5; published by Lippincott Williams & Wilkins; 2005, Content pages only.

(Continued)

Primary Examiner — Laura L. Stockton
(74) Attorney, Agent, or Firm — Hunton & Williams LLP

(57) ABSTRACT

The invention relates to oxazole and thiazole derivatives of formula (I), wherein A, E, X, $R^1$ and $R^2$ are as defined in the description, their preparation and their use as pharmaceutically active compounds.

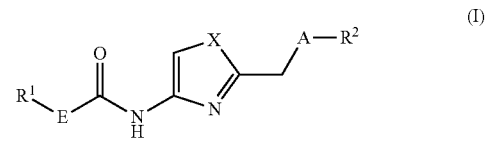

(I)

13 Claims, No Drawings

(56) References Cited

OTHER PUBLICATIONS

Schwab, Jan M. et al; "Lipoxins and new lipid mediators in the resolution of inflammation"; Current Opinion in Pharmacology, vol. 6, pp. 414-420; 2006.

Takuo Hama and John F. Hartwig "Palladium-Catalyzed a-Arylation of Esters with Chloroaranes" Org. Lett.; 2008, 10(8), pp. 1549-1552.

Yazawa, Hiroshi et al.; "βAmyloid peptide (Aβ$_{42}$) is internalized via the G-Protein-Coupled receptor FPRL1 and forms fibrillar aggregates in macrophages[1]"1 FASEB Journal, vol. 15, pp. 2454-2462; Nov. 2001.

Ying, Guoguang et al.; "Humanin, a Newly Identified Neuroprotective Factor, Uses the G Protein-Coupled Formylpeptide Receptor-Like-1 as a Functional Receptor"; Journal of Immunology, vol. 172, pp. 7078-7085; 2004.

Wermuth, C. G.; "Molecular variations based on isosteric replacements"; Practice of Medicinal Chemistry, pp. 203-237; XP002190259; Jan. 1, 1996.

Takuo Hama and John F. Hartwig "Palladium-Catalyzed a-Arylation of Esters with Chloroaranes" Org. Lett.; 2008, 10(8), pp. 1545-1548.

Sodin-Semrl et al, "Lipoxin A$_4$ counteracts Synergistic Activation of Human Fibroblast-like Synoviocytes" *Int J Immunopathol Pharmacol* (2004) 17:15-25.

Zhang et al., "BML-111, a lipoxin receptor agonist, modulates the immune response and reduces the severity of collagen-induced arthritis" (2008) *Inflamm Res* 57:157-162.

Jin et al., (2007) "Posttreatment with Aspiring-Triggered Lipoxin A$_4$ Analog Attenuates Lipopolysaccharide-Induced Acute Lung Injury in Mice: The Role of Heme Oxygenase-1" *Anesth Analg* 104:369-377.

Celik et al., Lipoxin A$_4$ in asthma: relation with disease severity and aspiring sensitivity (2007) *Clin Exp Allergy* 37:1494-1501.

Planaguma et al, Airway Lipoxin A$_4$ Generation and Lipoxin A$_4$ Receptor Expression Are Decreased in Severe Asthma (2008) *Am J Respir Crit Care Med* 178:574-582).

Levy et al., "Multi-pronged Inhibition of airway hyper-responsiveness and inflammation by Lipoxin A$_4$" (2002) *Nat Med* 8:1018-1023.

Levy et al., "Lipoxin A$_4$ stable analogs reduce allergic airway responses via mechanisms distinct from CysLT1 receptor antagonism" (2007) *FASEB J* 21:3877-3884).

Karp et al., "Defective lipoxin-mediated anti-inflammatory activity in the cystic fibrosis airway" (2004) *Nat Immunol* 5:388-392.

Gronert, "Lipoxins in the eye and their role in wound healing" (2005) *Prostaglandins Leukot Essent Fatty Acids* 73:221-229.

Gronert et al., "A Role for the Mouse 12/15-Lipoxygenase Pathaway in Promoting Epithelial Wound Healing and Host Defense" (2005) *J Biol Chem* 280:15267-15278.

Gewirtz et al., "Mechanisms of Active Intestinal Inflamation and Potential Down-regulation via Lipoxins" (2002) *Eicosanoids and other Bioactive Lipids in Cancer, Inflammation, and Radiation Injury*, Kluwer Academic/Plenum Publishers, 229-236).

Mamiya et al., "[Gly[14]]-Humanin improved the learning and memory impairment induced by scopolamine in vivo" (2001) *Br J Pharmacol* 134:1597-1599.

Miao et al., "S14G-Humanin ameliorates Aβ25-35-induced behavioral deficits by reducing neuroinflammatory responses and apoptosis in mice" (2008) *Neuropeptides* 42:557-567.

\* cited by examiner

OXAZOLE AND THIAZOLE DERIVATIVES AS ALX RECEPTOR AGONISTS

This application is the national phase application of PCT/IB2010/052601, filed Jun. 11, 2010, which claims the benefit of PCT/IB2009/052526, filed Jun. 12, 2009.

FIELD OF THE INVENTION

The present invention relates to novel oxazole and thiazole derivatives of formula (I) and their use as pharmaceuticals. The invention also concerns related aspects including processes for the preparation of the compounds, pharmaceutical compositions containing one or more compounds of formula (I), and especially their use as ALX receptor agonists.

BACKGROUND OF THE INVENTION

ALXR (alias Lipoxin A4 Receptor, FPRL1, FPR2; disclosed in WO2003/082314 as nucleotide sequence SEQ ID NO:1 and amino acid sequence SEQ ID NO:2) is a member of the G-protein coupled receptor family. ALXR was found to mediate calcium mobilisation in response to high concentration of the formyl-methionine-leucyl-phenylalanine peptide. Furthermore, a lipid metabolite, lipoxin A4 (LXA4), and its analogs, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Schwab and Serhan, Current Opinion in Pharmacology, 2006, 414-420). ALXR was also identified as a functional receptor of a various number of peptides, including a fragment of the prion protein, a peptide derived from gp120 of the Human Immunodeficiency Virus (HIV)-1$_{LAI}$ strain, and amyloid-beta 1-42 (Ab42) (for review, Le et al., Protein Pept Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signalling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. It was also reported that humanin (HN), a peptide with neuroprotective capabilities, shares the human ALXR with Ab42 on mononuclear phagocytes and neuronal cell lines and it has been suggested that the neuroprotective activity of HN may be attributed to its competitive occupation of ALXR (Ying et al., J. Immunol., 2004, 172, 7078-7085).

BRIEF SUMMARY OF THE INVENTION

The biological properties of ALXR agonists include, but are not limited to, monocyte/macrophage/microglia/dendritic cell migration/activation, neutrophil migration/activation, regulation of lymphocyte activation, proliferation and differentiation, regulation of inflammation, regulation of cytokine production and/or release, regulation of proinflammatory mediator production and/or release, regulation of immune reaction.

The present invention provides oxazole and thiazole derivatives, which are non-peptide agonists of human ALX receptor. The compounds are useful for the prevention or treatment of diseases, which respond to the modulation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

Aminopyrazole- and aminotriazole-derivatives as ALX receptor agonists are disclosed in WO2009/077954 and WO2009/077990, respectively.

Various embodiments of the invention are presented hereafter:

DETAILED DESCRIPTION OF PREFERRED EMBODIMENTS

1) The present invention relates to oxazole and thiazole derivatives of the formula (I),

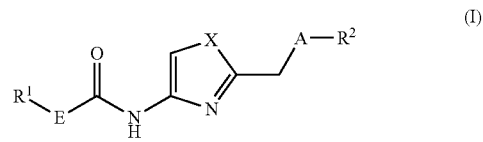

wherein
A represents a phenyl- or a heterocyclyl-group, wherein the two attachment-points of said groups are in a 1,3-arrangement; or A represents propan-1,3-diyl;
E represents *—($C_1$-$C_4$)alkyl-O—, —CH=CH— or

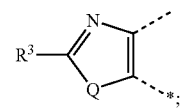

wherein the asterisks indicate the bond which is linked to $R^1$;
Q represents O or S;
$R^3$ represents hydrogen, ($C_1$-$C_4$)alkyl or cyclopropyl;
$R^1$ represents an aryl-group, which group is unsubstituted, mono- or di-substituted, wherein the substituents are independently selected from the group consisting of halogen, ($C_1$-$C_4$)alkyl, ($C_1$-$C_4$)alkoxy, ($C_1$-$C_4$)fluoroalkyl, ($C_1$-$C_4$)fluoroalkoxy and di-[($C_1$-$C_3$)alkyl]-amino;
$R^2$ represents halogen, —CO—($C_1$-$C_3$)alkyl, —$CF_2$—($C_1$-$C_3$)alkyl or —$SO_2$—($C_1$-$C_3$)alkyl (notably —CO—($C_1$-$C_3$) alkyl or —$CF_2$—($C_1$-$C_3$)alkyl); and X represents O or S;
and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

In case E represents —CH═CH— the double bond may be present in (Z)- or (E)-configuration, preferably it is present in (E)-configuration.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to four carbon atoms. The term "$(C_x-C_y)$alkyl" (x and y each being an integer), refers to an alkyl group as defined before containing x to y carbon atoms. For example a $(C_1-C_4)$alkyl group contains from one to four carbon atoms. Representative examples of alkyl groups include methyl, ethyl, n-propyl, iso-propyl, n-butyl, iso-butyl, sec-butyl and tert-butyl.

In case "$R^3$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred are methyl and ethyl, and most preferred is methyl.

In case a $(C_1-C_4)$alkyl group is a substituent to an aryl-group, the term "$(C_1-C_4)$alkyl" means $(C_1-C_4)$alkyl groups as defined above. Examples of said groups are methyl, ethyl, n-propyl, iso-propyl, n-butyl, iso-butyl, sec-butyl and tert-butyl. Preferred are methyl and ethyl, and most preferred is methyl.

In case "$R^2$" represents —CO—$(C_1-C_3)$alkyl, —$CF_2$—$(C_1-C_3)$alkyl or —$SO_2$—$(C_1-C_3)$alkyl, the term "$(C_1-C_3)$alkyl" means $(C_1-C_3)$alkyl groups as defined above. Examples of said groups are methyl, ethyl, n-propyl and iso-propyl. Preferred are methyl and ethyl, and most preferred is methyl.

In a bridging $(C_1-C_4)$alkyl group as used in E representing *—$(C_1-C_4)$alkyl-O—, the oxygen atom and the rest $R^1$ are preferably attached to the same carbon atom of the bridging $(C_1-C_4)$alkyl group. Examples of such bridging $(C_1-C_4)$alkyl groups are methylene and ethylene; preferred is a methylene group.

The term "alkoxy", used alone or in combination, refers to an alkyl-O— group wherein the alkyl group is as defined before. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. Preferred are ethoxy and methoxy. Most preferred is methoxy.

The term "fluoroalkyl" refers to an alkyl group as defined before containing one to four carbon atoms in which one or more (and possibly all) hydrogen atoms have been replaced with fluorine. The term "$(C_x-C_y)$fluoroalkyl" (x and y each being an integer) refers to a fluoroalkyl group as defined before containing x to y carbon atoms. For example a $(C_1-C_4)$fluoroalkyl group contains from one to four carbon atoms in which one to nine hydrogen atoms have been replaced with fluorine. Representative examples of fluoroalkyl groups include difluoromethyl, trifluoromethyl and 2,2,2-trifluoroethyl. Preferred is $(C_1)$fluoroalkyl such as trifluoromethyl and difluoromethyl. Most preferred is trifluoromethyl.

The term "fluoroalkoxy" refers to an alkoxy group as defined before containing one to four carbon atoms in which one or more (and possibly all) hydrogen atoms have been replaced with fluorine. The term "$(C_x-C_y)$fluoroalkoxy" (x and y each being an integer) refers to a fluoroalkoxy group as defined before containing x to y carbon atoms. For example a $(C_1-C_4)$fluoroalkoxy group contains from one to four carbon atoms in which one to nine hydrogen atoms have been replaced with fluorine. Representative examples of fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy. Most preferred is trifluoromethoxy.

The term "di-[$(C_1-C_3)$alkyl]-amino" refers to an amino group which is substituted by two $(C_1-C_3)$alkyl groups as defined above, wherein the two $(C_1-C_3)$alkyl groups may be the same or different. Representative examples of di-[$(C_1-C_3)$alkyl]-amino groups include, but are not limited to dimethylamino, methyl-ethyl-amino and diethylamino. Preferred is dimethylamino.

The term halogen means fluoro, chloro, bromo or iodo.

In case an aryl-group is substituted with halogen, the term "halogen" means fluoro, chloro, bromo or iodo, preferably fluoro, chloro or bromo and most preferably fluoro or chloro.

In case "$R^2$" represents halogen, the term "halogen" means fluoro, chloro, bromo or iodo, preferably chloro or bromo and most preferably bromo.

The term "aryl", used alone or in any combination, means phenyl (preferred) or naphthyl. The aryl group is unsubstituted, mono- or di-substituted (notably unsubstituted or mono-substituted), wherein the substituents are independently selected from the group consisting of halogen, $(C_1-C_4)$alkyl, $(C_1-C_4)$alkoxy, $(C_1-C_4)$fluoroalkyl, $(C_1-C_4)$fluoroalkoxy and di-[$(C_1-C_3)$alkyl]-amino and preferably from halogen, $(C_1-C_4)$alkyl, $(C_1-C_4)$alkoxy, $(C_1-C_4)$fluoroalkyl and $(C_1-C_4)$fluoroalkoxy.

Examples are phenyl, 2-chlorophenyl, 3-chlorophenyl, 2-chloro-4-fluorophenyl, 3-fluorophenyl, 4-fluorophenyl, 3-methylphenyl, 3-methoxyphenyl, 4-trifluoromethylphenyl, and 3-trifluoromethoxyphenyl. Preferred examples are phenyl, 2-chlorophenyl, 2-chloro-4-fluorophenyl, 3-methylphenyl and 3-methoxyphenyl.

The term "heterocyclyl", used alone or in combination, means a 5- or 6-membered (notably 5-membered) monocyclic aromatic ring containing 1, 2 or 3 (notably 1 or 2) heteroatoms independently selected from oxygen, nitrogen and sulfur. Examples of 5-membered heterocyclyl groups are furanyl, oxazolyl, isoxazolyl, oxadiazolyl, thienyl, thiazolyl, isothiazolyl, thiadiazolyl, pyrrolyl, imidazolyl, pyrazolyl and triazolyl. Examples of 6-membered heterocyclyl groups are pyridyl, pyrimidyl, pyridazinyl, and pyrazinyl. Preferred examples of heterocyclyl groups are oxazolyl, thienyl, thiazolyl and pyrazolyl. More preferred examples are thienyl, thiazolyl and pyrazolyl. Most preferred examples are thienyl and pyrazolyl.

In case A represents furan-2,5-diyl, the residue $R^2$ is preferably attached in 5-position.

In case A represents thiophen-2,5-diyl, the residue $R^2$ is preferably attached in 5-position.

In case A represents pyrazol-1,3-diyl, the residue $R^2$ is preferably attached in 3-position.

In case A represents pyrazol-1,4-diyl, the residue $R^2$ is preferably attached in 4-position.

The term "1,3-arrangement" as used in the specification of "A" means that the two atoms of the phenyl or heterocyclyl group which are attached to the oxazole-methyl moiety (or thiazole-methyl moiety) and to the residue $R^2$ respectively are separated from each other by one atom; for example, if "A" represents phenyl the arrangement of the substituents is as shown in the FIGURE below

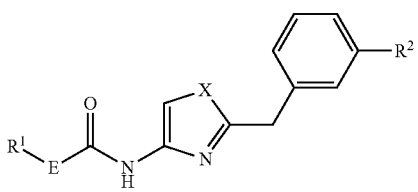

In this patent application, a dotted line shows the point of attachment of the radical drawn. For example, the radical drawn below

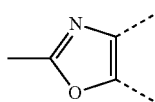

is the 2-methyl-oxazole-4,5-diyl group.

2) A further embodiment of the invention relates to oxazole derivatives according to embodiment 1), wherein A represents a phenyl- or a heterocyclyl-group, wherein the two attachment-points of said groups are in a 1,3-arrangement; or A represents propan-1,3-diyl;

E represents *—$(C_1-C_4)$alkyl-O—, —CH=CH— or

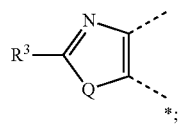

wherein the asterisks indicate the bond which is linked to $R^1$;
Q represents O or S;
$R^3$ represents hydrogen, $(C_1-C_4)$alkyl or cyclopropyl;
$R^1$ represents an aryl-group, which group is unsubstituted, mono- or di-substituted, wherein the substituents are independently selected from the group consisting of halogen, $(C_1-C_4)$alkyl, $(C_1-C_4)$alkoxy, $(C_1-C_4)$fluoroalkyl and $(C_1-C_4)$fluoroalkoxy;
$R^2$ represents halogen, —CO—$(C_1-C_3)$alkyl, —CF$_2$—$(C_1-C_3)$alkyl or —SO$_2$—$(C_1-C_3)$alkyl (notably —CO—$(C_1-C_3)$alkyl or —CF$_2$—$(C_1-C_3)$alkyl); and
X represents O;
and to the salts (in particular pharmaceutically acceptable salts) of such compounds.

3) A further embodiment of the invention relates to oxazole derivatives according to any one of embodiments 1) or 2), wherein A represents a phenyl- or a heterocyclyl-group, wherein the two attachment-points of said groups are in a 1,3-arrangement; or A represents propan-1,3-diyl;

E represents *—CH$_2$—O— or

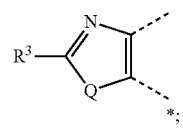

wherein the asterisks indicate the bond which is linked to $R^1$;
Q represents O or S;
$R^3$ represents hydrogen or $(C_1-C_4)$alkyl (and notably hydrogen or methyl);
$R^1$ represents an aryl-group, which group is unsubstituted, mono- or di-substituted (notably unsubstituted or mono-substituted), wherein the substituents are independently selected from the group consisting of halogen, $(C_1-C_4)$alkyl, $(C_1-C_4)$alkoxy, $(C_1-C_4)$fluoroalkyl and $(C_1-C_4)$fluoroalkoxy (and notably from halogen, $(C_1-C_4)$alkyl, $(C_1-C_4)$alkoxy and $(C_1-C_4)$fluoroalkyl);
$R^2$ represents halogen, —CO—$(C_1-C_3)$alkyl or —CF$_2$—$(C_1-C_3)$alkyl (notably —CO—$(C_1-C_3)$alkyl or —CF$_2$—$(C_1-C_3)$alkyl); and
X represents O;
and to the salts (in particular pharmaceutically acceptable salts) of such compounds.

4) A further embodiment of the invention relates to oxazole derivatives according to any one of embodiments 1) to 3), wherein A represents a thienyl- or a pyrazolyl-group, wherein the two attachment-points of said groups are in a 1,3-arrangement;

E represents *—CH$_2$—O— or

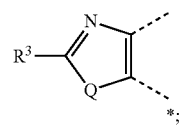

wherein the asterisks indicate the bond which is linked to $R^1$;
Q represents O or S;
$R^3$ represents hydrogen, methyl or ethyl (and notably hydrogen or methyl);
$R^1$ represents phenyl, which is unsubstituted, mono- or di-substituted (notably unsubstituted or mono-substituted), wherein the substituents are independently selected from the group consisting of halogen, $(C_1-C_4)$alkyl, $(C_1-C_4)$alkoxy and $(C_1-C_4)$fluoroalkyl (and notably from halogen and $(C_1-C_4)$alkyl);
$R^2$ represents —CO—CH$_3$ or —CF$_2$—CH$_3$; and
X represents O;
and to the salts (in particular pharmaceutically acceptable salts) of such compounds.

5) A further embodiment of the invention relates to oxazole and thiazole derivatives according to any one of embodiments 1) to 3), wherein A represents a phenyl- or a heterocyclyl-group, wherein the two attachment-points of said groups are in a 1,3-arrangement;
and to the salts (in particular pharmaceutically acceptable salts) of such compounds.

6) A further embodiment of the invention relates to oxazole and thiazole derivatives according to any one of embodiments 1) to 3) or 5), wherein A represents a phenyl-, an oxazolyl-, a thienyl-, a thiazolyl- or a pyrazolyl-group, wherein the two attachment-points of said groups are in a 1,3-arrangement;
and to the salts (in particular pharmaceutically acceptable salts) of such compounds.

7) A further embodiment of the invention relates to oxazole and thiazole derivatives according to any one of embodiments 1) to 3), 5) or 6), wherein
A represents a phenyl-group, wherein the two attachment-points of said group are in a 1,3-arrangement;
and to the salts (in particular pharmaceutically acceptable salts) of such compounds.

8) A further embodiment of the invention relates to oxazole and thiazole derivatives according to any one of embodiments 1) to 3) or 5), wherein
A represents a heterocyclyl-group, wherein the two attachment-points of said group are in a 1,3-arrangement;
and to the salts (in particular pharmaceutically acceptable salts) of such compounds.

9) A further embodiment of the invention relates to oxazole and thiazole derivatives according to any one of embodiments 1) to 6), wherein
A represents a thienyl- (notably thiophen-2,5-diyl) or a pyrazolyl-group (notably pyrazol-1,3-diyl), wherein the two attachment-points of said groups are in a 1,3-arrangement;
and to the salts (in particular pharmaceutically acceptable salts) of such compounds.

10) A further embodiment of the invention relates to oxazole and thiazole derivatives according to any one of embodiments 1) to 3), wherein
A represents propan-1,3-diyl;
and to the salts (in particular pharmaceutically acceptable salts) of such compounds.

11) A further embodiment of the invention relates to oxazole and thiazole derivatives according to any one of embodiments 1) to 10), wherein
E represents *—CH$_2$—O— or

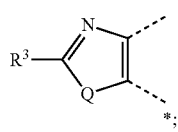

wherein the asterisks indicate the bond which is linked to R$^1$;
and to the salts (in particular pharmaceutically acceptable salts) of such compounds.

12) A further embodiment of the invention relates to oxazole and thiazole derivatives according to any one of embodiments 1) to 10), wherein
E represents *—(C$_1$-C$_4$)alkyl-O— (notably *—CH$_2$—O—), wherein the asterisk indicates the bond which is linked to R$^1$;
and to the salts (in particular pharmaceutically acceptable salts) of such compounds.

13) A further embodiment of the invention relates to oxazole and thiazole derivatives according to any one of embodiments 1), 2) or 5) to 10), wherein
E represents —CH=CH—;
and to the salts (in particular pharmaceutically acceptable salts) of such compounds.

14) A further embodiment of the invention relates to oxazole and thiazole derivatives according to any one of embodiments 1) to 10), wherein
E represents

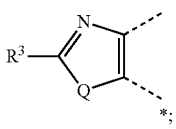

wherein the asterisk indicates the bond which is linked to R$^1$;
and to the salts (in particular pharmaceutically acceptable salts) of such compounds.

15) A further embodiment of the invention relates to oxazole and thiazole derivatives according to any one of embodiments 1) to 11) or 14), wherein
Q represents O;
and to the salts (in particular pharmaceutically acceptable salts) of such compounds.

16) A further embodiment of the invention relates to oxazole and thiazole derivatives according to any one of embodiments 1) to 11), 14) or 15), wherein
R$^3$ represents hydrogen or (C$_1$-C$_4$)alkyl (and notably hydrogen or methyl);
and to the salts (in particular pharmaceutically acceptable salts) of such compounds.

17) A further embodiment of the invention relates to oxazole and thiazole derivatives according to any one of embodiments 1) to 11), 14) or 15), wherein
R$^3$ represents hydrogen;
and to the salts (in particular pharmaceutically acceptable salts) of such compounds.

18) A further embodiment of the invention relates to oxazole and thiazole derivatives according to any one of embodiments 1) to 11), 14) or 15), wherein
R$^3$ represents (C$_1$-C$_4$)alkyl (notably methyl);
and to the salts (in particular pharmaceutically acceptable salts) of such compounds.

19) A further embodiment of the invention relates to oxazole and thiazole derivatives according to any one of embodiments 1), 2), 5) to 11), 14) or 15), wherein
R$^3$ represents cyclopropyl;
and to the salts (in particular pharmaceutically acceptable salts) of such compounds.

20) A further embodiment of the invention relates to oxazole and thiazole derivatives according to any one of embodiments 1) to 19), wherein
R$^1$ represents phenyl, which is unsubstituted, mono- or di-substituted (notably unsubstituted or mono-substituted), wherein the substituents are independently selected from the group consisting of halogen, (C$_1$-C$_4$)alkyl, (C$_1$-C$_4$)alkoxy and (C$_1$-C$_4$)fluoroalkyl (and notably from halogen and (C$_1$-C$_4$)alkyl);
and to the salts (in particular pharmaceutically acceptable salts) of such compounds.

21) A further embodiment of the invention relates to oxazole and thiazole derivatives according to any one of embodiments 1) to 19), wherein
R$^1$ represents phenyl, which is unsubstituted, mono- or di-substituted (notably unsubstituted or mono-substituted), wherein the substituents are independently selected from the group consisting of fluoro, chloro, methyl, methoxy and trifluoromethyl (and notably from fluoro, chloro and methyl);
and to the salts (in particular pharmaceutically acceptable salts) of such compounds.

22) A further embodiment of the invention relates to oxazole and thiazole derivatives according to any one of embodiments 1) to 21), wherein $R^1$ represents phenyl, which is unsubstituted, mono- or di-substituted with halogen (notably mono-substituted with chloro);
and to the salts (in particular pharmaceutically acceptable salts) of such compounds.

23) A further embodiment of the invention relates to oxazole and thiazole derivatives according to any one of embodiments 1) to 22), wherein
$R^2$ represents —CO—$(C_1$-$C_3)$alkyl or —$CF_2$—$(C_1$-$C_3)$alkyl (notably —CO—$CH_3$ or —$CF_2$—$CH_3$);
and to the salts (in particular pharmaceutically acceptable salts) of such compounds.

24) A further embodiment of the invention relates to oxazole and thiazole derivatives according to any one of embodiments 1) to 22), wherein
$R^2$ represents —CO—$(C_1$-$C_3)$alkyl (notably —CO—$CH_3$);
and to the salts (in particular pharmaceutically acceptable salts) of such compounds.

25) A further embodiment of the invention relates to oxazole and thiazole derivatives according to any one of embodiments 1) to 22), wherein
$R^2$ represents —$CF_2$—$(C_1$-$C_3)$alkyl (notably —$CF_2$—$CH_3$);
and to the salts (in particular pharmaceutically acceptable salts) of such compounds.

26) A further embodiment of the invention relates to oxazole and thiazole derivatives according to any one of embodiments 1), 2) or 5) to 22), wherein
$R^2$ represents —$SO_2$—$(C_1$-$C_3)$alkyl (notably —$SO_2$—$CH_3$);
and to the salts (in particular pharmaceutically acceptable salts) of such compounds.

27) A further embodiment of the invention relates to oxazole and thiazole derivatives according to any one of embodiments 1) to 3) or 5) to 22), wherein
$R^2$ represents halogen (notably bromo);
and to the salts (in particular pharmaceutically acceptable salts) of such compounds.

28) A further embodiment of the invention relates to oxazole derivatives according to any one of embodiments 1) to 27), wherein
X represents O;
and to the salts (in particular pharmaceutically acceptable salts) of such compounds.

29) A further embodiment of the invention relates to thiazole derivatives according to any one of embodiments 1) or 5) to 27), wherein
X represents S;
and to the salts (in particular pharmaceutically acceptable salts) of such compounds.

30) Preferred compounds of formula (I) as defined in embodiment 1) are selected from the group consisting of:
[2-(5-Oxo-hexyl)-oxazol-4-yl]-carbamic acid 2-chloro-benzyl ester;
5-Phenyl-oxazole-4-carboxylic acid [2-(5-oxo-hexyl)-oxazol-4-yl]-amide;
[2-(3-Acetyl-pyrazol-1-ylmethyl)-oxazol-4-yl]-carbamic acid 2-chloro-benzyl ester;
[2-(5,5-Difluoro-hexyl)-oxazol-4-yl]-carbamic acid 2-chloro-benzyl ester;
2-Methyl-5-m-tolyl-oxazole-4-carboxylic acid [2-(5,5-difluoro-hexyl)-oxazol-4-yl]-amide;
2-Methyl-5-m-tolyl-oxazole-4-carboxylic acid [2-(5-oxo-hexyl)-oxazol-4-yl]-amide;
5-(3-Fluoro-phenyl)-thiazole-4-carboxylic acid [2-(5-oxo-hexyl)-oxazol-4-yl]-amide;
5-(4-Fluoro-phenyl)-oxazole-4-carboxylic acid [2-(5-oxo-hexyl)-oxazol-4-yl]-amide;
2-Ethyl-5-phenyl-oxazole-4-carboxylic acid [2-(5-oxo-hexyl)-oxazol-4-yl]-amide;
[2-(4-Bromo-pyrazol-1-ylmethyl)-oxazol-4-yl]-carbamic acid 2-chloro-benzyl ester;
[2-(3-Acetyl-pyrazol-1-ylmethyl)-oxazol-4-yl]-carbamic acid 2-chloro-4-fluoro-benzyl ester;
[2-(3-Acetyl-pyrazol-1-ylmethyl)-oxazol-4-yl]-carbamic acid 3-methoxy-benzyl ester;
[2-(3-Acetyl-pyrazol-1-ylmethyl)-oxazol-4-yl]-carbamic acid 4-trifluoromethyl-benzyl ester;
[2-(5-Acetyl-thiophen-2-ylmethyl)-oxazol-4-yl]-carbamic acid 2-chloro-benzyl ester;
[2-(3-Acetyl-benzyl)-oxazol-4-yl]-carbamic acid 3-trifluoromethoxy-benzyl ester;
2-Cyclopropyl-5-phenyl-thiazole-4-carboxylic acid [2-(3-acetyl-pyrazol-1-ylmethyl)-oxazol-4-yl]-amide; and
N-[2-(3-Acetyl-benzyl)-oxazol-4-yl]-3-(4-trifluoromethyl-phenyl)-acrylamide;
wherein the double bond of acrylamide derivatives cited in the above list may be in (E)- or (Z)-configuration (preferably in (E)-configuration);
or salts (in particular pharmaceutically acceptable salts) of such compounds.

31) Further preferred compounds of formula (I) as defined in embodiment 1) are selected from the group consisting of:
5-Phenyl-oxazole-4-carboxylic acid [2-(5-acetyl-thiophen-2-ylmethyl)-thiazol-4-yl]-amide;
5-(3-Chloro-phenyl)-2-methyl-oxazole-4-carboxylic acid [2-(5-acetyl-thiophen-2-ylmethyl)-thiazol-4-yl]-amide;
5-Phenyl-oxazole-4-carboxylic acid [2-(5-acetyl-furan-2-ylmethyl)-thiazol-4-yl]-amide; and
2-Methyl-5-m-tolyl-oxazole-4-carboxylic acid [2-(5-acetyl-furan-2-ylmethyl)-thiazol-4-yl]-amide;
or salts (in particular pharmaceutically acceptable salts) of such compounds.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 31), or pharmaceutically acceptable salts thereof, are suitable for use as medicaments. In particular, compounds of formula (I) modulate the ALX receptor, i.e.

they act as ALX receptor agonists, and are useful for the prevention or treatment of diseases which respond to the activation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the modulation of immune responses (especially those elicited by vaccination). Especially, compounds of formula (I) are useful for the prevention or treatment of diseases such as inflammatory diseases, obstructive airway diseases, allergic conditions, cardiovascular disorders, neuroinflammation, neurological disorders, pain, prion-mediated diseases and amyloid-mediated disorders (especially Alzheimer's disease).

In particular, the compounds of formula (I) according to any one of embodiments 1) to 31), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.

3) Further inflammatory diseases, obstructive airway diseases and allergic conditions include bronchiectasis, and pneumoconiosis of whatever type or genesis.

4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.

5) In a further embodiment the compounds of formula (I) according to any one of embodiments 1) to 31), or pharmaceutically acceptable salts thereof, are particularly suitable for the prevention or treatment of inflammatory diseases. Inflammatory diseases include one, several or all of the following groups of diseases and disorders:

5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.

5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.

5c) Further inflammatory diseases also relate to diseases or conditions having an inflammatory component. Diseases or conditions having an inflammatory component include, but are not limited to, diseases and conditions affecting the eye such as uveitis (anterior, intermediate and posterior), Behçet syndrome uveitis, conjunctivitis, keratoconjunctivitis sicca, Sjögren syndrome keratoconjunctivitis sicca, and vernal conjunctivitis (and especially conjunctivitis, keratoconjunctivitis sicca, and vernal conjunctivitis); diseases affecting the nose including rhinitis and allergic rhinitis (and especially allergic rhinitis); and inflammatory diseases in which autoimmune reactions are implicated or which have an autoimmune component or aetiology, such as systemic lupus erythematosus, ankylosing spondylitis, Behçet syndrome, Sjögren syndrome, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine ophthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis (and especially systemic lupus erythematosus, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine ophthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis).

5d) Further inflammatory diseases in which autoimmune reactions are implicated or which have an autoimmune component or aetiology include rheumatoid arthritis, Hashimoto's thyroid and diabetes type I or II.

Further, the compounds of formula (I) according to any one of embodiments 1) to 31), or pharmaceutically acceptable salts thereof, are suitable for the prevention or treatment of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation, particularly in the treatment of acute or chronic allo- and xenograft rejection or in the transplantation of insulin producing cells, e g pancreatic islet cells.

Further, the compounds of formula (I) according to any one of embodiments 1) to 31), or pharmaceutically acceptable salts thereof, are suitable for the prevention or treatment of HIV-mediated retroviral infections.

HIV-mediated retroviral infections include, but are not limited to, one, several or all of the groups of diseases and disorders caused by HIV-1 and HIV-2 strains such as GUN-4v, GUN-7 wt, AG204, AG206, AG208, HCM305, HCM308, HCM342, mSTD104, and HCM309.

Further, the compounds of formula (I) according to any one of embodiments 1) to 31), or pharmaceutically acceptable salts thereof, are suitable for the prevention or treatment of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to any one of embodiments 1) to 31), or pharmaceutically acceptable salts thereof, are suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compounds of formula (I) according to any one of embodiments 1) to 31), or pharmaceutically acceptable salts thereof, are suitable for the prevention or treatment of neurological disorders.

In particular, neurological disorders include, but are not limited to, epilepsy, stroke, cerebral ischemia, cerebral palsy, relapsing remitting multiple sclerosis, progressive multiple sclerosis, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea (and especially epilepsy, stroke, cerebral ischemia, cerebral palsy, relapsing remitting multiple sclerosis, progressive multiple sclerosis, Alpers' disease, amyotrophic lateral sclerosis (ALS), senile dementia, dementia with Lewy bodies, Rett syndrome, spinal cord trauma, traumatic brain injury, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea).

Further, the compounds of formula (I) according to any one of embodiments 1) to 31), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to any one of embodiments 1) to 31), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Sträussler-Scheinker syndrome (GSS), Fatal Familial Insomnia (FFI) and Creutzfeldt-Jakob Disease (CJD).

Further, the compounds of formula (I) according to any one of embodiments 1) to 31), or pharmaceutically acceptable salts thereof, are suitable for the treatment of amyloid-mediated disorders. Amyloid-mediated disorders are defined as diseases and disorders that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, amyloid light chain amyloidosis, familial amyloid neuropathies, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis (and especially progressive supranuclear palsy, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis).

Further, the compounds of formula (I) according to any one of embodiments 1) to 31), or pharmaceutically acceptable salts thereof, are suitable for the modulation of immune responses. The modulation of immune responses includes, but is not limited to, methods based on the administration to a subject a composition of at least one antigen and at least one compound of formula (I) according to any one of embodiments 1) to 31), or pharmaceutically acceptable salts thereof. In some cases, the antigen-containing composition is administrated first, followed by administration of a composition of at least one compounds of formula (I) according to any one of embodiments 1) to 31), or pharmaceutically acceptable salts thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of at least one compound of formula (I) according to any one of embodiments 1) to 31), or pharmaceutically acceptable salts thereof, and the antigen, as compared to sole administration of the antigen;

2) A greater sensitivity to small amounts of antigen (e.g., toxin or pathogen) or antigens that do not habitually induce strong immune responses; and 3) More effective anti-tumor therapies.

Further, the compounds of formula (I) according to any one of embodiments 1) to 31), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, inflammatory diseases caused by pathogenic organisms.

Especially, compounds of formula (I) according to any one of embodiments 1) to 31), or pharmaceutically acceptable salts thereof, are suitable for the prevention or treatment of diseases selected from one, several or all of the following groups of diseases and disorders:

1) Inflammatory diseases, obstructive airway diseases and allergic conditions such as acute lung injury (ALI); adult/acute respiratory distress syndrome (ARDS); chronic obstructive pulmonary, airway or lung disease (COPD, COAD or COLD), including chronic bronchitis or dyspnea associated therewith; and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection;

2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;

3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);

4) HIV-mediated retroviral infections such as diseases and disorders caused by HIV-1 and HIV-2 strains such as GUN-4v, GUN-7 wt, AG204, AG206, AG208, HCM305, HCM308, HCM342, mSTD104, and HCM309;

5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid $\beta$ deposition of amyloid plaques;

6) Neurological disorders such as stroke, cerebral ischemia, Alzheimer's disease, and Parkinson's disease;

7) Prion-mediated diseases, also known as transmissible spongiform encephalopathies (TSEs), such as kuru, Gerstmann-Sträussler-Scheinker syndrome (GSS), Fatal Familial Insomnia (FFI) and Creutzfeldt-Jakob Disease (CJD);

8) Amyloid-mediated disorders;

9) Cystic fibrosis, wound healing and inflammatory diseases caused by pathogenic organisms.

The invention also relates to the use of a compound of formula (I) according to any one of embodiments 1) to 31) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 31).

A pharmaceutical composition according to the present invention contains at least one compound of formula (I) according to any one of embodiments 1) to 31) (or a pharmaceutically acceptable salt thereof) as the active agent and optionally carriers and/or diluents and/or adjuvants.

The compounds of formula (I) according to any one of embodiments 1) to 31) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 31), or a pharmaceutically acceptable salt thereof.

Any reference to a compound of formula (I) in this text is to be understood as referring also to the salts (and especially the pharmaceutically acceptable salts) of such compounds, as appropriate and expedient. The preferences indicated for the compounds of formula (I) of course apply mutatis mutandis to the salts and pharmaceutically acceptable salts of the compounds of formula (I). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups A, E, X, Q, $R^1$, $R^2$ and $R^3$ are as defined for formula (I). Other abbreviations used are defined in the experimental section. Generic groups Rx as used e.g. in structure O, Q, N, P, K, I, CC, CA and XX below represent $(C_1-C_2)$alkyl or both Rx together form an ethane-1,2-diyl bridge. Generic group $R^y$ as used e.g. in structure O, Q, N, P, K, I, CC, CA and XX below represents $(C_1-C_3)$alkyl. The generic carboxyl protecting group R as used e.g. in structure C, A, K or I, in the schemes below and in the general procedures of the experimental part represents ($C_1$-$C_4$)alkyl, preferably methyl or ethyl. The leaving group LG as used in structure CA represents a sulfonate- (notably mesylate) or a halogenide-moiety (notably chloride or bromide).

Reactions of alcohols with methanesulfonyl chloride may result in the formation of the respective chloride or the respective mesylate derivative depending on the reaction conditions used; it is well known in the art that already small changes in such reaction conditions may have an influence on the outcome of said reactions; it should be understood that normally both reagents, the chloride and the mesylate, might be useful as electrophiles in reactions discussed below.

In some instances the generic groups A, E, X, Q, $R^1$, $R^2$ and $R^3$ might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

A. Synthesis of Final Products

Sections A.a) to A.e) hereafter describe general methods for preparing compounds of formula (I).

A.a) The compounds of formula (I), wherein E is different from *—($C_1$-$C_4$)alkyl-O—, can be prepared from compounds of structure 1 or their salts by reaction with the appropriate carboxylic acid of formula $R^1$-E-COOH using standard amide coupling conditions such as EDC/HOBt/DMAP, TBTU, HBTU or PyBOP in the presence of a base such as DIPEA or $Et_3N$ at a temperature about rt in a suitable solvent such as $CH_2Cl_2$.

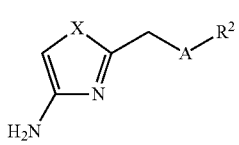

Structure 1

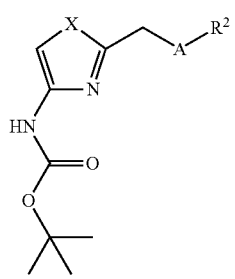

Structure G

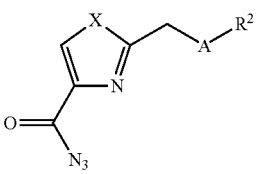

Structure F

A.b) Alternatively, the compounds of formula (I) can be prepared from compounds of structure G by the following sequence: a) deprotonation with a base such as NaH at a temperature about 0° C. in a suitable solvent such as THF followed by reaction with the appropriate carboxylic acid chloride of formula $R^1$-E-COCl at a temperature ranging from 0° C. to rt in a suitable solvent such as THF. If not commercially available, the appropriate carboxylic acid chloride can be prepared at a temperature about rt from the corresponding carboxylic acid by reaction with a reagent such as oxalyl chloride in presence of DMF in a suitable solvent such as toluene; and b) Boc deprotection under anhydrous conditions at a temperature about rt with an acid such as trifluoroacetic acid in a suitable solvent such as $CH_2Cl_2$.

A.c) In case E represents *—($C_1$-$C_4$)alkyl-O—, the compounds of formula (I) may be prepared from compounds of structure F by Curtius rearrangement at a temperature about 140° C. in a suitable solvent such as xylene followed by reaction with the corresponding alcohol of formula $R^1$-E-H at a temperature about 140° C. in a suitable solvent such as xylene.

A.d) Alternatively, the compounds of formula (I) wherein E represents *—($C_1$-$C_4$)alkyl-O— can be prepared by deprotecting ketals of structure O using standard conditions like:

using an acid such as diluted aqueous HCl in a solvent such as THF at a temperature ranging from rt to about 50° C.; or using SCX silica gel in a solvent such as MeOH; or using a silica gel bound acid such as tosic acid in a solvent such as MeOH; or using an acid such as formic acid in a solvent such as water at a temperature ranging from about 0° C. to about 50° C.

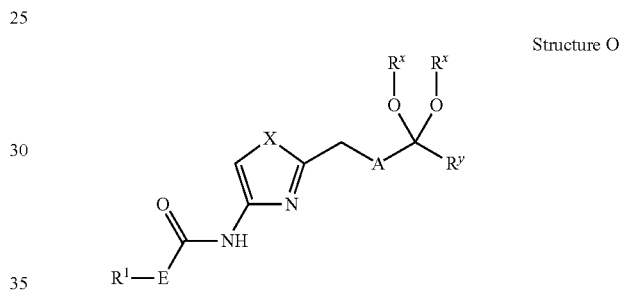

Structure O

A.e) Alternatively, the compounds of formula (I) can be prepared by deprotecting compounds of structure Q using standard conditions like:

Under anhydrous conditions using an acid such as HCl in a solvent mixture such as dioxane/$CH_2Cl_2$ at a temperature about rt; or Under anhydrous conditions using an acid such as trifluoroacetic acid in a solvent such as $CH_2Cl_2$ at a temperature about rt.

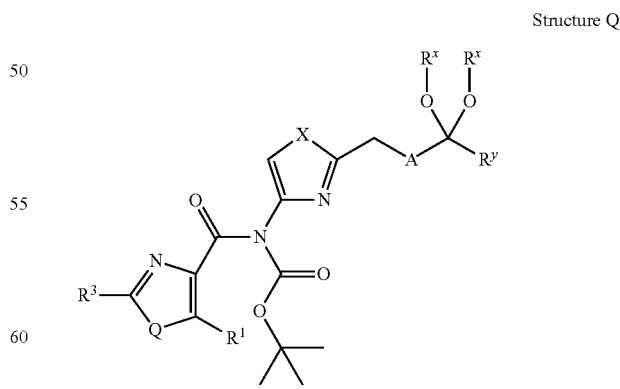

Structure Q

B. Synthesis of Intermediates:

Compounds of structure 1 or their salts can be obtained from compounds of structure G by Boc deprotection under anhydrous conditions in a suitable solvent such as $CH_2Cl_2$ at a temperature about 0° C. in the presence of an acid such as anhydrous hydrochloric acid in dioxane or, alternatively, TFA in a solvent such as CH₂Cl₂.

Compounds of structure G can be obtained from compounds of structure F by Curtius rearrangement at a temperature about 140° C. in a suitable solvent such as xylene followed by reaction with tert-butanol at a temperature about 140° C. in a suitable solvent such as xylene. Alternatively, compounds of structure G can be obtained from the appropriate carboxylic acid derived from the carboxylic ester of structure C via in situ preparation of the corresponding acyl azide and subsequent Curtius rearrangement using azidating reagents such as diphenylphosphoryl azide in a suitable solvent such as a mixture of toluene and tert-butanol and in the presence of a copper salt such as copper chloride and a base such as triethylamine at a temperature ranging from rt to 110° C.

Compounds of structure F can be obtained from the appropriate acid chloride by reaction with an aqueous solution of sodium azide at a temperature about 0° C. in a suitable solvent such as acetone; the above mentioned acid chloride can be prepared by saponification of the corresponding carboxylic ester of structure C with a base such as NaOH at a temperature about rt in a suitable solvent such as THF followed by reaction at a temperature about rt with a reagent such as oxalyl chloride in the presence of DMF in a suitable solvent such as toluene.

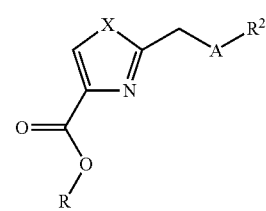

Structure C

Compounds of structure O can be obtained from compounds of structure N by Curtius rearrangement at a temperature about 140° C. in a suitable solvent such as xylene followed by reaction with a suitable alcohol of formula R¹-E-H wherein E represents *—(C₁-C₄)alkyl-O—) at a temperature about 140° C. in a suitable solvent such as xylene.

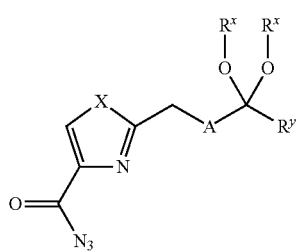

Structure N

Compounds of structure Q can be obtained from compounds of structure P in analogy to the first step described under section A.b).

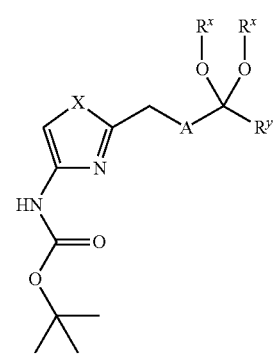

Structure P

Compounds of structure C can be obtained from the respective serine or cysteine derivatives of structure A under dehydrating conditions using either stoichiometric reagents such as the Burgess reagent ((methoxycarbonylsulfamoyl)triethylammonium) hydroxide at a temperature ranging from −10° C. to 80° C. in a suitable solvent such as THF or using catalytic systems such as Ti- or Mo-based catalysts in a suitable solvent such as toluene or CH₂Cl₂ at a temperature ranging from rt to 110° C. to deliver the corresponding oxazoline or thiazoline derivatives. The resulting oxazolines or thiazolines can then be oxidized to the corresponding oxazoles or thiazoles of structure C. Methods for the aromatization include treatment with a base such as DBU and bromotrichloromethane in a suitable solvent such as CH₂Cl₂ at a temperature ranging from −20° C. to rt. Alternatively, the oxazoline or thiazoline may be aromatized to a compound of structure C upon treatment with a mixture of bases such as hexamethylenetetramine and DBU in the presence of copper (II) bromide in a suitable degassed solvent such as CH₂Cl₂ at a temperature ranging from about 0° C. to rt.

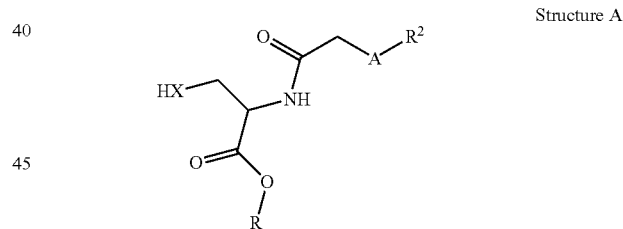

Structure A

Alternatively, compounds of structure C wherein X represents S and R² represents —CO—(C₁-C₃)alkyl can be prepared from the corresponding thioamides of structure XX by treatment with a reagent such as ethyl bromopyruvate in a suitable solvent such as ethanol at a temperature about 80° C. (and subsequent deprotection of the ketal if necessary).

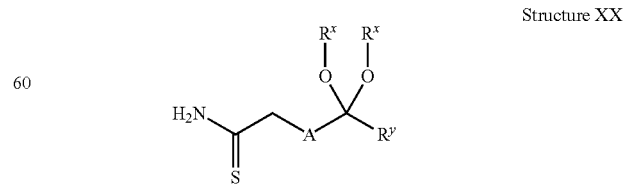

Structure XX

Alternatively, compound of structure C wherein X represents O may be prepared by reaction of a 2-methanesulfonyloxymethyl-oxazole-4-carboxylic acid ester derivative with a compound of structure H-A-R², wherein A represents heterocyclyl and the hydrogen atom of H-A-R² is attached to a nitrogen atom of A, at a temperature about rt in a suitable solvent such as acetone using a base such as $K_2CO_3$ in presence of TBAB.

More specifically, compounds of structure C may be prepared by reaction of 2-methanesulfonyloxymethyl-oxazole-4-carboxylic acid ethyl ester with, in case A represents pyrazole-1,3-diyl, a pyrazole derivative such as 1-(1H-pyrazol-3-yl)-($C_1$-$C_3$)alkan-1-one at a temperature about rt in a suitable solvent such as acetone using a base such as $K_2CO_3$ in presence of TBAB, or analogously, in case A represents pyrazole-1,4-diyl, a pyrazole derivative such as 1H-pyrazole which is substituted in 4-position with halogen.

Compounds of structure C wherein R² represents —$CF_2$—($C_1$-$C_3$)alkyl may be prepared from compounds of structure C wherein R² represents —CO—($C_1$-$C_3$)alkyl by treatment with a fluorinating agent such as (diethylamino)sulphur trifluoride or (bis(2-methoxyethyl)amino)sulphur trifluoride in a solvent such as toluene at a temperature about 60° C.

Alternatively, compounds of structure C wherein R² represents —CO—($C_1$-$C_3$)alkyl can be prepared from compounds of structure K in analogy to the procedures described under section A.d).

Compounds of structure N can be obtained from compounds of structure K in analogy to the synthesis of compounds of structure F from compounds of structure C.

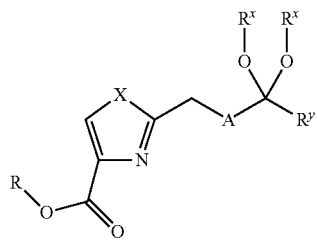

Structure K

Compounds of structure P can be obtained from compounds of structure N in analogy to the synthesis of compounds of structure G from compounds of structure F. Alternatively, compounds of structure P may be obtained from compounds of structure G wherein R² represents —CO—($C_1$-$C_3$)alkyl by ketal formation in the presence of trimethylorthoformate and a catalyst such as $LiBF_4$ in a solvent such as ethylene glycol at a temperature about 95° C.

In general, compounds of structure A can be obtained from coupling between serine methyl ester hydrochloride or cysteine methyl ester hydrochloride with HOOC—$CH_2$-A-R² using standard amide coupling conditions such as EDC/HOBt/DMAP, TBTU, HBTU or PyBOP in the presence of a base such as DIPEA or $Et_3N$ at a temperature about rt in a suitable solvent such as $CH_2Cl_2$. Alternatively, compound of structure A can be obtained by reacting HOOC—$CH_2$-A-R² with isobutyl chloroformate in the presence of a base such as $Et_3N$ at a temperature about –30° C. in a suitable solvent such as $CH_2Cl_2$ followed by treatment with serine methyl ester hydrochloride or cysteine methyl ester hydrochloride at a temperature about –30° C. to rt.

In a more specific way, compounds of structure A wherein A represents oxazole-2,4-diyl may be prepared as described above by coupling of serine or cysteine methyl ester hydrochloride with (4-acetyl-oxazol-2-yl)-acetic acid or (2-acetyl-oxazol-4-yl)-acetic acid, or in case A represents isoxazole-3,5-diyl with (3-acetyl-isoxazol-5-yl)-acetic acid or in case A represents propan-1,3-diyl with 6-oxo-heptanoic acid or, in case A represents thiophen-2,5-diyl with (5-acetyl-thiophen-2-yl)-acetic acid or, in case A represents thiophen-2,4-diyl with (4-acetyl-thiophen-2-yl)-acetic acid or, in case A represents phenyl-1,3-diyl with (3-acetyl-phenyl)-acetic acid or, in case A represents thiazol-2,4-diyl with (4-acetyl-thiazol-2-yl)-acetic acid or (2-acetyl-thiazol-4-yl)-acetic acid or (4-methanesulfonyl-thiazol-2-yl)-acetic acid or, in case A represents thiazol-2,5-diyl with (5-acetyl-thiazol-2-yl)-acetic acid or (2-acetyl-thiazol-5-yl)-acetic acid or, in case A represents oxazole-2,5-diyl with (5-acetyl-oxazol-2-yl)-acetic acid or (2-acetyl-oxazol-5-yl)-acetic acid or another appropriate reagent of formula HOOC—$CH_2$-A-R².

Compounds of structure K can be obtained from compounds of structure I in analogy to the synthesis of compounds of structure C from compounds of structure A.

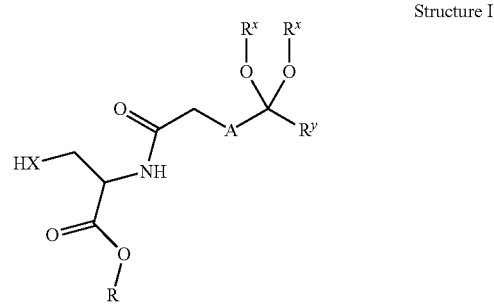

Structure I

Alternatively, compounds of structure K can be obtained from compounds of structure C wherein R² represents —CO—($C_1$-$C_3$)alkyl by ketal formation in the presence of trimethylorthoformate and a catalyst such as $LiBF_4$ in a solvent such as ethylene glycol at a temperature about 95° C.

In a general way, compounds of structure HOOC—$CH_2$-A-R² wherein R² represents —CO—($C_1$-$C_3$)alkyl can be obtained by homologation of compounds of structure CA using the following sequence: a) nitrile formation by reaction with a cyanide salt such as sodium cyanide in a suitable solvent such as DMSO at a temperature ranging from rt to 80° C.; b) hydrolysis of the resulting nitrile using a base such as potassium hydroxide in a solvent mixture such as methanol and water at a temperature ranging from rt to about 80° C. to give compounds of structure CC; c) deprotection of the acetal moiety using a methodology analogous to that described under section A.d). Alternatively, the acid may be obtained by hydrolysis of the above mentioned nitrile (as obtained in a)) using an acid such as HCl or sulphuric acid in a solvent such as water at a temperature ranging from rt to about 100° C. Alternatively, compounds of structure HOOC—$CH_2$-A-R² can be obtained by deprotection of the acetal moiety of compounds of structure CC using a methodology analogous to that described under section A.d).

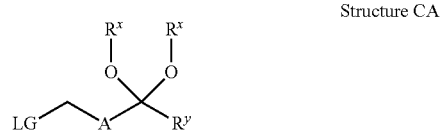

Structure CA

Alternatively, compounds of structure HOOC—$CH_2$-A-R² wherein R² represents —CO—($C_1$-$C_3$)alkyl can be obtained from compounds of structure Br-A-R² such as 1-(3-bromo-phenyl)-ethanone or 1-(4-bromo-thiazol-2-yl)-ethanone by the following sequence: a) ketal formation in the presence of trimethylorthoformate and a catalyst such as LiBF₄ in a solvent such as ethylene glycol at a temperature about 95° C.; b) palladium catalyzed C—C bond formation using a catalyst such as $\{[P(t\text{-}Bu)_3]PdBr\}_2$ in the presence of deprotonated acetic acid tert-butyl ester. Deprotonation can occur, for example, using dicyclohexyl-amine freshly treated with n-BuLi (Takuo Hama and John F. Hartwig, Org. Let., 2008, 10, 1545-1548); and c) treatment with an acid such as TFA or HCl in a solvent such as dioxane, dichloromethane of a mixture of both.

Alternatively, compounds of structure HOOC—CH₂-A-R² wherein R² represents halogen can be obtained from compounds of structure $C_1$—CH₂-A-R² or MsO—CH₂-A-R² using the following sequence: a) nitrile formation by reaction with a cyanide salt such as sodium cyanide in a suitable solvent such as DMSO at a temperature ranging from rt to 80° C.; and b) hydrolysis of the resulting nitrile using a base such as potassium hydroxide in a solvent mixture such as methanol and water at a temperature ranging from rt to about 80° C. Alternatively, the acid may be obtained by hydrolysis of the above mentioned nitrile (as obtained in a)) using an acid such as HCl or sulphuric acid in a solvent such as water at a temperature ranging from rt to about 100° C.

In a general way, compounds of structure XX may be prepared from the corresponding carboxylic acids of structure CC for example by treatment with ethyl chloroformate and a base such as triethylamine followed by an aqueous solution of ammonium chloride at a temperature ranging from 0° C. to rt to get the carboxamide and subsequent reaction with a thiation agent such as Lawesson's reagent in suitable solvent such as THF at a temperature about 70° C. Alternatively, the compounds of structure XX may be prepared from the corresponding nitriles (obtained by reaction of compounds of structure CA with sodium cyanide) using for example hexamethyl-disilathiane in the presence of a base such as sodium methoxide in a suitable solvent such as DMF at a temperature about rt.

Compounds of structure I can be obtained in analogy to the synthesis of compounds of structure A by coupling of serine or cysteine methyl ester hydrochloride with a compound of structure CC, using in case A represents propan-1,3-diyl, an appropriate protected heptanoic acid such as 5-(2-methyl-[1,3]dioxolan-2-yl)-pentanoic acid or, in case A represents thiophen-2,5-diyl, an appropriate protected thiophene derivative such as [5-(2-methyl-[1,3]dioxolan-2-yl)-thiophen-2-yl]-acetic acid or, in case A represents phenyl-1,3-diyl, an appropriate protected phenyl derivative such as [3-(2-methyl-[1,3]dioxolan-2-yl)-phenyl]-acetic acid or, in case A represents thiazol-2,4-diyl, an appropriate protected thiazole derivative such as [4-(2-methyl-[1,3]dioxolan-2-yl)-thiazol-2-yl]-acetic acid or [2-(2-methyl-[1,3]dioxolan-2-yl)-thiazol-4-yl]-acetic acid or, in case A represents thiazol-2,5-diyl, an appropriate protected thiazole derivative such as [5-(2-methyl-[1,3]dioxolan-2-yl)-thiazol-2-yl]-acetic acid or [2-(2-methyl-[1,3]dioxolan-2-yl)-thiazol-5-yl]-acetic acid or, in case A represents oxazole-2,5-diyl, an appropriate protected oxazole derivative such as [5-(2-methyl-[1,3]dioxolan-2-yl)-oxazol-2-yl]-acetic acid or, in case A represents thiophen-2,4-diyl, an appropriate protected thiophene derivative such as [4-(2-methyl-[1,3]dioxolan-2-yl)-thiophen-2-yl]-acetic acid, or, in case A represent oxazole-2,4-diyl an appropriate protected oxazole derivative such as [4-(2-methyl-[1,3]dioxolan-2-yl)-oxazol-2-yl]-acetic acid or [2-(2-methyl-[1,3]dioxolan-2-yl)-oxazol-4-yl]-acetic acid, or in case A represent isoxazole-3,5-diyl an appropriate protected isoxazole derivative such as [3-(2-methyl-[1,3]dioxolan-2-yl)-isoxazol-5-yl]-acetic acid or another appropriate reagent of formula HO₂C—CH₂-A-C(OR^x)₂—(C₁-C₃)alkyl.

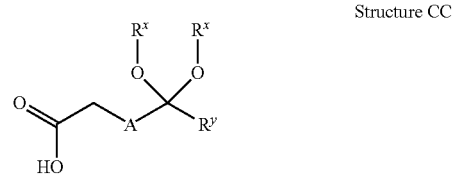

Structure CC

In a general way, compounds of structure CC can be obtained by homologation of compounds of structure CA using the following sequence: a) nitrile formation by reaction with a cyanide salt such as sodium cyanide in a suitable solvent such as DMSO at a temperature ranging from rt to about 80° C.; and b) hydrolysis of the resulting nitrile using a base such as potassium hydroxide in a solvent mixture such as methanol and water at a temperature ranging from rt to about 80° C.

Alternatively, compounds of structure CC can be obtained from compounds of structure Br-A-R² wherein R² represents —CO—(C₁-C₃)alkyl (such as 1-(3-bromo-phenyl)-ethanone) by the following sequence: a) ketal formation in the presence of trimethylorthoformate and a catalyst such as LiBF₄ in a solvent such as ethylene glycol at a temperature about 95° C.; b) palladium catalyzed C—C bond formation in presence of 2-di-t-butylphosphino-2'-methylbiphenyl, tri-potassiumphosphate monohydrate, ethyl acetoacetate and palladium(II)acetate in a solvent such as toluene at a temperature about 90° C. followed by deacetylation at a temperature about 100° C. (Xinglong Jiang, Boaqing Gong, Kapa Prasad, and Oljan Repic, Organic Process Research and Development, 2008, 12, 1164-1169); and c) ester hydrolysis using a base such as NaOH in a solvent such as THF.

2-Methanesulfonyloxymethyl-oxazole-4-carboxylic acid ethyl ester may be prepared by the following sequence: a) oxazole formation by reacting commercially available 3-phenyl-acrylamide with 3-bromo-2-oxo-propionic acid ethyl ester in the presence of a base such as NaHCO₃ in a solvent such as THF at a temperature around 60° C.; b) oxidative cleavage using for example silica gel supported NaIO₄ and a metal complex such as RuCl₃ hydrate in a solvent such as dichloromethane at a temperature about rt; c) reduction with a reducing agent such as NaBH₄ in a solvent such as EtOH at a temperature about 0° C.; d) mesylation using a reagent such as methanesulfonyl chloride in a solvent such as CH₂Cl₂ in the presence of a base such as Et₃N and DMAP at a temperature about 0° C.

More specifically, compounds of structure HOOC—CH₂-A-R², CA, CC, C₁—CH₂-A-R² or MsO—CH₂-A-R² can be prepared as described below:

[5-(2-Methyl-[1,3]dioxolan-2-yl)-thiophen-2-yl]-acetic acid may be prepared by reaction of 2-(5-chloromethyl-thiophen-2-yl)-2-methyl-[1,3]dioxolane with sodium cyanide in a solvent such as DMSO at a temperature about 80° C. followed by hydrolysis of the resulting nitrile using a base such as potassium hydroxide in a solvent mixture such as methanol and water at a temperature ranging from rt to about 80° C.

(5-Acetyl-thiophen-2-yl)-acetic acid may be prepared from [5-(2-methyl-[1,3]dioxolan-2-yl)-thiophen-2-yl]-acetic acid by ketal deprotection in analogy to what described under A.d). Alternatively, (5-acetyl-thiophen-2-yl)-acetic acid may be prepared by reaction of 2-(5-chloromethyl-thiophen-2-yl)-2-methyl-[1,3]dioxolane with sodium cyanide in solvent such as DMSO at a temperature about 80° C. followed by hydrolysis of the resulting nitrile using an acid such as HCl or sulphuric acid in a solvent such as water at a temperature ranging from rt to 100° C.

2-(5-Chloromethyl-thiophen-2-yl)-2-methyl-[1,3]dioxolane may be prepared using the following sequence: a) lithiation of commercially available 2-methyl-2-thiophen-2-yl-[1,3]dioxolane with an organolithium reagent such as n-butyl lithium in the presence of N,N,N',N'-tetramethyl-ethylenediamine in a solvent such as THF at a temperature about −78° C. and subsequent addition of DMF; b) reduction with a reducing agent such as $NaBH_4$ in a solvent such as MeOH at a temperature about 0° C.; c) chlorination of the alcohol using for example methanesulfonyl chloride in the presence of a base such as $Et_3N$ and DMAP in a solvent such as $CH_2Cl_2$ at a temperature about 0° C.

[4-(2-Methyl-[1,3]dioxolan-2-yl)-oxazol-2-yl]-acetic acid may be prepared from methanesulfonic acid 4-(2-methyl-[1,3]dioxolan-2-yl)-oxazol-2-ylmethyl ester in analogy to [5-(2-methyl-[1,3]dioxolan-2-yl)-thiophen-2-yl]-acetic acid.

(4-Acetyl-oxazol-2-yl)-acetic acid may be prepared from methanesulfonic acid 4-(2-methyl-[1,3]dioxolan-2-yl)-oxazol-2-ylmethyl ester in analogy to (5-acetyl-thiophen-2-yl)-acetic acid.

Methanesulfonic acid 4-(2-methyl-[1,3]dioxolan-2-yl)-oxazol-2-ylmethyl ester may be prepared by the following sequence: a) oxazole formation by reacting commercially available 3-phenyl-acrylamide with 3-bromo-2-oxo-propionic acid ethyl ester in the presence of a base such as $NaHCO_3$ in a solvent such as THF at a temperature around 60° C.; b) oxidative cleavage using for example silica gel supported $NaIO_4$ and a metal complex such as $RuCl_3$ hydrate in a solvent such as dichloromethane at a temperature about rt; c) reduction with a reducing agent such as $NaBH_4$ in a solvent such as EtOH at a temperature about 0° C.; d) protection of the alcohol using tert-butyldimethylsilyl chloride in a solvent such as $CH_2Cl_2$ in the presence of a base such as imidazole; e) reduction of the ester group to the aldehyde with a reducing agent such as DiBAL in a solvent such as $CH_2Cl_2$ at a temperature about −78° C.; f) reaction with trimethylaluminum in a solvent such as dichloromethane at a temperature about 0° C.; g) oxidation with an oxidative agent such as $MnO_2$ in a solvent such as acetonitrile at a temperature about rt; h) ketal formation in the presence of trimethylorthoformate and a catalyst such as $LiBF_4$ in a solvent such as ethylene glycol at a temperature about 95° C.; i) deprotection of the silyl ether derivative using a fluorinated agent such as TBAF in a solvent such as THF at a temperature about rt; and j) mesylation using a reagent such as methanesulfonyl chloride in a solvent such as $CH_2Cl_2$ in the presence of a base such as $Et_3N$ and DMAP at a temperature about 0° C.

[3-(2-Methyl-[1,3]dioxolan-2-yl)-isoxazol-5-yl]-acetic acid may be prepared from 5-chloromethyl-3-(2-methyl-[1,3]dioxolan-2-yl)-isoxazole in analogy to [5-(2-methyl-[1,3]dioxolan-2-yl)-thiophen-2-yl]-acetic acid.

(3-Acetyl-isoxazol-5-yl)-acetic acid may be prepared from 5-chloromethyl-3-(2-methyl-[1,3]dioxolan-2-yl)-isoxazole in analogy to (5-acetyl-thiophen-2-yl)-acetic acid.

5-Chloromethyl-3-(2-methyl-[1,3]dioxolan-2-yl)-isoxazole may be prepared using the following sequence: a) protection of commercially available 5-hydroxymethyl-isoxazole-3-carboxylic acid ethyl ester using for example tert-butyldimethylsilyl chloride in the presence of a base such as imidazole in a solvent such as THF; b) reduction of the ester group to the alcohol with a reducing agent such as DiBAL in a solvent such as THF at a temperature below rt; c) oxidation of the alcohol under standard oxidative conditions using reagents such as $MnO_2$ in a solvent such as AcCN at a temperature about rt; d) addition of trimethylaluminum at a temperature about 0° C. in a solvent such as $CH_2Cl_2$; e) oxidation of the alcohol under standard oxidative conditions using reagents such as $MnO_2$ in a solvent such as AcCN at a temperature about rt; e2) ketal formation in the presence of trimethylorthoformate and a catalyst such as $LiBF_4$ in a solvent such as ethylene glycol at a temperature about 95° C.; f) deprotection of the silyl ether derivative using a fluorinated agent such as TBAF in a solvent such as THF at a temperature about rt; g) chlorination of the alcohol using for example methanesulfonyl chloride in the presence of a base such as $Et_3N$ and DMAP in a solvent such as $CH_2Cl_2$ at a temperature about 0° C.

[2-(2-Methyl-[1,3]dioxolan-2-yl)-oxazol-4-yl]-acetic acid may be prepared from methanesulfonic acid 2-(2-methyl-[1,3]dioxolan-2-yl)-oxazol-4-ylmethyl ester in analogy to [5-(2-methyl-[1,3]dioxolan-2-yl)-thiophen-2-yl]-acetic acid.

(2-Acetyl-oxazol-4-yl)-acetic acid may be prepared from methanesulfonic acid 2-(2-methyl-[1,3]dioxolan-2-yl)-oxazol-4-ylmethyl ester in analogy to (5-acetyl-thiophen-2-yl)-acetic acid.

Methanesulfonic acid 2-(2-methyl-[1,3]dioxolan-2-yl)-oxazol-4-ylmethyl ester may be prepared by the following sequence: a) oxazole formation by reacting commercially available 3-phenyl-acrylamide with 3-bromo-2-oxo-propionic acid ethyl ester in the presence of a base such as $NaHCO_3$ in a solvent such as THF at a temperature around 60° C.; b) reduction to the alcohol with a reducing agent such as DiBAL in a solvent such as THF at a temperature about 0° C.; c) protection of the alcohol using tert-butyldimethylsilyl chloride in a solvent such as $CH_2Cl_2$ in the presence of a base such as imidazole; d) oxidative cleavage using for example silica gel supported $NaIO_4$ and a metal complex such as $RuCl_3$ hydrate in a solvent such as $CH_2Cl_2$ at a temperature about rt; e) addition of trimethylaluminum at a temperature about 0° C. in a solvent such as $CH_2Cl_2$; f) oxidation of the alcohol under standard oxidative conditions using reagents such as $MnO_2$ in a solvent such as AcCN at a temperature about rt; g) ketal formation in the presence of trimethylorthoformate and a catalyst such as $LiBF_4$ in a solvent such as ethylene glycol at a temperature about 95° C.; h) deprotection of the silyl ether derivative using a fluorinated agent such as TBAF in a solvent such as THF at a temperature about rt; and i) mesylation of the alcohol using for example methanesulfonyl chloride in the presence of a base such as $Et_3N$ and DMAP in a solvent such as $CH_2Cl_2$ at a temperature about 0° C.

5-(2-Methyl-[1,3]dioxolan-2-yl)-pentanoic acid may be prepared by the following sequence: a) esterification of 6-oxoheptanoic acid in a solvent mixture such as dichloromethane/MeOH under acid catalysis using an acid such as sulphuric acid at a temperature around 55° C.; b) ketal formation in the presence of trimethylorthoformate and a catalyst such as $LiBF_4$ in a solvent such as ethylene glycol at a temperature about 95° C.; c) cleavage of the ester under basic conditions such as 1N NaOH in a solvent such as THF at a temperature around rt.

[4-(2-Methyl-[1,3]dioxolan-2-yl)-thiazol-2-yl]-acetic acid may be prepared from methanesulfonic acid 4-(2-methyl-[1,3]dioxolan-2-yl)-thiazol-2-ylmethyl ester in analogy to [5-(2-methyl-[1,3]dioxolan-2-yl)-thiophen-2-yl]-acetic acid.

(4-Acetyl-thiazol-2-yl)-acetic acid may be prepared from methanesulfonic acid 4-(2-methyl-[1,3]dioxolan-2-yl)-thiazol-2-ylmethyl ester in analogy to (5-acetyl-thiophen-2-yl)-acetic acid.

Methanesulfonic acid 4-(2-methyl-[1,3]dioxolan-2-yl)-thiazol-2-ylmethyl ester may be prepared by the following sequence: a) reaction of commercially available 2,4-dibromo-thiazole with an organolithium reagent such as n-butyl lithium in a solvent such as ether at a temperature about −78° C. and subsequent acetylation with N,N-dimethyl-formamide at a temperature ranging from −78° C. to rt; b) reduction with a reducing agent such as $NaBH_4$ in a solvent such as MeOH at a temperature about rt; c) protection of the alcohol using tert-butyldimethylsilyl chloride in the presence of a base such as imidazole in a solvent such as dichloromethane; d) reaction of the protected alcohol with an organolithium reagent such as n-butyl lithium in a solvent such as ether at a temperature about −78° C. and subsequent acetylation with N,N-dimethylacetamide at a temperature ranging from −78° C. to rt; e) ketal formation in the presence of trimethylorthoformate and a catalyst such as $LiBF_4$ in a solvent such as ethylene glycol at a temperature about 95° C.; f) deprotection of the silyl protecting group under standard conditions such as TBAF in a solvent such as THF at a temperature about rt or 0° C.; g) mesylation using a reagent such as methanesulfonyl chloride in a solvent such as $CH_2Cl_2$ in the presence of a base such as $Et_3N$ and DMAP at a temperature about 0° C.

[2-(2-Methyl-[1,3]dioxolan-2-yl)-thiazol-4-yl]-acetic acid may be prepared from 4-chloromethyl-2-(2-methyl-[1,3]dioxolan-2-yl)-thiazole in analogy to [5-(2-methyl-[1,3]dioxolan-2-yl)-thiophen-2-yl]-acetic acid.

Alternatively, [2-(2-methyl-[1,3]dioxolan-2-yl)-thiazol-4-yl]-acetic acid may be prepared by the following sequence: a) reaction of commercially available 2,4-dibromo-thiazole with an organolithium reagent such as n-butyl lithium in a solvent such as ether at a temperature about −78° C. and subsequent acetylation with N,N-dimethylacetamide at a temperature ranging from −78° C. to rt; b) ketal formation in the presence of trimethylorthoformate and a catalyst such as $LiBF_4$ in a solvent such as ethylene glycol at a temperature about 95° C.; b) palladium catalyzed C—C bond formation in presence of 2-di-t-butylphosphino-2'-methylbiphenyl, tri-potassiumphosphate monohydrate, ethyl acetoacetate and palladium(II)acetate in a solvent such as toluene at a temperature about 90° C. followed by deacetylation at a temperature about 100° C.; c) saponification of the ester moiety in presence of a base such as NaOH in a solvent such as THF at a temperature about rt.

(2-Acetyl-thiazol-4-yl)-acetic acid may be prepared from 4-chloromethyl-2-(2-methyl-[1,3]dioxolan-2-yl)-thiazole in analogy to (5-acetyl-thiophen-2-yl)-acetic acid.

1-(4-Bromo-thiazol-2-yl)-ethanone may be prepared by reaction of commercially available 2,4-dibromo-thiazole with an organolithium reagent such as n-butyl lithium in a solvent such as ether at a temperature about −78° C. and subsequent acetylation with N,N-dimethylacetamide at a temperature ranging from −78° C. to rt;

4-Chloromethyl-2-(2-methyl-[1,3]dioxolan-2-yl)-thiazole may be prepared from 4-chloro-methyl-thiazole-2-carboxylic acid ethyl ester by the following sequence: a) reduction of the ester to the corresponding alcohol under standard reducing conditions using a reagent such as $NaBH_4$ in a solvent such as MeOH at a temperature about rt or, alternatively, a reagent such as DiBAL in a solvent such as THF at a temperature ranging from about −78° C. to rt; b) oxidation of the alcohol to the corresponding aldehyde under standard oxidative conditions using reagents such as $MnO_2$, pyridinium chlorochromate or NMO/TPAP in a solvent such as AcCN or $CH_2Cl_2$ at a temperature about rt; c) addition of an alkyl Grignard reagent at a temperature below rt (preferably about −78° C.) in a solvent such as THF, or, alternatively, addition of a trialkylaluminum reagent at a temperature about 0° C. in a solvent such as $CH_2Cl_2$ providing the corresponding secondary alcohol; d) oxidation of the alcohol under standard oxidative conditions using reagents such as TPAP/NMO or $MnO_2$ in a solvent such as $CH_2Cl_2$ or AcCN at a temperature about rt; d) ketal formation in the presence of trimethylorthoformate and a catalyst such as $LiBF_4$ in a solvent such as ethylene glycol at a temperature about 90° C.

4-Chloromethyl-thiazole-2-carboxylic acid ethyl ester may be prepared by the following sequence: a) reaction of commercially available oxalamic acid ethyl ester with Lawesson's reagent in a solvent such as toluene at a temperature about 80° C.; and b) cyclization with 1,3-dichloroacetone in a solvent such as toluene at a temperature about 110° C.

[5-(2-Methyl-[1,3]dioxolan-2-yl)-thiazol-2-yl]-acetic acid may be prepared from methanesulfonic acid 5-(2-methyl-[1,3]dioxolan-2-yl)-thiazol-2-ylmethyl ester in analogy to [5-(2-methyl-[1,3]dioxolan-2-yl)-thiophen-2-yl]-acetic acid.

(5-Acetyl-thiazol-2-yl)-acetic acid may be prepared from methanesulfonic acid 5-(2-methyl-[1,3]dioxolan-2-yl)-thiazol-2-ylmethyl ester in analogy to (5-acetyl-thiophen-2-yl)-acetic acid.

Methanesulfonic acid 5-(2-methyl-[1,3]dioxolan-2-yl)-thiazol-2-ylmethyl ester may be prepared by the following sequence: a) reaction of commercially available 2-bromo-thiazole-5-carbaldehyde with trimethylaluminum in a solvent such as dichloromethane at a temperature about 0° C.; b) oxidation with an oxidative agent such as $MnO_2$ in a solvent such as acetonitrile at a temperature about rt; c) ketal formation in the presence of trimethylorthoformate and a catalyst such as $LiBF_4$ in a solvent such as ethylene glycol at a temperature about 95° C.; d) lithiation with an organolithium reagent such as n-butyl lithium in a solvent such as ether at a temperature about −78° C. and subsequent formylation with N,N-dimethylformamide; e) reduction with a reducing agent such as $NaBH_4$ in a solvent such as MeOH at a temperature about rt; f) mesylation using a reagent such as methanesulfonyl chloride in a solvent such as $CH_2Cl_2$ in the presence of a base such as $Et_3N$ and DMAP at a temperature about 0° C.

[2-(2-Methyl-[1,3]dioxolan-2-yl)-thiazol-5-yl]-acetic acid may be prepared from 5-chloromethyl-2-(2-methyl-[1,3]dioxolan-2-yl)-thiazole in analogy to [5-(2-methyl-[1,3]dioxolan-2-yl)-thiophen-2-yl]-acetic acid.

(2-Acetyl-thiazol-5-yl)-acetic acid may be prepared from 5-chloromethyl-2-(2-methyl-[1,3]dioxolan-2-yl)-thiazole in analogy to (5-acetyl-thiophen-2-yl)-acetic acid.

5-Chloromethyl-2-(2-methyl-[1,3]dioxolan-2-yl)-thiazole may be prepared by the following sequence: a) reduction of commercially available 2-bromo-thiazole-5-carbaldehyde with a reducing agent such as $NaBH_4$ in a solvent such as MeOH at a temperature about rt; b) protection of the alcohol using tert-butyldimethylsilyl chloride in a solvent such as $CH_2Cl_2$ in the presence of a base such as imidazole; c) lithiation with an organolithium reagent such as n-butyl lithium in a solvent such as ether at a temperature about −78° C. and subsequent acetylation with N,N-dimethylacetamide; d) ketal formation in the presence of trimethylorthoformate and a catalyst such as $LiBF_4$ in a solvent such as ethylene glycol at a temperature about 95° C.; e) deprotection of the silyl ether derivative using a fluorinated agent such as TBAF in a solvent such as THF at a temperature about rt; and f) chlorination using a reagent such as methanesulfonyl chloride in a solvent such as CH$_2$Cl$_2$ in the presence of a base such as Et$_3$N and DMAP at a temperature about 0° C.

[5-(2-Methyl-[1,3]dioxolan-2-yl)-oxazol-2-yl]-acetic acid may be prepared from 2-chloromethyl-5-(2-methyl-[1,3]dioxolan-2-yl)-oxazole in analogy to [5-(2-methyl-[1,3]dioxolan-2-yl)-thiophen-2-yl]-acetic acid.

(5-Acetyl-oxazol-2-yl)-acetic acid may be prepared from 2-chloromethyl-5-(2-methyl-[1,3]dioxolan-2-yl)-oxazole in analogy to (5-acetyl-thiophen-2-yl)-acetic acid.

2-Chloromethyl-5-(2-methyl-[1,3]dioxolan-2-yl)-oxazole may be prepared using the following sequence: a) lithiation of commercially available oxazole with an organolithium reagent such as n-butyl lithium in a solvent such as THF at a temperature about −78° C. and subsequent addition of DMF; b) reduction with a reducing agent such as NaBH$_4$ in a solvent such as MeOH at a temperature about 0° C.; c) protection of the alcohol using tert-butyldimethylsilyl chloride in the presence of a base such as imidazole in a solvent such as THF; d) lithiation with an organolithium reagent such as t-butyl lithium in a solvent such as THF at a temperature ranging from −78° C. to −40° C. and subsequent formylation with DMF at a temperature ranging from −78° C. to rt; e) reaction with trimethylaluminum in a solvent such as dichloromethane at a temperature about 0° C.; f) oxidation with an oxidative agent such as MnO$_2$ in a solvent such as acetonitrile at a temperature about rt; g) ketal formation and deprotection of the silyl protection group in the presence of trimethylorthoformate and a catalyst such as LiBF$_4$ in a solvent such as ethylene glycol at a temperature about 95° C.; h) chlorination of the alcohol using for example Ms-Cl in the presence of a base such as Et$_3$N and DMAP in a solvent such as CH$_2$Cl$_2$ at a temperature about 0° C.

[3-(2-Methyl-[1,3]dioxolan-2-yl)-phenyl]-acetic acid may be prepared from 3'-bromoacetophenone by the following sequence: a) ketal formation in the presence of trimethylorthoformate and a catalyst such as LiBF$_4$ in a solvent such as ethylene glycol at a temperature about 95° C.; b) palladium catalyzed C—C bond formation in presence of 2-di-t-butylphosphino-2'methylbiphenyl, tri-potassiumphosphate monohydrate, ethyl acetoacetate and palladium(II)acetate in a solvent such as toluene at a temperature about 90° C. followed by deacetylation at a temperature about 100° C.; c) saponification of the ester moiety in the presence of a base such as NaOH in a solvent such as THF at a temperature about rt.

(3-Acetyl-phenyl)-acetic acid may be prepared from 3'-bromoacetophenone by the following sequence: a) ketal formation in the presence of trimethylorthoformate and a catalyst such as LiBF$_4$ in a solvent such as ethylene glycol at a temperature about 95° C.; b) palladium catalyzed C—C bond formation using a catalyst such as {[P(t-Bu)$_3$]PdBr}$_2$ in the presence of deprotonated acetic acid tert-butyl ester. Deprotonation can occur, for example, using dicyclohexylamine freshly treated with n-BuLi; c) deprotection in the presence of an acid such as TFA at a temperature about rt.

[4-(2-Methyl-[1,3]dioxolan-2-yl)-thiophen-2-yl]-acetic acid may be prepared from 2-(5-chloromethyl-thiophen-3-yl)-2-methyl-[1,3]dioxolane in analogy to [5-(2-methyl-[1,3]dioxolan-2-yl)-thiophen-2-yl]-acetic acid.

(4-Acetyl-thiophen-2-yl)-acetic acid may be prepared from 2-(5-chloromethyl-thiophen-3-yl)-2-methyl-[1,3]dioxolane in analogy to (5-acetyl-thiophen-2-yl)-acetic acid.

2-(5-Chloromethyl-thiophen-3-yl)-2-methyl-[1,3]dioxolane may be prepared as described for 5-chloromethyl-2-(2-methyl-[1,3]dioxolan-2-yl)-thiazole but starting with commercially available 4-bromo-thiophene-2-carbaldehyde.

(4-Methanesulfonyl-thiazol-2-yl)-acetic acid may be prepared from methanesulfonic acid 4-methanesulfonyl-thiazol-2-ylmethyl ester by reaction with sodium cyanide in a solvent such as DMSO at a temperature about 80° C. followed by hydrolysis of the resulting nitrile using a base such as potassium hydroxide in a solvent mixture such as methanol and water at a temperature ranging from rt to about 80° C. Alternatively, hydrolysis of the resulting nitrile may be performed using an acid such as HCl or sulphuric acid in a solvent such as water at a temperature ranging from rt to 100° C.

Methanesulfonic acid 4-methanesulfonyl-thiazol-2-ylmethyl ester may be prepared using the following sequence: a) reaction of commercially available 2,4-dibromo-thiazole with an organolithium reagent such as n-butyl lithium in a solvent such as ether at a temperature about −78° C. and subsequent formylation with N,N-dimethyl-formamide at a temperature ranging from −78° C. to rt; b) reduction with a reducing agent such as NaBH$_4$ in a solvent such as MeOH at a temperature about rt; c) protection of the alcohol using tert-butyldimethylsilyl chloride in the presence of a base such as imidazole in a solvent such as dichloromethane; d) lithiation with an organolithium reagent such as n-butyl lithium in a solvent such as ether at a temperature about −78° C. and subsequent treatment with methyl disulfide; e) oxidation with m-CPBA in a solvent such as CH$_2$Cl$_2$ at a temperature about rt; f) deprotection of the silyl ether derivative using an acid such as p-toluene sulfonic acid in a solvent such as MeOH at a temperature about rt; g) mesylation of the alcohol using for example Ms-Cl in the presence of a base such as Et$_3$N and DMAP in a solvent such as CH$_2$Cl$_2$ at a temperature about 0° C.

(2-Acetyl-oxazol-5-yl)-acetic acid may be prepared from methanesulfonic acid 2-acetyl-oxazol-5-ylmethyl ester in analogy to (5-acetyl-thiophen-2-yl)-acetic acid.

Methanesulfonic acid 2-acetyl-oxazol-5-ylmethyl ester may be prepared may be prepared using the following sequence: a) reaction of commercially available oxazole with an organomagnesium reagent such as isopropylmagnesium chloride in a solvent such as THF at a temperature about −15° C. and subsequent acetylation with N-methoxy-N-methylacetamide at a temperature ranging from −15° C. to rt; b) reduction with a reducing agent such as NaBH$_4$ in a solvent such as MeOH at a temperature about rt; c) protection of the alcohol using tert-butyldimethylsilyl chloride in the presence of a base such as imidazole in a solvent such as THF; d) reaction of the protected alcohol with an organolithium reagent such as t-butyl lithium in a solvent such as THF at a temperature ranging from −78° C. to −40° C. and subsequent formylation with N,N-dimethyl-formamide at a temperature ranging from −78° C. to rt; e) reduction with a reducing agent such as NaBH$_4$ in a solvent such as MeOH at a temperature about rt; g) protection of the primary alcohol using 3,4-dihydro-2H-pyran in the presence of pyridinium toluene-4-sulfonate in a solvent such as CH$_2$Cl$_2$; h) deprotection of the silyl ether derivative using a fluorinated agent such as TBAF in a solvent such as THF at a temperature about rt; i) oxidation of the resulting secondary alcohol using an oxidizing agent such as MnO$_2$ in a solvent such as CH$_2$Cl$_2$; j) removal of the protecting group using an acid such as Amberlyst 15 in a suitable solvent such as MeOH at a temperature about 35° C.; and k) mesylation of the alcohol using for example Ms-Cl in the presence of a base such as Et$_3$N and DMAP in a solvent such as CH$_2$Cl$_2$ at a temperature ranging from 0° C. to rt.

2-(5-Chloromethyl-furan-2-yl)-2-methyl-[1,3]dioxolane may be prepared using the following sequence: a) protection of commercially available 1-furan-2-yl-ethanone in the presence of trimethylorthoformate and a catalyst such as LiBF$_4$ in a solvent such as ethylene glycol at a temperature about 95° C.; b) lithiation with an organolithium reagent such as n-butyl lithium in a solvent such as THF at a temperature about −78° C. and subsequent addition of DMF; c) reduction with a reducing agent such as NaBH₄ in a solvent such as MeOH at a temperature about 0° C.; and d) chlorination of the alcohol using for example methanesulfonyl chloride in the presence of a base such as Et₃N and DMAP in a solvent such as CH₂Cl₂ at a temperature about 0° C.

[5-(2-Methyl-[1,3]dioxolan-2-yl)-furan-2-yl]-acetic acid may be prepared from 2-(5-chloromethyl-furan-2-yl)-2-methyl-[1,3]dioxolane in analogy to [5-(2-methyl-[1,3]dioxolan-2-yl)-thiophen-2-yl]-acetic acid.

(5-Acetyl-furan-2-yl)-acetic acid may be prepared from 2-(5-chloromethyl-furan-2-yl)-2-methyl-[1,3]dioxolane in analogy to (5-acetyl-thiophen-2-yl)-acetic acid.

Chloroformates or acid chlorides of formula R¹-E-COCl or carboxylic acids of formula R¹-E-COOH are commercially available or synthesized according to well known methods e.g. from commercially available benzoic acids, benzaldehydes, benzyl alcohols or their heterocyclic analogues.

Acids of formula R¹-E-COOH, which are also compounds of structure 6 are well known in the art or are prepared according to the methods described below.

Structure 6

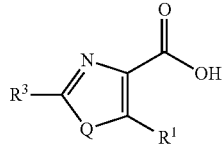

Compounds of structure 6 wherein R³ represents Me and Q represents O may be prepared as described in Scheme 1 by reacting 3-oxo-propionic acid ester derivatives with an aqueous solution of sodium nitrite in presence of an acid such as glacial acetic acid. Subsequent transformation of the oxime with acetic anhydride in presence of an acid such as glacial acetic acid and catalytic amounts of metal chlorides such as mercury chloride or zinc chloride and zinc powder followed by cyclization under dehydrating conditions such as thionyl chloride in chloroform followed by saponification of the ester function using methods known in the art such as treatment with a base such as NaOH in a solvent or a solvent mixture such as ethanol/water or THF afforded the desired acid derivative. The respective 3-oxo-propionic acid ester derivatives are commercially available or well known in the art.

Scheme 1: Oxazole synthesis (1).

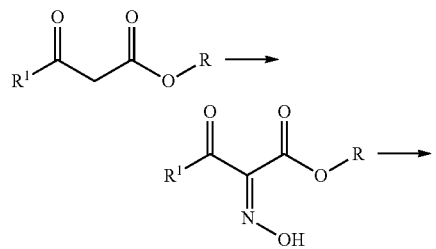

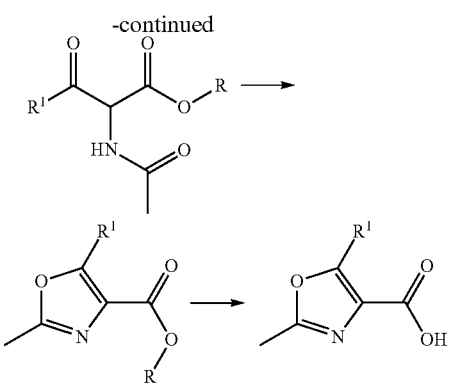

Alternatively, compounds of structure 6 wherein Q represents O may be prepared as described in Scheme 2 by reacting 3-oxo-propionic acid ester derivatives with a solution of 4-acetamido-benzenesulfonyl azide and a base such as Et₃N. Subsequent treatment with a carboxamide derivative and a catalyst such as tetrakis(acetato)dirhodium(II)dihydrate followed by cyclization using triphenylphosphine and iodine in the presence of a base such as Et₃N afforded the respective ester derivative. Saponification of the ester function using methods known in the art such as treatment with a base such as NaOH in a solvent or a solvent mixture such as ethanol/water or THF afforded the desired acid derivative. The respective 3-oxo-propionic acid ester derivatives are commercially available or well known in the art.

Scheme 2: Oxazole synthesis (2).

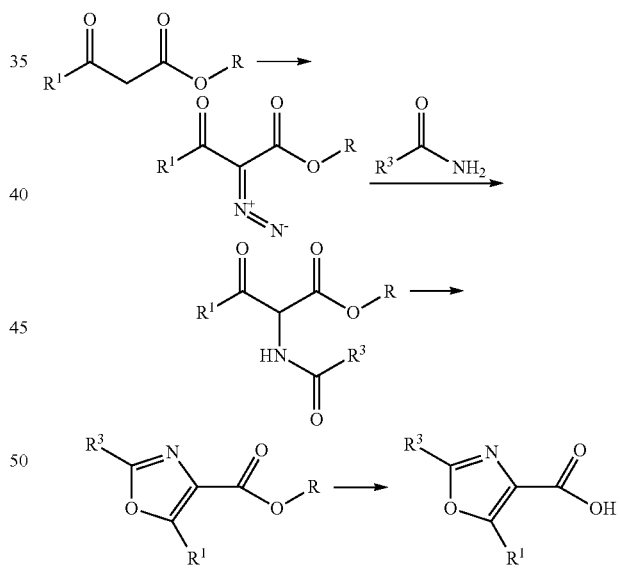

Alternatively, compounds of structure 6 wherein R³ represents hydrogen and Q represents O may be prepared as described in Scheme 2b by reacting a solution of an acid derivative of formula R¹COOH with methyl isocyanoacetate in the presence of a base such as potassium carbonate sesquihydrate or DIPEA and DPPA in a solvent such as DMF. Saponification of the ester function using methods known in the art such as treatment with a base such as NaOH in a solvent or a solvent mixture such as ethanol/water or THF afforded the respective acid derivative. The respective acids R¹COOH are commercially available or well known in the art.

Scheme 2b: Oxazole synthesis (3).

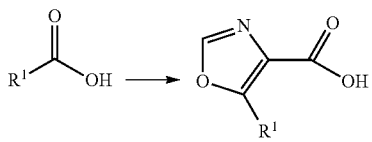

Alternatively, compounds of structure 6 wherein Q represents O may be prepared as described in Scheme 3 by esterification of a 3-phenylserine derivative using a reagent such as thionylchloride in a solvent such as MeOH at a temperature about 0° C. followed by coupling with a carboxylic acid derivative $R^3$—COOH using standard conditions such as HOBt, DCC, N-methylmorpholine in a solvent such as $CH_2Cl_2$ at a temperature about 0° C. Oxidation of the alcohol with an oxidative reagent such as Dess-Martin periodinane in a solvent such as $CH_2Cl_2$ followed by cyclization using triphenylphosphine and iodine in the presence of a base such as $Et_3N$ afforded the respective oxazole derivative. The desired acid derivatives may be obtained by saponification of the ester function using methods known in the art such as treatment with a base such as aq. LiOH in a solvent such as dioxane.

Scheme 3: Oxazole synthesis (4).

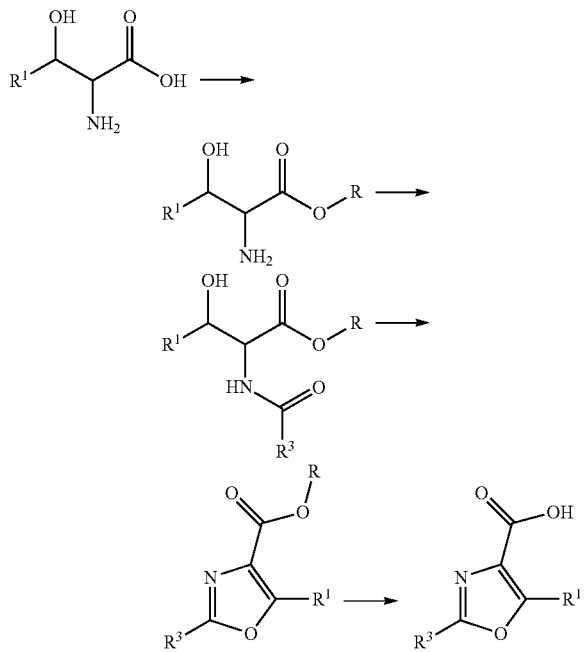

Alternatively, compounds of structure 6 wherein Q represents O may be prepared as described in Scheme 4 using the following sequence: a) formation of an acid chloride by treatment of a suitable acid of formula $R_1COOH$ with oxalyl chloride and catalytic DMF in a solvent such as 1,2-dichloroethane at a temperature around rt; b) cyclization of the resulting acid chloride in a solvent such as THF using ethyl isocyanoacetate in presence of a base such as $Et_3N$ and DMAP at a temperature of about 75° C.; c) opening of the resulting oxazole using acetylchloride in a solvent such as EtOH at a temperature between 10 and 85° C.; d) reaction of the amine with an anhydride of formula $R^3C(O)$—O—$C(O)$ $R^3$ in the presence of a base such as sodium acetate in a solvent such as water. Alternatively, the amine may be reacted with an appropriate acid chloride of formula $R^3C(O)Cl$ in the presence of a base such as triethylamine; e) cyclization upon addition of an acid such as conc. sulphuric acid at a temperature around rt; and f) saponification of the ester function using methods known in the art such as treatment with a base such as aq. NaOH in a solvent such as THF.

Scheme 4: Oxazole synthesisi (5).

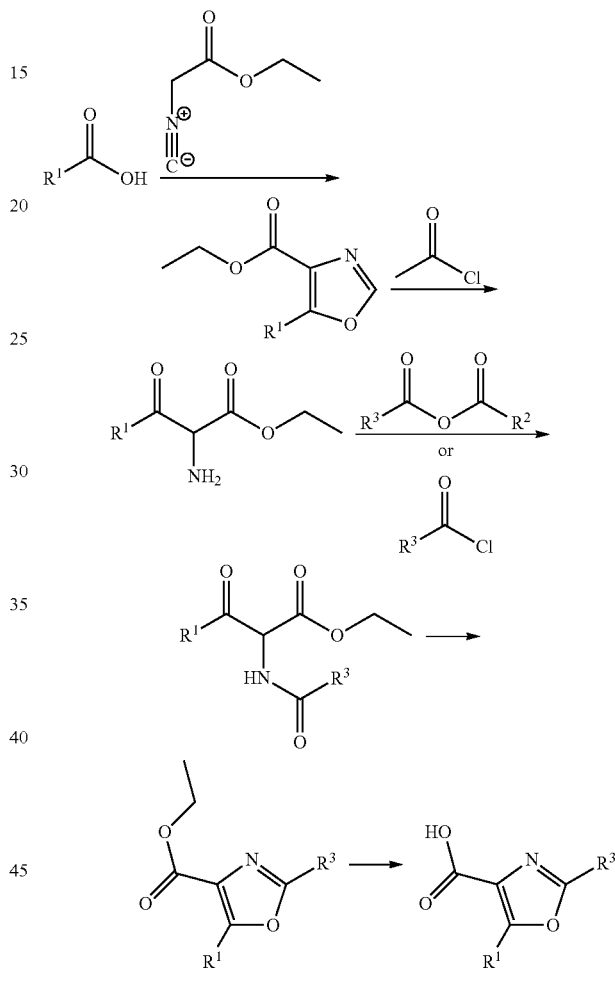

Compounds of structure 6 wherein Q represents S may be prepared by first reacting methyl dichloroacetate with commercially available benzaldehyde derivatives $R^1$—CHO in the presence of a base such as KOt-Bu in a solvent such as THF. The desired compounds of structure 6 wherein Q represents S and $R^3$ represents $(C_1-C_4)$alkyl or cyclopropyl are obtained as described in Scheme 5 by subsequent transformation (cyclization) with the respective thioamides in a solvent such as MeCN followed by saponification of the ester function using methods known in the art such as treatment with a base such as NaOH in a solvent such as MeOH. The respective benzaldehydes $R^1$—CHO are commercially available or well known in the art. The thioamides are commercially available or, alternatively, can be synthesized from commercially available carboxamides with Lawesson's reagent.

Scheme 5: Thiazole synthesis (1), wherein R³ represents (C₁-C₄)alkyl or cyclopropyl.

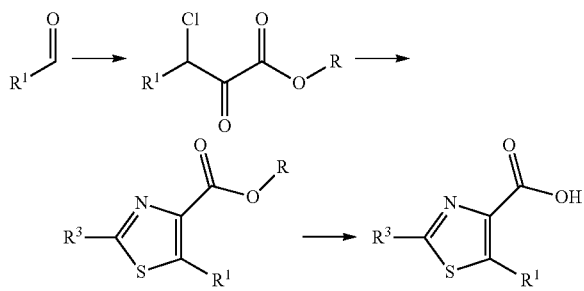

Alternatively, the desired compounds of structure 6 wherein Q represents S and R³ represents hydrogen are obtained as described in Scheme 6 by reacting methyl dichloroacetate with commercially available benzaldehyde derivatives R¹—CHO in the presence of a base such as KOt-Bu in a solvent such as THF. A subsequent transformation with commercially available thiourea followed by treatment with a base such as sodium bicarbonate afforded the amino-thiazole derivative. Sandmeyer transformation using a Cu(II) derivative such as CuBr₂ followed by hydrogenation in the presence of a metal catalyst such as Pd/C, Pt/C or PtO₂ afforded the desired ester. Saponification of the ester function can be performed using methods known in the art such as treatment with a base such as NaOH in a solvent such as MeOH.

Scheme 6: Thiazole synthesis (2).

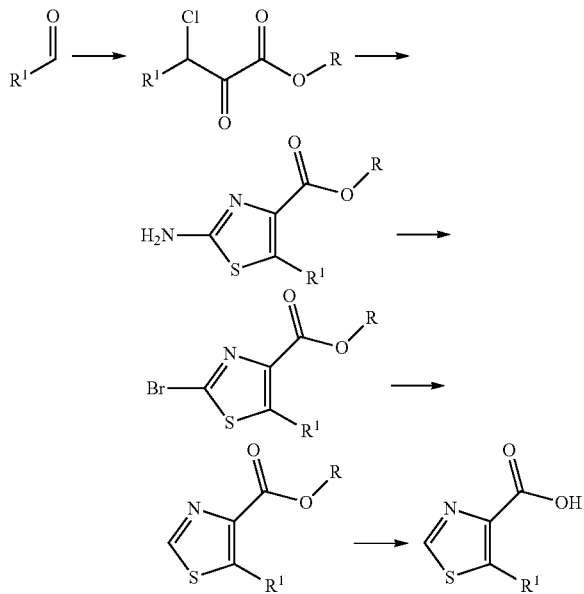

Corresponding acid chlorides of acids of structure 6 are prepared at a temperature about rt from the corresponding carboxylic acids by reaction with a reagent such as oxalyl chloride in presence of DMF in a suitable solvent such as toluene.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as Et₃N or diethylamine) and eluent B (hexane), at a flow rate of 0.8 to 150 mL/min.

EXPERIMENTAL PART

Abbreviations (as used herein and in the description above)
Ac acetyl
AcCl acetyl chloride
AcCN acetonitrile
AcOH acetic acid
aq. aqueous
atm atmosphere
Boc tert-butoxycarbonyl
bp boiling point
BSA bovine serum albumin
Bu butyl
BuLi n-butyllithium
ca. about
cat. catalytic
COAD chronic obstructive airway disease
COLD chronic obstructive lung disease
COPD chronic obstructive pulmonary disease
DAD diode array detector
DBU 1,8-Diazabicyclo[5.4.0]undec-7-ene
DC dendritic cells
DCC N,N'-dicyclohexylcarbodiimide
PL-DCC polymer supported N,N'-dicyclohexylcarbodiimide
DCE 1,2-dichloroethane
DIPEA diisopropylethylamine
DiBAL di-iso-butylaluminum hydride
DMAP 4-N,N-dimethylaminopyridine
DMF dimethylformamide
DMSO dimethylsulfoxide
DPPA diphenyl phosphoryl azide
EA ethyl acetate
EC₅₀ half maximal effective concentration
EIA enzyme immunoassay
EDC N-(3-dimethylaminopropyl)-N'-ethyl-carbodiimide hydrochloride
ELSD evaporative light-scattering detection
eq. equivalent(s)
ES+ electro-spray, positive ionization
Et ethyl
Ether or Et₂O diethylether
Et₃N triethylamine
EtOH ethanol
FA formic acid
FAD familial autosomic dominant
FC flash column chromatography on silica gel
FLIPR fluorescence imaging plate reader
FPRL1 formyl-peptide receptor like-1
FPRL2 formyl-peptide receptor like-2
h hour(s)
HATU 2-(7-aza-1H-benzotriazol-1-yl)-1,1,3,3-tetramethyluronium hexafluorophosphate
HBTU O-(benzotriazol-1-yl)-N,N,N',N'-tetramethyluronium hexafluorophosphate
HBSS hanks' balanced salt solution
hept heptane
HIV human immunodeficiency virus
HOBt hydroxybenzotriazole
HOAt 7-aza-1-hydroxybenzotriazole
HPLC high performance liquid chromatography LC-MS liquid chromatography-mass spectrometry
lem emission wavelength
lex excitation wavelength
LPS lipopolysaccharide
m-CPBA meta-chloroperbenzoic acid
Me methyl
MeOH methanol
min minute(s)
mM millimolar
µM micromolar
mRNA messenger ribonucleic acid
MPLC medium pressure liquid chromatography
MS mass spectrometry
Ms methanesulfonyl
nm nanometer
nM nanomolar
NMO N-methyl-morpholine-N-oxide
NMR nuclear magnetic resonance
OAc acetate
org. organic
p para
p-TsOH para-toluene sulfonic acid
PG protecting group
PL-Deta polystyrene supported diethylenetriamine
PL-HCO3 polystyrene supported hydrogen carbonate, version MP (macro porous)
PyBOP benzotriazol-1-yl-oxy-tris-pyrrolidino-phosphonium-hexafluoro-phosphate
Rochelle's salt potassium sodium tartrate
rf retention factor
rpm rotation per minute
rt room temperature
sat. saturated
SCX strong cation exchanger
Si-DCC silica bound DCC from silicycle
sol. solution
TBA(B) tetra-n-butylammonium (bromide)
TBAF tetra-n-butylammonium fluoride
TBME tert-butyl methyl ester
TBDMS tert-butyl-dimethyl-silyl
TBDPS tert-butyl-diphenyl-silyl
TBTU O-(benzotriazol-1-yl)-N,N,N',N'-tetramethyluronium tetrafluoroborate
tBu tert-butyl, tertiary butyl
TFA trifluoroacetic acid
THF tetrahydrofuran
TIPS tri-isopropyl-silyl
TLC thin layer chromatography
TMS trimethyl-silyl
TPAP tetrapropylammonium perruthenate
$t_R$ retention time
TsOH p-toluene sulfonic acid monohydrate
UV ultra violet
V is visible I Chemistry
General.

All temperatures are stated in degrees Celsius (° C.). Unless otherwise indicated, the reactions take place at rt.

As SCX material SiliaBond® SCX from Silicycle was used.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm); elution with EA, hept, $CH_2Cl_2$, $CHCl_3$, MeOH or mixtures thereof.

MPLC was performed using Isolute® SPE Flash SI II columns from international sorbent technology, elution with EA, hept, $CH_2Cl_2$, MeOH or mixtures thereof.

LC-MS-conditions 01 (if not indicated otherwise): Analytical: Thermo Finnigan MSQ Surveyor MS with Agilent 1100 Binary Pump and DAD. Column: Zorbax SB-AQ 5 µm, 4.6×50 mm ID from Agilent Technologies. Eluents: A: $H_2O$+ 0.04% TFA; B: AcCN; Gradient: 5% B→95% B over 1 min. Flow: 4.50 mL/min. Detection: UV/Vis+MS, $t_R$ is given in min.

LC-MS-conditions 02 (if not indicated otherwise): Analytical: Thermo Finnigan MSQ Plus MS with Agilent 1100 Binary Pump and DAD. Column: Zorbax SB-AQ 5 µm, 4.6× 50 mm ID from Agilent Technologies. Eluents: A: $H_2O$+ 0.04% TFA; B: AcCN; Gradient: 5% B→95% B over 1 min. Flow: 4.50 mL/min. Detection: UV/Vis and/or ELSD+MS, $t_R$ is given in min.

LC-MS-conditions 05 (if not indicated otherwise): Analytical: Dionex GHP 3200 Binary Pump, MS: Thermo MSQ Plus, DAD: Dionex PDA 3000, ELSD: Sedere Sedex 85. Column: Xbridge C18 5 µM, 4.6×50 mm ID from Waters, thermostated in the Dionex TCC-3200 compartment. Eluents: A: $H_2O$+0.04% TFA; B: AcCN. Method: Gradient: 5% B→95% B over 1.0 min. Flow: 4.5 mL/min. Detection: UV/Vis and/or ELSD, and MS, $t_R$ is given in min.

LC-MS-conditions 05b (if not indicated otherwise): Analytical: Dionex GHP 3200 Binary Pump, MS: Thermo MSQ Plus, DAD: Dionex PDA 3000, ELSD: Sedere Sedex 85. Column: Zorbax Extend C18 1.8 µM, 4.6×20 mm from Agilent Technologies, thermostated in the Dionex TCC-3200 compartment. Eluents: A: $H_2O$+0.04% TFA; B: AcCN. Method: Gradient: 5% B→95% B over 1.0 min. Flow: 4.5 mL/min. Detection: UV/Vis and/or ELSD, and MS, $t_R$ is given in min.

LC-MS-conditions 06 (if not indicated otherwise): Analytical: Dionex HPG-3000 Binary Pump, MS: Thermo MSQ MS, DAD: Dionex PDA 3000, ELSD: PolymerLab ELS 2100. Column: Ascentis C18 2.7 µm, 3×30 mm ID from Sigma-Aldrich, thermostated in the Dionex TCC-3000 compartment. Eluents: A: $H_2O$+0.05% FA; B: AcCN. Method: Gradient: 5% B→95% B over 2.40 min. Flow: 3.0 mL/min. Detection: UV/Vis and/or ELSD, and MS, $t_R$ is given in min.

LC-MS-conditions 07 (if not indicated otherwise): Analytical: Dionex HPG-3000 Binary Pump, MS: Thermo MSQ MS, DAD: Dionex PDA 3000, ELSD: PolymerLab ELS 2100. Column: Ascentis Express C18 2.7 µm, 2.1×30 mm ID from Sigma-Aldrich, thermostated in the Dionex TCC-3000 compartment. Eluents: A: $H_2O$+0.04% FA; B: AcCN. Method: Gradient: 5% B→95% B over 2.40 min. Flow: 1.8 mL/min. Detection: UV/Vis and/or ELSD, and MS, $t_R$ is given in min.

HPLC preparative: X-Bridge C18 5 µm, 50×19 mm ID from Waters. Eluents: A: $H_2O$+0.5% $NH_4OH$; B: AcCN; Gradient: 10% B→90% B over 5 min. Flow: 40.0 mL/min. Detection: UV/Vis and/or ELSD.

HPLC chiral, analytical: a) Regis Whelk column, 4.6×250 mm, 10 µm. Eluent A: EtOH+0.05% $Et_3N$. Eluent B: hexane. Flow: 1 mL/min. b) ChiralPak AD, 4.6×250 mm, 5 µm. Eluent A: EtOH+0.05% $Et_3N$. Eluent B: hexane. Flow: 1 mL/min. c) ChiralCel OD, 4.6×250 mm, 10 µm. Eluent A: EtOH+0.1% $Et_3N$. Eluent B: hexane. Flow: 0.8 mL/min.

HPLC chiral, preparative: a) Regis Whelk 01 column, 50×250 mm. Flow: 100 mL/min. b) ChiralPak AD, 20×250 mm. Flow: 10 mL/min. c) ChiralCel OD, 20 μm, 50 mm×250 mm. Flow: 100 mL/min.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

GENERAL PROCEDURES

General Procedure E: Ester Hydrolysis

A 0.5M solution of the respective carboxylic acid ester (1.0 eq.) in a 3:1 mixture of THF and the corresponding alkyl alcohol, e.g. MeOH or EtOH, was treated with 1M aq. NaOH (2.0 eq.). After stirring for 3 h, a white suspension was formed and the org. volatiles were removed under reduced pressure. The remaining mixture was diluted with water (half the amount of the 3:1 mixture of THF and MeOH), cooled with an ice-bath and acidified (pH=3-4) by addition of 1M aq. HCl. The suspension was filtered and the residue was washed with cold water to afford the desired carboxylic acid derivative after drying.

General Procedure F: Synthesis of 2-acetylamino-3-oxo-propionic Acid Ester Derivatives

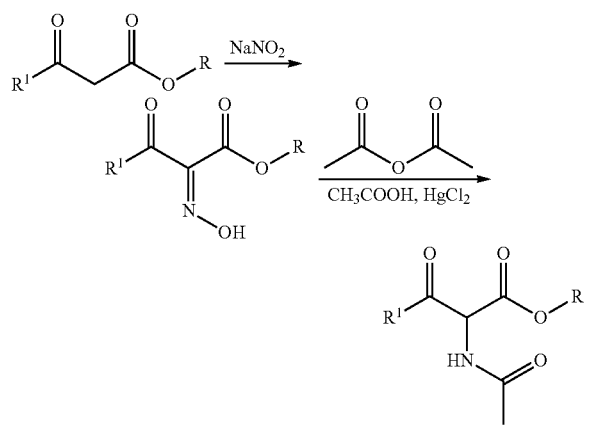

In a flame dried round-bottomed flask equipped with a magnetic stir bar and under inert atmosphere ($N_2$), a 2.5M solution of the respective 3-oxo-propionic acid ester derivative (1.0 eq.) in glacial acetic acid was cooled to 10° C. and at this temperature was added a 8.2M solution of $NaNO_2$ (1.16 eq.) in water. After the addition was complete (15 min), the solution was allowed to warm to rt and stirred for 2 h. The solution was then poured into water (5.3 times the volume of glacial acetic acid) and after a few minutes crystals begun to appear. This suspension was cooled with an ice-bath and crystals were collected by filtration. The cake was washed several times with cold water and the water was removed by azeotrope distillation with toluene under reduced pressure to give the respective 2-hydroxyimino-3-oxo-propionic acid ester derivative, which was dissolved in a 1:1.3 mixture of acetic anhydride and glacial acetic acid (0.66 mL for 1.0 mmol of the respective 3-oxo-propionic acid ester derivative). To this solution was added sodium acetate (0.06 eq.) and $HgCl_2$ (0.002 eq.). The mixture was refluxed for 1 h, then cooled to rt and filtered. The solid was rinsed with ether, the organic filtrate was recovered, washed 3 times with water and once with 1M aq. $K_2CO_3$. The organic layer was dried over $MgSO_4$, filtered and the solvent was removed under reduced pressure. The crude product was purified by FC to afford the desired 2-acetylamino-3-oxo-propionic acid ester derivative.

General Procedure G: Cyclization (1)

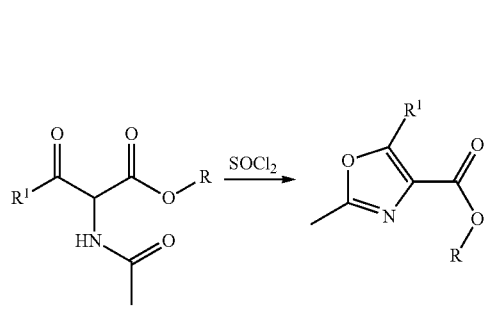

In a flame dried round-bottomed flask equipped with a magnetic stir bar and under inert atmosphere ($N_2$), a 1.6M solution of the respective 2-acetylamino-3-oxo-propionic acid ester derivative (1.0 eq.) in chloroform was cooled to about 0° C. in an ice/NaCl bath. $SOCl_2$ (1.4 eq.) was added to the stirred solution and the temperature was maintained at about 0° C. for 30 minutes. Then the solution was stirred at reflux for one hour. Another 0.25 eq. of $SOCl_2$ was added and the reaction mixture was refluxed for an additional hour. The excess $SOCl_2$ was quenched with 1M aq. $K_2CO_3$. The aq. layer was extracted twice with ether. The combined organic phases were washed once with water and dried over $MgSO_4$, filtered and the solvent was removed under reduced pressure to afford the desired oxazole derivative.

General Procedure H: Cyclization (2)

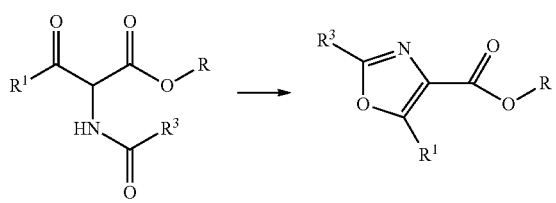

In a flame dried round-bottomed flask equipped with a magnetic stir bar and under an inert atmosphere ($N_2$), $Et_3N$ (4.1 eq.) followed by a 0.1M solution of the respective 2-(carbonyl-amino)-3-oxo-propionic acid ester derivative (1.0 eq.) in $CH_2Cl_2$ were added to a 0.2M solution of triphenylphosphine (2.0 eq.), and iodine (2.0 eq.) in $CH_2Cl_2$. The reaction mixture was stirred for 1.5 h at rt. The solvent was removed under reduced pressure and the residue purified by FC to afford the desired oxazole derivative.

General Procedure I: N-Insertion

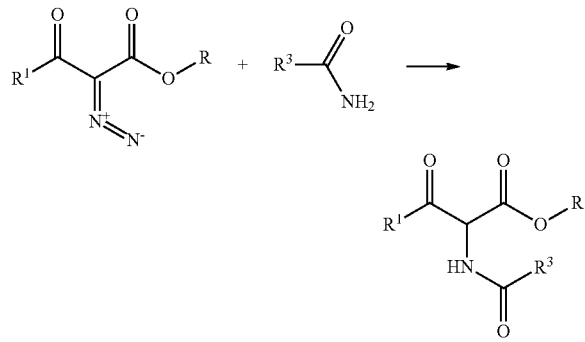

In a flame dried round-bottomed flask equipped with a magnetic stir bar and under an inert atmosphere (N$_2$), a 0.5M solution of the diazo derivative (1.0 eq.) in 1,2-dichloroethane was added over 1.5 h to a refluxing solution of the carboxamide derivative (1.0 eq.) and rhodium(II) acetate (tetrakis(acetato)dirhodium(II)dihydrate, 0.05 eq.) in 1,2-dichloroethane (3 mL per mmol of carboxamide derivative). The reaction mixture was then stirred for 1.5 h at reflux. The solvent was removed under reduced pressure and the residue purified by FC to afford the desired 2-(carbonyl-amino)-3-oxo-propionic acid ester derivative.

General Procedure J: Diazotation

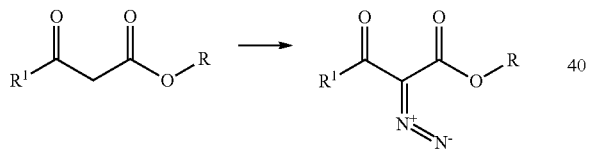

In a flame dried round-bottomed flask equipped with a magnetic stir bar and under an inert atmosphere (N$_2$), a 0.17M solution of the 3-oxo-propionic acid ester derivative (1.0 eq.) in AcCN was treated at 0° C. with 4-acetamidobenzenesulfonyl azide (1.0 eq.) followed by Et$_3$N (3.0 eq.). The reaction mixture was stirred for 1 h at rt. The solvent was removed under reduced pressure, the residue triturated in ether-light petroleum and filtered. The solvent was removed under reduced pressure and the residue was purified by FC to afford the desired diazo derivative.

General Procedure K: Claisen Condensation

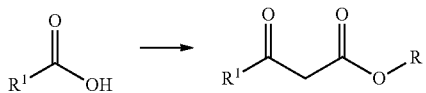

A) In a flame dried round-bottomed flask equipped with a magnetic stir bar and under an inert atmosphere (N$_2$), a 1.3M solution of the acid derivative (1.0 eq.) in 1,2-dichloroethane was treated at rt with a few drops of DMF followed by oxalyl chloride (1.3 eq.). The reaction mixture was stirred for 3 h at rt followed by 20 min at 80° C. The solvent was removed under reduced pressure.

B) In a flame dried round-bottomed flask equipped with a magnetic stir bar and under an inert atmosphere (N$_2$), a 0.83M solution of potassium malonic acid monoethyl ester (2 eq.) in acetonitrile was treated at 10° C. with magnesium chloride (2.5 eq.) and the suspension was stirred at 10° C. for 30 min and at rt for 3 h. The reaction mixture was cooled to 0° C. and treated dropwise over 15 min with the solution of the acid chloride prepared under A, followed by Et$_3$N (2 eq.). The resulting suspension was stirred at rt for 20 h. The solvent was removed under reduced pressure and the residue was striped with toluene. The residue was taken in toluene (1.5 mL per mmol of potassium malonic acid monoethyl ester) and treated at 10° C. with the same amount of 4M HCl as of toluene. The organic layer was washed twice with 4M HCl, water, dried over MgSO$_4$, filtered, and the solvent was removed under reduced pressure. The residue was purified by FC to afford the desired derivative.

General Procedure L: Dioxolane Deprotection

To a glass vial containing a 0.05M solution of the dioxolane in MeOH was added silica gel bound tosic acid (70 mg per 0.05 mmol of dioxolane, R60530B silica gel bound tosic acid from Silicycle) and the reaction mixture was stirred at rt for 18 h. The mixture was filtered. Purification of the residue by FC or HPLC gave the desired compound.

General Procedure M: Cyclization (3)

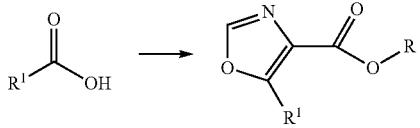

In a flame dried round-bottomed flask equipped with a magnetic stir bar and under an inert atmosphere (N$_2$), a 0.5M solution of the acid (1.0 eq.) in DMF was treated at rt with potassium carbonate sesquihydrate or, alternatively DIPEA (from 1.2 eq. to 1.5 eq.) followed by a 2.0M solution of methyl isocyanoacetate (from 1.5 eq. to 3.2 eq.) in DMF and the mixture was stirred at rt for 5 min. The reaction mixture was cooled to 0° C. and treated with a 0.67M solution of DPPA (1.1 eq.) in DMF. The resulting suspension was stirred at 0° C. for 2 h and at rt for 15 h. It was then poured in a 1:1 mixture of EA and toluene and the organic layer was washed with water, 10% citric acid, water and sat. aq. NaHCO$_3$. The organic layer was dried over MgSO$_4$, filtered, and the solvent was removed under reduced pressure. The residue was purified by FC to afford the desired derivative.

General Procedure N: Cyclization (4)

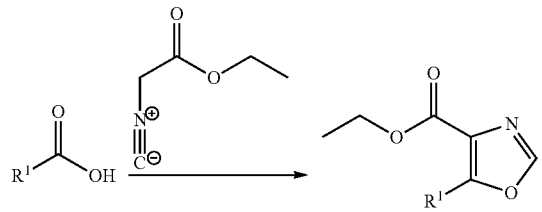

A) In a flame dried round-bottomed flask equipped with a magnetic stir bar and under an inert atmosphere ($N_2$), a 1. M solution of the acid derivative (1.0 eq.) in 1,2-dichloroethane was treated at rt with a few drops of DMF followed by oxalyl chloride (1.3 eq.). The reaction mixture was stirred for 3 h at rt followed by 20 min at 80° C. The solvent was removed under reduced pressure.

B) In a flame dried round-bottomed flask equipped with a magnetic stir bar and under an inert atmosphere ($N_2$), a 0.7M solution of ethyl isocyanoacetate (1 eq.) in THF was treated with DMAP (0.1 eq.) and $Et_3N$ (2.2 eq.) and the reaction mixture was heated to 60° C. before dropwise addition of a THF solution (⅕ of the volume used for the ethyl isocyanoacetate solution) of the acid chloride prepared under A. and the mixture was then stirred at 75° C. for 1.5 h. 25% HCl followed by TBDME were added. The organic layer was washed with sat. aq. $NaHCO_3$, dried over $MgSO_4$, filtered, and the solvent was removed under reduced pressure. The residue was purified by FC to afford the desired derivative.

General Procedure O: Oxazole Opening and N-acetylation

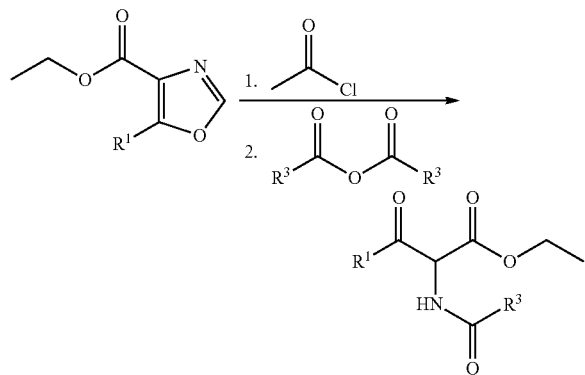

In a flame dried round-bottomed flask equipped with a magnetic stir bar and under an inert atmosphere ($N_2$), a 0.43M solution of the oxazole derivative (1.0 eq.) in EtOH was treated at 0° C. with acetylchloride (9 eq.) while maintaining the temperature below 10° C. The reaction mixture was then stirred overnight at 50° C. The solvent was removed under reduced pressure and the residue was treated at 0° C. with a 1.3M solution of sodium acetate (2 eq) in water. The anhydride (or the corresponding acid chloride) (2 eq.) was then added dropwise. After 30 min, TBDME was added and the organic phase was washed with water, dried over $Na_2SO_4$, filtered, and the solvent was removed under reduced pressure. The residue was purified by FC to afford the desired derivative.

General Procedure P: Cyclization (5)

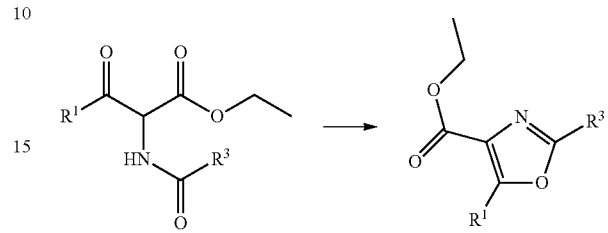

In a flame dried round-bottomed flask equipped with a magnetic stir bar and under an inert atmosphere ($N_2$), a 0.65M solution of the amide in conc. Sulphuric acid was stirred overnight at rt. The reaction mixture was then poured onto ice and extracted several time with 4-methyl-3-pentanone. The combined organic phases were dried over $Na_2SO_4$, filtered, and the solvent was removed under reduced pressure. The residue might be purified by FC to afford the desired derivative.

General Procedure R: Condensation

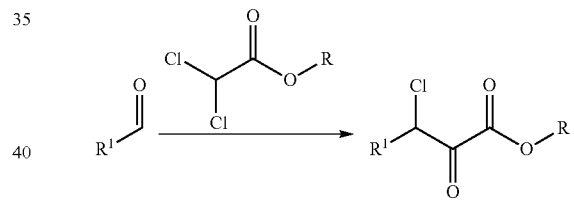

In a flame dried round-bottomed flask equipped with a magnetic stir bar and under inert atmosphere ($N_2$), a solution of the aldehyde derivative (1 eq.) in dichloro-acetic acid methyl ester (1.0 eq.) was added over 1 h to a 1.45M suspension of KOt-Bu (1.0 eq.) in THF at −78° C. The reaction mixture was stirred at −78° C. for 5 h and at rt overnight. The solvent was removed under reduced pressure and the residue was dissolved in EA and washed with water. The organic layer was dried over $MgSO_4$ and concentrated under reduced pressure to afford the corresponding 3-chloro-2-oxo-propionic acid methyl ester derivative.

General Procedure S: Cyclization (6)

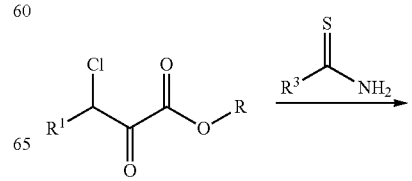

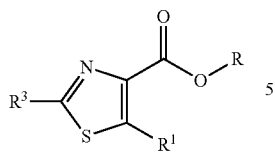

$R^3$ represents $(C_1-C_4)$alkyl or cyclopropyl.

In a flame dried round-bottomed flask equipped with a magnetic stir bar and under inert atmosphere ($N_2$), a 0.5M solution of the respective thioamide (1.0 eq.) in MeCN was added to a 2.2M solution of the respective 3-chloro-2-oxo-propionic acid ester derivative (1.0 eq.) in MeCN along with molecular sieves 4 Å (91 mg per mmol of thioamide). After stirring at rt for 5 h, the mixture was cooled with an ice-bath and the obtained precipitate was filtered off. The residue was washed with cold MeCN, dried, dissolved in MeOH (1.12 times the amount of MeCN as used for the thioamide) and stirred at 50° C. for 6 h. The solvents were removed under reduced pressure to give the corresponding thiazole-4-carboxylic acid ester derivative.

General Procedure T: Cyclization (7)

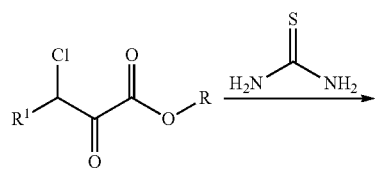

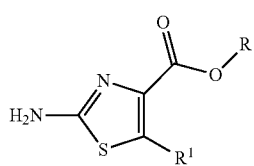

In a flame dried round-bottomed flask equipped with a magnetic stir bar and under an inert atmosphere ($N_2$), a 0.57M solution of the 3-chloro-2-oxo-propionic acid ester derivative (1.0 eq.) in acetone was added to a 0.72M solution of thiourea (1.0 eq.) in acetone. The reaction mixture was stirred overnight at 57° C. The cooled reaction mixture was filtered and the solvent was removed under reduced pressure. The residue was dissolved in water to obtain a 0.2M solution, which was treated with sat. aq. $NaHCO_3$ until pH 7 was reached. The mixture was then extracted with ether, organic layers were combined, dried over $MgSO_4$ and the solvent was removed under reduced pressure to afford the desired 2-amino-thiazole derivative.

General Procedure U: Sandmeyer Reaction

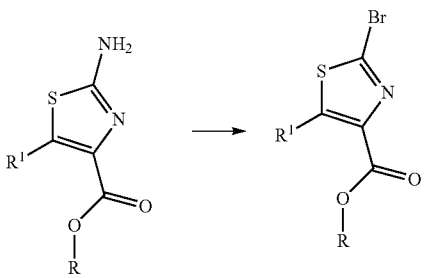

In a flame dried round-bottomed flask equipped with a magnetic stir bar and under an inert atmosphere ($N_2$) atmosphere, a 0.18M solution of $CuBr_2$ (0.97 eq.) in AcCN was carefully treated with isoamylnitrite (1.45 eq.) at 5° C. The reaction mixture was stirred for 30 min and the 2-amino-thiazole-4-carboxylic acid ester derivative (0.86 eq.) was then added portionwise. The resulting mixture was stirred at rt for 15 min, then at 40° C. for 30 min and at 65° C. for 1 h. The solvent was removed under reduced pressure and the residue was purified by FC to afford the desired bromo derivative.

General Procedure V: Dehalogenation

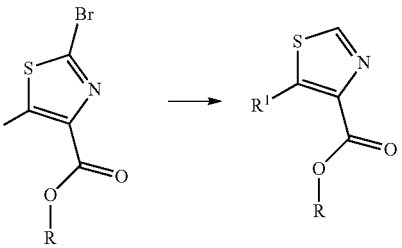

In a flame dried round-bottomed flask equipped with a magnetic stir bar and under an $H_2$ atmosphere, a 0.16M solution of the bromide (1.0 eq.), in EtOH was reduced with Pd/C (10% Pd, 200 mg for 1 mmol of the bromide). The reaction mixture was filtered over Celite and the solvent was removed under reduced pressure to afford the desired reduced derivative.

Synthesis of Intermediates

6-Oxo-heptanoic acid methyl ester

In a flame dried round-bottomed flask under inert atmosphere ($N_2$), a solution of 5-acetylvaleric acid (7.54 g, 50.21 mmol) in a mixture of $CH_2Cl_2$ (35 mL) and MeOH (14 mL) was treated with conc. $H_2SO_4$ (0.14 mL, 2.51 mmol) and the reaction mixture was stirred at reflux for 24 h. The mixture was cooled to rt and sat. aq. $Na_2CO_3$ was added. The aq. layer was extracted with $CH_2Cl_2$ and the combined organic layers were washed with water, dried over $Na_2SO_4$, filtered, and the solvents were removed under reduced pressure. Purification of the residue by FC (50:1→1:2 hept-EA) gave the title compound as an orange oil.

5-(2-Methyl-[1,3]dioxolan-2-yl)-pentanoic acid methyl ester

In a flame dried round-bottomed flask equipped with a magnetic stir bar and under inert atmosphere ($N_2$), a solution of 6-oxo-heptanoic acid methyl ester (7.96 g, 50.32 mmol) in ethylene glycol (55.0 mL) was treated with trimethylorthoformate (10.65 mL, 110.14 mmol) followed by $LiBF_4$ (963 mg, 10.06 mmol). The reaction mixture was heated at 95° C. for 14 h. The reaction mixture was cooled to rt and partitioned between EA and sat. aq. $NaHCO_3$ The layers were separated and the aq. layer extracted with EA. The combined org. extracts were washed with sat. aq. $NaHCO_3$, dried over $Na_2SO_4$, filtered, and the solvent was removed under reduced pressure. Purification of the residue by FC (50:1→2:1 hept-EA) gave the title compound as a dark yellow oil. TLC: rf (3:1 hept-EA)=0.30.

5-(2-Methyl-[1,3]dioxolan-2-yl)-pentanoic acid

In a flame dried round-bottomed flask equipped with a magnetic stir bar and under inert atmosphere ($N_2$), a solution of 5-(2-methyl-[1,3]dioxolan-2-yl)-pentanoic acid methyl ester (5.43 g, 26.85 mmol) in a mixture of THF (70 mL) and water (70 mL) was treated at rt with lithium hydroxide monohydrate (1.45 g, 34.55 mmol) and the mixture was stirred for 3 h at rt. The THF was removed under reduced pressure and the aqueous phase was washed with EA, concentrated under reduced pressure and poured in cold sat. aq. $NH_4Cl$. The pH was adjusted to 4-5 using 1N HCl and the aqueous phase was extracted with EA (3×). The combined org. extracts were dried over $Na_2SO_4$, filtered, and the solvent was removed under reduced pressure. Purification of the residue by FC (20:1→1:2 hept-EA) gave the title compound as a white solid. LC-MS-conditions 02: $t_R$=0.68 min [M+H]$^+$=189.52.

3-Hydroxy-2-[5-(2-methyl-[1,3]dioxolan-2-yl)-pentanoylamino]-propionic acid methyl ester In a flame dried round-bottomed flask equipped with a magnetic stir bar and under inert atmosphere ($N_2$), a solution of 5-(2-methyl-[1,3]dioxolan-2-yl)-pentanoic acid (4.78 g, 25.40 mmol) in THF (165 mL) at −30° C. was treated sequentially with $Et_3N$ (7.50 mL, 53.33 mmol) followed by isobutyl chloroformate (3.81 mL, 27.94 mmol). After stirring for 1 h at −30° C., serine methylester hydrochloride (4.43 g, 37.94 mmol) was added and the reaction mixture was allowed to warm gradually to rt over 3 h and stirred for an additional 16 h at rt. The resulting suspension was filtered, the solid washed with THF and the filtrate was concentrated under reduced pressure. Purification of the residue by FC (9:1:0→0:9:1 hept-EA-MeOH) gave the title compound as a colorless oil. TLC: rf (1000:50:4 $CH_2Cl_2$-MeOH—$NH_3$)=0.1. LC-MS-conditions 02: $t_R$=0.63 min [M+H]$^+$=290.25.

2-[4-(2-Methyl-[1,3]dioxolan-2-yl)-butyl]-4,5-dihydro-oxazole-4-carboxylic acid methyl ester In a flame dried round-bottomed flask equipped with a magnetic stir bar and under inert atmosphere ($N_2$), a solution of 3-hydroxy-2-[5-(2-methyl-[1,3]dioxolan-2-yl)-pentanoylamino]-propionic acid methyl ester (1.40 g, 4.84 mmol) in dry THF (15 mL) was added at −10° C. to a solution of (methoxycarbonylsulfamoyl)triethylammonium hydroxide (1.43 g, 5.81 mmol) in dry THF (35 mL) and the resulting suspension was stirred at 0° C. for 1.5 h. The reaction mixture was then stirred at reflux overnight. The mixture was then allowed to cool down to rt and filtered. The filtrate was concentrated under reduced pressure to give the title compound as a pale yellow oil. TLC: rf (1000:50:4 $CH_2Cl_2$-MeOH—$NH_3$)=0.45.

2-[4-(2-Methyl-[1,3]dioxolan-2-yl)-butyl]-oxazole-4-carboxylic acid methyl ester In a flame dried round-bottomed flask equipped with a magnetic stir bar and under inert atmosphere ($N_2$), a solution of 2-[4-(2-methyl-[1,3]dioxolan-2-yl)-butyl]-4,5-dihydro-oxazole-4-carboxylic acid methyl ester (1.04 g, 3.83 mmol) in $CH_2Cl_2$ (30 mL) at 0° C. was treated with DBU (0.72 mL, 4.79 mmol). Then, bromotrichloromethane (0.95 mL, 9.58 mmol) was added dropwise over 20 min and the reaction mixture was stirred at 0° C. for 4 h then at rt overnight. Additional DBU (0.72 mL, 4.79 mmol) and bromotrichloromethane (0.95 mL, 9.58 mmol) were added at 0° C. and the reaction mixture stirred at rt for 24 h. Sat. aq. $NaHCO_3$ was then added and the aq. phase was extracted with $CH_2Cl_2$ (3×). The combined org. extracts were dried over $Na_2SO_4$, filtered, and the solvent was removed under reduced pressure. Purification of the residue by FC (20:1→1:1 hept-EA) gave the title compound as a white solid. TLC: rf (1000:50:4 $CH_2Cl_2$-MeOH—$NH_3$)=0.25. LC-MS-conditions 02: $t_R$=0.84 min [M+H]$^+$=270.35.

2-[4-(2-Methyl-[1,3]dioxolan-2-yl)-butyl]-oxazole-4-carboxylic acid

In a flame dried round-bottomed flask equipped with a magnetic stir bar and under inert atmosphere ($N_2$), a solution of 2-[4-(2-methyl-[1,3]dioxolan-2-yl)-butyl]-oxazole-4-carboxylic acid methyl ester (713 mg, 2.65 mmol) in THF (15 mL) was treated at rt with 1N NaOH (6.7 mL, 6.70 mmol) and the reaction mixture was stirred for 1 h at rt. The solvents were removed under reduced pressure. The residue was treated with sat. aq. $NH_4Cl$, and acidified to pH 4-5 with 1N HCl. The aq. layer was extracted with $CH_2Cl_2$ and the combined org. extracts were dried over $Na_2SO_4$, filtered, and the solvent was removed under reduced pressure to give the title compound as a white solid. TLC: rf (4:1 $CH_2Cl_2$-MeOH)=0.5. LC-MS-conditions 02: $t_R$=0.75 min [M+H]$^+$=256.31.

2-[4-(2-Methyl-[1,3]dioxolan-2-yl)-butyl]-oxazole-4-carbonyl azide

In a flame dried round-bottomed flask equipped with a magnetic stir bar and under inert atmosphere ($N_2$), a suspension of 2-[4-(2-methyl-[1,3]dioxolan-2-yl)-butyl]-oxazole-4-carboxylic acid (489 mg, 1.92 mmol) in toluene (20 mL) was treated with a drop of DMF followed by oxalyl chloride (0.20 mL, 2.30 mmol) and the resulting yellow solution was stirred at rt for 1 h. The solvent was then removed under reduced pressure (coevaporation with toluene) to give 2-[4-(2-methyl-[1,3]dioxolan-2-yl)-butyl]-oxazole-4-carbonyl chloride as a yellow oil. LC-MS-conditions 02: $t_R$=0.96 min [M+H]$^+$=274.37.

In a flame dried round-bottomed flask equipped with a magnetic stir bar and under inert atmosphere ($N_2$), this crude 2-[4-(2-methyl-[1,3]dioxolan-2-yl)-butyl]-oxazole-4-carbonyl chloride was dissolved in acetone (18.0 mL). The solution was cooled to 0° C. and a solution of sodium azide (314 mg, 4.79 mmol) in H$_2$O (2.0 mL) was added over 1 h. The reaction mixture was stirred at 0° C. for 1.5 h then at rt for 45 min. The mixture was concentrated under reduced pressure (coevaporation with toluene) then dissolved in CH$_2$Cl$_2$ and filtered. The filtrate was concentrated under reduced pressure to give the title compound as a yellow oil. LC-MS-conditions 02: t$_R$=0.89 min [M+H]$^+$=281.38.

{2-[4-(2-Methyl-[1,3]dioxolan-2-yl)-butyl]-oxazol-4-yl}-carbamic acid 2-chloro-benzyl ester In a flame dried round-bottomed flask equipped with a magnetic stir bar and under inert atmosphere (N$_2$), a solution of 2-[4-(2-methyl-[1,3]dioxolan-2-yl)-butyl]-oxazole-4-carbonyl azide (28 mg, 0.10 mmol) in xylene (0.5 mL) was heated to 140° C. for 5 min. 2-Chlorobenzyl alcohol (0.10 mL, 1.07 mmol) was then added and the reaction mixture was further stirred at 140° C. for 5 min. The solvent was removed under reduced pressure. Purification of the residue by FC (20:1→1:1 hept-EA) gave the title compound as a pale yellow solid. TLC: rf (1:1 hept-EA)=0.60. LC-MS-conditions 02: t$_R$=1.05 min [M+H]$^+$=395.36.

3-Hydroxy-2-(6-oxo-heptanoylamino)-propionic acid methyl ester

In a flame dried round-bottomed flask equipped with a magnetic stir bar and under inert atmosphere (N$_2$), a solution of commercially available 6-oxo-heptanoic acid (2.00 g, 13.32 mmol) in THF (82 mL) at −30° C. was treated sequentially with Et$_3$N (3.89 mL, 27.97 mmol) followed by isobutyl chloroformate (1.95 mL, 14.65 mmol). After stirring for 1 h at −30° C., serine methylester hydrochloride (2.32 g, 14.65 mmol was added and the reaction mixture was allowed to warm gradually to rt and stirred for an additional 2 h at rt. The resulting suspension was filtered, the solid washed with THF and the filtrate was concentrated under reduced pressure. Purification of the residue by FC (97:3 EA-MeOH) gave the title compound as a colorless oil. TLC: rf (97:3 EA-MeOH)=0.26. LC-MS-conditions 02: t$_R$=0.56 min [M+H]$^+$=246.44.

2-(5-Oxo-hexyl)-4,5-dihydro-oxazole-4-carboxylic acid methyl ester

In a flame dried round-bottomed flask equipped with a magnetic stir bar and under inert atmosphere (N$_2$), a solution of 3-hydroxy-2-(6-oxo-heptanoylamino)-propionic acid methyl ester (1.50 g, 6.12 mmol) in dry and degassed THF (24 mL) was added at −10° C. to a solution of (methoxycarbonylsulfamoyl)triethylammonium hydroxide (1.79 g, 7.31 mmol) in dry and degassed THF (24 mL) and the resulting suspension was stirred at 0° C. for 1.5 h. The reaction mixture was then stirred at reflux for 1 h. The mixture was then allowed to cool down to rt and filtered and the solvent was removed under reduced pressure. Purification of the residue by FC (97:3 EA-MeOH) gave the title compound as a light yellow oil. TLC: rf (97:3 EA-MeOH)=0.37. LC-MS-conditions 02: t$_R$=0.62 min [M+H]$^+$=228.53.

2-(5-Oxo-hexyl)-oxazole-4-carboxylic acid methyl ester

In a flame dried round-bottomed flask equipped with a magnetic stir bar and under inert atmosphere (N$_2$), hexamethylenetetramine (1.45 g, 4.40 mmol) and DBU (1.54 mL, 10.20 mmol) were added to a stirred suspension of copper (II) bromide (2.28 g, 10.20 mmol) in deoxygenated dry CH$_2$Cl$_2$ (30 mL). After 20 min, a deoxygenated solution of 2-(5-oxo-hexyl)-4,5-dihydro-oxazole-4-carboxylic acid methyl ester (931 mg, 4.10 mmol) in CH$_2$Cl$_2$ (11 mL) was added and the reaction mixture was stirred at rt for 2 h. The solvent was removed under reduced pressure and the residue was partitioned between EA (50 mL), and 50 mL of a 1:1 mixture of sat. aq. NH$_4$Cl and 25% aq. NH$_4$OH. The aq. layer was extracted with EA (50 mL) and the combined organic layers were washed with 50 mL of a 1:1 mixture of sat. aq. NH$_4$Cl and 25% aq. NH$_4$OH followed by 10% citric acid (50 mL), sat. aq. NaHCO$_3$ (50 mL) and brine (50 mL). The organic phase was dried over MgSO$_4$, filtered, and the solvent was removed under reduced pressure. Purification of the residue by FC (1:4 hept-EA) gave the title compound as a pale yellow oil. TLC: rf (1:4 hept-EA)=0.37. LC-MS-conditions 02: t$_R$=0.78 min, [M+H]$^+$=226.47.

2-(5,5-Difluoro-hexyl)-oxazole-4-carboxylic acid methyl ester

In a flame dried round-bottomed flask equipped with a magnetic stir bar and under inert atmosphere (N$_2$), a solution of 2-(5-oxo-hexyl)-oxazole-4-carboxylic acid methyl ester (410 mg, 1.82 mmol) in toluene (4.0 mL) was treated with bis(2-methoxyethyl)aminosulfur trifluoride (4.24 g, 18.20 mmol) followed by ethanol (0.02 mL) and the mixture was then stirred overnight at 60° C. The reaction mixture was gently poured on sat. aq. Na$_2$CO$_3$ (20 mL) and extracted with EA (2×20 mL). The combined organic layers were washed with sat. aq. Na$_2$CO$_3$ (20 mL) and water (20 mL). The organic phase was dried over MgSO$_4$, filtered, and the solvent was removed under reduced pressure. Purification of the residue by FC (6:4 hept-EA) gave the title compound as a yellow oil. TLC: rf (6:4 hept-EA)=0.31. LC-MS-conditions 02: t$_R$=0.95 min, [M+H]$^+$=248.28.

2-(5,5-Difluoro-hexyl)-oxazole-4-carboxylic acid

In a flame dried round-bottomed flask equipped with a magnetic stir bar and under inert atmosphere (N$_2$), a solution of 2-(5,5-difluoro-hexyl)-oxazole-4-carboxylic acid methyl ester (320 mg, 1.29 mmol) in THF (13 mL) was treated at rt with 1N NaOH (6.5 mL, 6.5 mmol) and the reaction mixture was stirred for 1.5 h at rt. The reaction mixture was poured in 1N HCl (13 mL) and extracted twice with EA (2×20 mL). The combined org. extracts were dried over MgSO$_4$, filtered, and the solvent was removed under reduced pressure to give the title compound as a brown solid. LC-MS-conditions 02: t$_R$=0.84 min, [M+H]$^+$=234.45.

2-(5,5-Difluoro-hexyl)-oxazole-4-carbonyl azide

In a flame dried round-bottomed flask equipped with a magnetic stir bar and under inert atmosphere (N$_2$), a suspension of 2-(5,5-difluoro-hexyl)-oxazole-4-carboxylic acid (280 mg, 1.20 mmol) in toluene (12 mL) was treated at 0° C. with a drop of DMF followed by oxalyl chloride (0.13 mL, 1.44 mmol) and the resulting yellow solution was stirred at rt for 1 h. The solvent was then removed under reduced pressure (coevaporation with toluene) to give 2-(5,5-difluoro-hexyl)-oxazole-4-carbonyl chloride as a brown oil.

In a flame dried round-bottomed flask equipped with a magnetic stir bar and under inert atmosphere (N$_2$), a solution of this crude 2-(5,5-difluoro-hexyl)-oxazole-4-carbonyl chloride was dissolved in dry acetone (12.0 mL). The solution was cooled to 0° C. and a solution of sodium azide (196 mg, 2.98 mmol) in H$_2$O (1.4 mL) was added dropwise. The reaction mixture was stirred at 0° C. for 45 min. The mixture was concentrated under reduced pressure, and the residue was dissolved in CH$_2$Cl$_2$ and filtered. The filtrate was concentrated under reduced pressure to give the title compound as a brown solid. LC-MS-conditions 02: t$_R$=0.98 min, [M+H]$^+$=259.09.

[2-(5,5-Difluoro-hexyl)-oxazol-4-yl]-carbamic acid tert-butyl ester

In a flame dried round-bottomed flask equipped with a magnetic stir bar and under inert atmosphere (N$_2$), a solution of 2-(5,5-difluoro-hexyl)-oxazole-4-carbonyl azide (185 mg, 0.72 mmol) in xylene (3.0 mL) was heated to 140° C. for 5 min. tert-Butanol (0.67 mL, 7.16 mmol) was then added and the reaction mixture was further stirred at 140° C. for 5 min. The solvent was removed under reduced pressure. Purification of the residue by FC (4:1 hept-EA) gave the title compound as a colorless oil. TLC: rf (4:1 hept-EA)=0.24. LC-MS-conditions 02: t$_R$=1.06 min.

[2-(5,5-Difluoro-hexyl)-oxazol-4-yl]-(2-methyl-5-m-tolyl-oxazole-4-carbonyl)-carbamic acid tert-butyl ester In a flame dried round-bottomed flask equipped with a magnetic stir bar and under inert atmosphere (N$_2$), a suspension of 2-methyl-5-m-tolyl-oxazole-4-carboxylic acid (74 mg, 0.34 mmol) in toluene (2.0 mL) was treated with a drop of DMF followed by oxalyl chloride (0.10 mL, 1.18 mmol) and the resulting yellow solution was stirred at rt for 1 h. The solvent was then removed under reduced pressure (coevaporation with toluene) to give 2-methyl-5-m-tolyl-oxazole-4-carbonyl chloride.

In a flame dried round-bottomed flask equipped with a magnetic stir bar and under inert atmosphere (N$_2$), a solution of [2-(5,5-difluoro-hexyl)-oxazol-4-yl]-carbamic acid tert-butyl ester (74 mg, 0.24 mL) in THF (2.0 mL) was added to a suspension of NaH (26 mg, 0.60 mmol) in THF (0.5 mL) at 0° C. The resulting suspension was stirred at 0° C. for 5 min and at rt for 30 min. It was cooled to 0° C. and treated dropwise with a solution of the above prepared 2-methyl-5-m-tolyl-oxazole-4-carbonyl chloride in THF (1.5 mL). The resulting suspension was stirred for 30 min at 0° C. followed by 2 h at rt. Water was then added and the aq. layer was extracted several time with EA. The combined org. extracts were dried over Na$_2$SO$_4$, filtered, and the solvent was removed under reduced pressure. Purification of the residue by FC (7:3 hept-EA) gave the title compound as a colorless oil. TLC: rf (7:3 hept-EA)=0.18. LC-MS-conditions 02: t$_R$=1.17 min, [M+H]$^+$=504.17.

2-(5-Oxo-hexyl)-oxazole-4-carboxylic acid

In a flame dried round-bottomed flask equipped with a magnetic stir bar and under inert atmosphere (N$_2$), a solution of 2-(5-oxo-hexyl)-oxazole-4-carboxylic acid methyl ester (464 mg, 2.06 mmol) in THF (20 mL) was treated at rt with 1N NaOH (10 mL, 10 mmol) and the reaction mixture was stirred for 1 h at rt. The reaction mixture was poured in 1N HCl (20 mL) and extracted twice with EA (20 mL). The combined org. extracts were dried over MgSO$_4$, filtered, and the solvent was removed under reduced pressure to give the title compound as a white solid. LC-MS-conditions 02: t$_R$=0.68 min.

2-(5-Oxo-hexyl)-oxazole-4-carbonyl azide

In a flame dried round-bottomed flask equipped with a magnetic stir bar and under inert atmosphere (N$_2$), a suspension of 2-(5-oxo-hexyl)-oxazole-4-carboxylic acid (403 mg, 1.91 mmol) in toluene (19 mL) was treated at 0° C. with a drop of DMF followed by oxalyl chloride (0.20 mL, 2.29 mmol) and the resulting yellow solution was stirred at rt for 1 h. The solvent was then removed under reduced pressure (coevaporation with toluene) to give 2-(5-oxo-hexyl)-oxazole-4-carbonyl chloride as a brown oil.

In a flame dried round-bottomed flask equipped with a magnetic stir bar and under inert atmosphere (N$_2$), a solution of this crude 2-(5-oxo-hexyl)-oxazole-4-carbonyl chloride was dissolved in dry acetone (19.0 mL). The solution was cooled to 0° C. and a solution of sodium azide (315 mg, 4.79 mmol) in H$_2$O (2.2 mL) was added dropwise. The reaction mixture was stirred at 0° C. for 1.5 h. The mixture was concentrated under reduced pressure, and the residue was dissolved in CH$_2$Cl$_2$ and filtered. The filtrate was concentrated under reduced pressure to give the title compound as a brown solid. LC-MS-conditions 02: t$_R$=0.82 min.

[2-(5-Oxo-hexyl)-oxazol-4-yl]-carbamic acid tert-butyl ester

In a flame dried round-bottomed flask equipped with a magnetic stir bar and under inert atmosphere (N$_2$), a solution of 2-(5-oxo-hexyl)-oxazole-4-carbonyl azide (443 mg, 1.88 mmol) in xylene (8.0 mL) was heated to 140° C. for 5 min. tert-Butanol (1.76 mL, 18.75 mmol) was then added and the reaction mixture was further stirred at 140° C. for 5 min. The solvent was removed under reduced pressure. Purification of the residue by FC (6:4 hept-EA) gave the title compound as a pale yellow solid. TLC: rf (6:4 hept-EA)=0.30. LC-MS-conditions 02: t$_R$=0.94 min.

[2-(5-Oxo-hexyl)-oxazol-4-yl]-(5-phenyl-oxazole-4-carbonyl)-carbamic acid tert-butyl ester In a flame dried round-bottomed flask equipped with a magnetic stir bar and under inert atmosphere (N$_2$), a suspension of commercially available 5-phenyl-oxazole-4-carboxylic acid (67 mg, 0.35 mmol) in toluene (1.0 mL) was treated with a drop of DMF followed by oxalyl chloride (0.08 mL, 0.91 mmol) and the resulting yellow solution was stirred at rt for 1 h. The solvent was then removed under reduced pressure (co-evaporation with toluene) to give 5-phenyl-oxazole-4-carbonyl chloride as a brown oil.

In a flame dried round-bottomed flask equipped with a magnetic stir bar and under inert atmosphere (N$_2$), a solution of [2-(5-oxo-hexyl)-oxazol-4-yl]-carbamic acid tert-butyl ester (65 mg, 0.23 mL) in THF (2.0 mL) was added to a suspension of NaH (12 mg, 0.28 mmol) in THF (1.0 mL) at 0° C. The resulting suspension was stirred at 0° C. for 5 min and at rt for 30 min. It was cooled to 0° C. and treated dropwise with a solution of the above prepared 5-phenyl-oxazole-4-carbonyl chloride in THF (1.0 mL). The resulting suspension was stirred for 30 min at 0° C. followed by 16 h at rt. Water was then added and the aq. layer was extracted several time with EA. The combined org. extracts were dried over Na$_2$SO$_4$, filtered, and the solvent was removed under reduced pressure. Purification of the residue by FC (4:1→2:1 hept-EA) gave the title compound as a pale yellow oil. TLC: rf (1:1 hept-EA)=0.39. LC-MS-conditions 02: t$_R$=1.06 min, [M+H]$^+$=454.20.

(2-Methyl-5-m-tolyl-oxazole-4-carbonyl)-[2-(5-oxo-hexyl)-oxazol-4-yl]-carbamic acid tert-butyl ester In a flame dried round-bottomed flask equipped with a magnetic stir bar and under inert atmosphere (N$_2$), a suspension of 2-methyl-5-m-tolyl-oxazole-4-carboxylic acid (53 mg, 0.25 mmol) in toluene (1.0 mL) was treated with a drop of DMF followed by oxalyl chloride (0.08 mL, 0.86 mmol) and the resulting yellow solution was stirred at rt for 30 min. The solvent was then removed under reduced pressure (co-evaporation with toluene) to give 2-methyl-5-m-tolyl-oxazole-4-carbonyl chloride.

In a flame dried round-bottomed flask equipped with a magnetic stir bar and under inert atmosphere ($N_2$), a solution of [2-(5-oxo-hexyl)-oxazol-4-yl]-carbamic acid tert-butyl ester (50 mg, 0.18 mL) in THF (1.0 mL) was added to a suspension of NaH (19 mg, 0.43 mmol) in THF (0.5 mL) at 0° C. The resulting suspension was stirred at 0° C. for 5 min and at rt for 30 min. It was cooled to 0° C. and treated dropwise with a solution of the above prepared 2-methyl-5-m-tolyl-oxazole-4-carbonyl chloride in THF (1.0 mL). The resulting suspension was stirred for 30 min at 0° C. followed by 2 h at rt. Water was then added and the aq. layer was extracted several time with EA. The combined org. extracts were dried over $Na_2SO_4$, filtered, and the solvent was removed under reduced pressure. Purification of the residue by FC (1:1 hept-EA) gave the title compound as a pale yellow oil. TLC: rf (1:1 hept-EA)=0.32. LC-MS-conditions 02: $t_R$=1.10 min, $[M+H]^+$= 482.06.

[5-(3-Fluoro-phenyl)-thiazole-4-carbonyl]-[2-(5-oxo-hexyl)-oxazol-4-yl]-carbamic acid tert-butyl ester In a flame dried round-bottomed flask equipped with a magnetic stir bar and under inert atmosphere ($N_2$), a suspension of 5-(3-fluoro-phenyl)-thiazole-4-carboxylic acid (55 mg, 0.25 mmol) in toluene (1.0 mL) was treated with a drop of DMF followed by oxalyl chloride (0.08 mL, 0.86 mmol) and the resulting yellow solution was stirred at rt for 30 min. The solvent was then removed under reduced pressure (co-evaporation with toluene) to give 5-(3-fluoro-phenyl)-thiazole-4-carbonyl chloride.

In a flame dried round-bottomed flask equipped with a magnetic stir bar and under inert atmosphere ($N_2$), a solution of [2-(5-oxo-hexyl)-oxazol-4-yl]-carbamic acid tert-butyl ester (50 mg, 0.18 mL) in THF (1.0 mL) was added to a suspension of NaH (19 mg, 0.43 mmol) in THF (0.5 mL) at 0° C. The resulting suspension was stirred at 0° C. for 5 min and at rt for 30 min. It was cooled to 0° C. and treated dropwise with a solution of the above prepared 5-(3-fluoro-phenyl)-thiazole-4-carbonyl chloride in THF (1.0 mL). The resulting suspension was stirred for 30 min at 0° C. followed by 2 h at rt. Water was then added and the aq. layer was extracted several time with EA. The combined org. extracts were dried over $Na_2SO_4$, filtered, and the solvent was removed under reduced pressure. Purification of the residue by FC (6:4 hept-EA) gave the title compound as a yellow oil. TLC: rf (6:4 hept-EA)=0.20. LC-MS-conditions 02: $t_R$=1.06 min, $[M+H]^+$= 487.91.

[5-(4-Fluoro-phenyl)-oxazole-4-carbonyl]-[2-(5-oxo-hexyl)-oxazol-4-yl]-carbamic acid tert-butyl ester In a flame dried round-bottomed flask equipped with a magnetic stir bar and under inert atmosphere ($N_2$), a suspension of 5-(4-fluoro-phenyl)-oxazole-4-carboxylic acid (51 mg, 0.25 mmol) in toluene (1.0 mL) was treated with a drop of DMF followed by oxalyl chloride (0.08 mL, 0.86 mmol) and the resulting yellow solution was stirred at rt for 30 min. The solvent was then removed under reduced pressure (co-evaporation with toluene) to give 5-(4-fluoro-phenyl)-oxazole-4-carbonyl chloride.

In a flame dried round-bottomed flask equipped with a magnetic stir bar and under inert atmosphere ($N_2$), a solution of [2-(5-oxo-hexyl)-oxazol-4-yl]-carbamic acid tert-butyl ester (50 mg, 0.18 mL) in THF (1.0 mL) was added to a suspension of NaH (19 mg, 0.43 mmol) in THF (0.5 mL) at 0° C. The resulting suspension was stirred at 0° C. for 5 min and at rt for 30 min. It was cooled to 0° C. and treated dropwise with a solution of the above prepared 5-(4-fluoro-phenyl)-oxazole-4-carbonyl chloride in THF (1.0 mL). The resulting suspension was stirred for 30 min at 0° C. followed by 16 h at rt. Water was then added and the aq. layer was extracted several time with EA. The combined org. extracts were dried over $Na_2SO_4$, filtered, and the solvent was removed under reduced pressure. Purification of the residue by FC (6:4 hept-EA) gave the title compound as a yellow oil. TLC: rf (6:4 hept-EA)=0.21. LC-MS-conditions 02: $t_R$=1.07 min, $[M+H]^+$= 472.48.

(2-Ethyl-5-phenyl-oxazole-4-carbonyl)-[2-(5-oxo-hexyl)-oxazol-4-yl]-carbamic acid tert-butyl ester In a flame dried round-bottomed flask equipped with a magnetic stir bar and under inert atmosphere ($N_2$), a suspension of 2-ethyl-5-phenyl-oxazole-4-carboxylic acid (54 mg, 0.25 mmol) in toluene (1.0 mL) was treated with a drop of DMF followed by oxalyl chloride (0.08 mL, 0.86 mmol) and the resulting yellow solution was stirred at rt for 30 min. The solvent was then removed under reduced pressure (coevaporation with toluene) to give 2-ethyl-5-phenyl-oxazole-4-carbonyl chloride.

In a flame dried round-bottomed flask equipped with a magnetic stir bar and under inert atmosphere ($N_2$), a solution of [2-(5-oxo-hexyl)-oxazol-4-yl]-carbamic acid tert-butyl ester (50 mg, 0.18 mL) in THF (1.0 mL) was added to a suspension of NaH (19 mg, 0.43 mmol) in THF (0.5 mL) at 0° C. The resulting suspension was stirred at 0° C. for 5 min and at rt for 30 min. It was cooled to 0° C. and treated dropwise with a solution of the above prepared 2-ethyl-5-phenyl-oxazole-4-carbonyl chloride in THF (1.0 mL). The resulting suspension was stirred for 30 min at 0° C. followed by 16 h at rt. Water was then added and the aq. layer was extracted several time with EA. The combined org. extracts were dried over $Na_2SO_4$, filtered, and the solvent was removed under reduced pressure. Purification of the residue by FC (6:4 hept-EA) gave the title compound as a yellow oil. TLC: rf (6:4 hept-EA)=0.25. LC-MS-conditions 02: $t_R$=1.11 min, $[M+H]^+$= 482.83.

(E)-2-Styryl-oxazole-4-carboxylic acid ethyl ester

In a flame dried round-bottomed flask equipped with a magnetic stir bar and under inert atmosphere ($N_2$), a suspension of 3-phenyl-acrylamide (10.31 g, 67.95 mmol) and $NaHCO_3$ (28.47 g, 339.73 mmol) in THF (260 mL) was treated with 3-bromo-2-oxo-propionic acid ethyl ester (13.04 mL, 88.33 mmol) and the reaction mixture was heated at reflux for 15 h. 3-Bromo-2-oxo-propionic acid ethyl ester (13.04 mL, 88.33 mmol) was added again and the reaction mixture was stirred at reflux for 15 h. The reaction mixture was then filtered over celite and the solvents were evaporated under reduced pressure. The residue was dissolved in THF (30 mL) and treated at 0° C., dropwise, with trifluoroacetic anhydride (30.0 mL, 215.83 mmol). The reaction mixture was then stirred at rt overnight. Sat. aq. $Na_2CO_3$ was added and the mixture was extracted with EA (3×150 mL), dried over MgSO$_4$, filtered, and the solvent was removed under reduced pressure. Purification of the residue by FC (1:9 EA-Hept) gave the title compound as a yellow solid. TLC: rf (1:9 EA-Hept)=0.1. LC-MS-conditions 02: $t_R$=1.01 min; [M+H]$^+$=244.48.

2-Formyl-oxazole-4-carboxylic acid ethyl ester

In a flame dried round-bottomed flask equipped with a magnetic stir bar and under inert atmosphere (N$_2$), a solution of NaIO4 (3.21 g, 15.00 mmol) in water (26.0) mL was slowly added to a vigorously stirred suspension of silica gel (15.0 g) in acetone (60.0 mL). The mixture was then concentrated under reduced pressure and the lumpy solid slurred in CH$_2$Cl$_2$ and the solvent was evaporated under reduced pressure. CH$_2$Cl$_2$ (40.0 mL) was added and the reaction mixture was treated at rt with (E)-2-styryl-oxazole-4-carboxylic acid ethyl ester (1.22 g, 5.00 mmol) and RuCl$_3$ hydrate (82 mg, 0.15 mmol). The reaction mixture was stirred at rt in the dark for 30 min, filtered and concentrated under reduced pressure. Purification of the residue by FC (1:9 to 1:2 EA-Hept) gave the title compound as a yellow solid. TLC: rf (3:2 EA-Hept)=0.21. LC-MS-conditions 02: $t_R$=0.51 min; [M+H$_2$O+H]$^+$=188.50.

2-Hydroxymethyl-oxazole-4-carboxylic acid ethyl ester

In a flame dried round-bottomed flask equipped with a magnetic stir bar and under inert atmosphere (N$_2$), 2-formyl-oxazole-4-carboxylic acid ethyl ester (272 mg, 1.61 mmol) was dissolved in EtOH (5.0 mL). NaBH$_4$ (112 mg, 2.84 mmol) was added portionwise at 0° C. and the reaction mixture stirred at 0° C. for 1 h. Sat. aq. NH$_4$Cl was added and the mixture extracted with EA (5×10 mL). The combined org. extracts were dried over Na$_2$SO$_4$, filtered, and the solvents were removed under reduced pressure to give the title compound as a yellow oil. TLC: rf (EA)=0.50. LC-MS-conditions 02: $t_R$=0.58 min; [M+H]$^+$=172.03.

2-Methanesulfonyloxymethyl-oxazole-4-carboxylic acid ethyl ester

In a flame dried round-bottomed flask equipped with a magnetic stir bar and under inert atmosphere (N$_2$), a solution of 2-hydroxymethyl-oxazole-4-carboxylic acid ethyl ester (345 mg, 2.02 mmol) in dry CH$_2$Cl$_2$ (10 mL) was treated at 0° C. with Et$_3$N (0.40 mL, 2.87 mmol) followed by DMAP (25 mg, 0.20 mmol) and Ms-Cl (0.20 mL, 2.60 mmol). After stirring at 0° C. for 2 h, the reaction was quenched with water (5 mL). The org. layer was dried over Na$_2$SO$_4$, filtered, and the solvents were removed under reduced pressure. Purification of the residue by FC (1:2→1:1 EA-Hept) gave the title compound as a yellow solid. TLC: rf (1:1 EA-Hept)=0.23. LC-MS-conditions 01: $t_R$=0.73 min; [M+H]$^+$=249.94.

2-(3-Acetyl-pyrazol-1-ylmethyl)-oxazole-4-carboxylic acid ethyl ester

In a flame dried round-bottomed flask equipped with a magnetic stir bar and under inert atmosphere (N$_2$), a solution of 2-methanesulfonyloxymethyl-oxazole-4-carboxylic acid ethyl ester (160 mg, 0.64 mmol) and TBAB (41 mg, 0.13 mmol) in dry acetone (9.0 mL) was treated at rt with a solution of 1-(1H-pyrazol-5-yl)ethan-1-one hydrochloride (99 mg, 0.64 mmol) and K$_2$CO$_3$ (448 mg, 3.21 mmol) in acetone (4.0 mL). After stirring at rt for 2 days, the solvent was removed under reduced pressure. The residue was partitioned between water and EA, the two layers were separated and the aq. layer was extracted twice with EA. The combined org. extracts were dried over Na$_2$SO$_4$, filtered, and the solvent was removed under reduced pressure. Purification of the residue by FC (2:1 hept-EA) gave the title compound as a pale yellow oil. TLC: rf (1:2 hept-EA)=0.33. LC-MS-conditions 02: $t_R$=0.80 min, [M+H]$^+$=263.97.

2-(4-Bromo-pyrazol-1-ylmethyl)-oxazole-4-carboxylic acid ethyl ester

In a flame dried round-bottomed flask equipped with a magnetic stir bar and under inert atmosphere (N$_2$), K$_2$CO$_3$ (356 mg, 2.55 mmol) was added at rt to a solution of 2-methanesulfonyloxymethyl-oxazole-4-carboxylic acid ethyl ester (127 mg, 0.51 mmol), TBAB (33 mg, 0.10 mmol) and 4-bromo-1H-pyrazole (76 mg, 0.51 mmol) in acetone (5.0 mL). After stirring at rt for 2 h, the solvent was removed under reduced pressure. The residue was partitioned between water and EA, the two layers were separated and the aq. layer was extracted twice with EA. The combined org. extracts were dried over Na$_2$SO$_4$, filtered, and the solvent was removed under reduced pressure to give the title compound as an orange solid. TLC: rf (1:1 hept-EA)=0.27. LC-MS-conditions 01: $t_R$=0.84 min, [M+H]$^+$=299.96.

2-(3-Acetyl-pyrazol-1-ylmethyl)-oxazole-4-carbonyl azide

In a flame dried round-bottomed flask equipped with a magnetic stir bar and under inert atmosphere (N$_2$), a solution of 2-(3-acetyl-pyrazol-1-ylmethyl)-oxazole-4-carboxylic acid ethyl ester (137 mg, 0.52 mmol) in THF (5.0 mL) was treated at rt with 1N NaOH (2.5 mL, 2.5 mmol) and the reaction mixture was stirred for 3 h at rt. The reaction mixture was poured in 1N HCl (23 mL) and extracted with EA (50 mL). The org. extracts were dried over MgSO$_4$, filtered, and the solvent was removed under reduced pressure to give the crude 2-(3-acetyl-pyrazol-1-ylmethyl)-oxazole-4-carboxylic acid as a deep brown foam. LC-MS-conditions 02: $t_R$=0.64 min, [M+H]$^+$=236.13.

In a flame dried round-bottomed flask equipped with a magnetic stir bar and under inert atmosphere (N$_2$), a suspension of the above obtained crude 2-(3-acetyl-pyrazol-1-ylmethyl)-oxazole-4-carboxylic acid in toluene (5.0 mL) was treated at rt with a drop of DMF followed by oxalyl chloride (0.08 mL, 0.94 mmol) and the resulting yellow solution was stirred at rt for 4 h. The solvent was then removed under reduced pressure (coevaporation with toluene) to give crude 2-(3-acetyl-pyrazol-1-ylmethyl)-oxazole-4-carbonyl chloride.

In a flame dried round-bottomed flask equipped with a magnetic stir bar and under inert atmosphere (N$_2$), a solution of the above obtained crude 2-(3-acetyl-pyrazol-1-ylmethyl)-oxazole-4-carbonyl chloride was dissolved in dry acetone (5.0 mL). The solution was cooled to 0° C. and a solution of sodium azide (85 mg, 1.30 mmol) in H$_2$O (0.5 mL) was added dropwise. The reaction mixture was stirred at rt for 30 min. The mixture was concentrated under reduced pressure, and the residue was dissolved in CH$_2$Cl$_2$ and filtered. The filtrate was concentrated under reduced pressure to give the title compound as an orange oil. LC-MS-conditions 02: $t_R$=0.78 min, [M+H]$^+$=261.01.

[2-(3-Acetyl-pyrazol-1-ylmethyl)-oxazol-4-yl]-carbamic acid tert-butyl ester In a flame dried round-bottomed flask equipped with a magnetic stir bar and under inert atmosphere ($N_2$), a solution of 2-(3-acetyl-pyrazol-1-ylmethyl)-oxazole-4-carbonyl azide (165 mg, 0.63 mmol) in xylene (2.0 mL) was heated to 140° C. for 5 min. tert-Butanol (0.60 mL, 6.40 mmol) was then added and the reaction mixture was further stirred at 140° C. for 5 min. The solvent was removed under reduced pressure. Purification of the residue by FC (9:1→2:1 hept-EA) gave the title compound as a pale yellow solid. TLC: rf (1:1 hept-EA)=0.33. LC-MS-conditions 01: $t_R$=0.87 min, $[M+H]^+$=306.99.

[2-(3-Acetyl-pyrazol-1-ylmethyl)-oxazol-4-yl]-(2-cyclopropyl-5-phenyl-thiazole-4-carbonyl)-carbamic acid tert-butyl ester In a flame dried round-bottomed flask equipped with a magnetic stir bar and under inert atmosphere ($N_2$), a suspension of 2-cyclopropyl-5-phenyl-thiazole-4-carboxylic acid (90 mg, 0.37 mmol) in toluene (2.0 mL) was treated with a drop of DMF followed by oxalyl chloride (0.11 mL, 1.25 mmol) and the resulting yellow solution was stirred at rt for 2 h. The solvent was then removed under reduced pressure (coevaporation with toluene) to give 2-cyclopropyl-5-phenyl-thiazole-4-carbonyl chloride.

In a flame dried round-bottomed flask equipped with a magnetic stir bar and under inert atmosphere ($N_2$), a solution of [2-(3-acetyl-pyrazol-1-ylmethyl)-oxazol-4-yl]-carbamic acid tert-butyl ester (76 mg, 0.25 mmol) in THF (1.0 mL) was added to a suspension of NaH (27 mg, 0.61 mmol) in THF (0.5 mL) at 0° C. The resulting suspension was stirred at 0° C. for 5 min and at rt for 30 min. It was cooled to 0° C. and treated dropwise with a solution of the above prepared 2-cyclopropyl-5-phenyl-thiazole-4-carbonyl chloride in THF (1.0 mL). The resulting suspension was stirred for 30 min at 0° C. followed by 16 h at rt. Water was then added and the aq. layer was extracted several time with EA. The combined org. extracts were dried over $Na_2SO_4$, filtered, and the solvent was removed under reduced pressure. Purification of the residue by FC (6:4 hept-EA) gave the title compound as a yellow oil. TLC: rf (6:4 hept-EA)=0.20. LC-MS-conditions 02: $t_R$=1.11 min, $[M+H]^+$=534.30.

2-(4-Bromo-pyrazol-1-ylmethyl)-oxazole-4-carbonyl azide

In a flame dried round-bottomed flask equipped with a magnetic stir bar and under inert atmosphere ($N_2$), a solution of 2-(4-bromo-pyrazol-1-ylmethyl)-oxazole-4-carboxylic acid ethyl ester (153 mg, 0.51 mmol) in THF (5.0 mL) was treated at rt with 1N NaOH (2.5 mL, 2.5 mmol) and the reaction mixture was stirred for 1 h at rt. The reaction mixture was poured in 1N HCl and extracted with EA. The org. extracts were dried over $MgSO_4$, filtered, and the solvent was removed under reduced pressure to give the crude 2-(4-bromo-pyrazol-1-ylmethyl)-oxazole-4-carboxylic acid as a pale yellow solid. LC-MS-conditions 02: $t_R$=0.72 min, $[M+H]^+$=271.89.

In a flame dried round-bottomed flask equipped with a magnetic stir bar and under inert atmosphere ($N_2$), a suspension of the above obtained crude 2-(4-bromo-pyrazol-1-ylmethyl)-oxazole-4-carboxylic acid in toluene (5.0 mL) was treated at rt with a drop of DMF followed by oxalyl chloride (0.08 mL, 0.93 mmol) and the resulting yellow solution was stirred at rt for 3 h. The solvent was then removed under reduced pressure (coevaporation with toluene) to give crude 2-(4-bromo-pyrazol-1-ylmethyl)-oxazole-4-carbonyl chloride.

In a flame dried round-bottomed flask equipped with a magnetic stir bar and under inert atmosphere ($N_2$), a solution of the above obtained crude 2-(4-bromo-pyrazol-1-ylmethyl)-oxazole-4-carbonyl chloride was dissolved in dry acetone (5.0 mL). The solution was cooled to 0° C. and a solution of sodium azide (41 mg, 0.62 mmol) in $H_2O$ (0.5 mL) was added dropwise. The reaction mixture was stirred at rt for 30 min. The mixture was concentrated under reduced pressure, and the residue was dissolved in $CH_2Cl_2$ and filtered. The filtrate was concentrated under reduced pressure to give the title compound as a brown oil. LC-MS-conditions 02: $t_R$=0.86 min.

[5-(2-Methyl-[1,3]dioxolan-2-yl)-thiophen-2-yl]-methanol

In a flame dried round-bottomed flask equipped with a magnetic stir bar and under inert atmosphere ($N_2$), to a solution of commercially available 2-methyl-2-thiophen-2-yl-[1,3]dioxolane (5.00 g, 28.49 mmol) in THF (145.0 mL) at −78° C. was added dropwise N,N,N',N'-tetramethyl-ethylendiamine (4.41 mL, 29.06 mmol) followed by n-BuLi (18.14 mL of a 1.6M solution in hexane, 29.06 mmol), maintaining the temperature at −78° C. The reaction mixture was then stirred for 2 h at −78° C. before DMF (6.74 mL, 87.22 mmol) was added dropwise. The cooling bath was removed and the reaction mixture was stirred for 16 h. The reaction mixture was poured on sat. aq. $NaH_4Cl$ (200 mL) and extracted with EA (2×200 mL). The combined org. extracts were dried over $MgSO_4$, filtered, and the solvent was removed under reduced pressure to give crude 5-(2-methyl-[1,3]dioxolan-2-yl)-thiophene-2-carbaldehyde as an yellow oil. LC-MS-conditions 02: $t_R$=0.87 min; $[M+AcCN]^+$=240.32. The crude material was dissolved, under inert atmosphere ($N_2$) in MeOH (51.2 mL) and treated at 0° C., portionwise, over 20 min, with $NaBH_4$ (1.35 g, 34.19 mmol in five equal portions). The reaction mixture was stirred for 45 min at rt. The reaction mixture was poured on water (90 mL) and the aq. layer was extracted with EA (2×225 mL). The combined org. extracts were dried over $MgSO_4$, filtered, and the solvents were removed under reduced pressure. Purification of the residue by FC (50:50 hept-EA) gave the title compound: TLC: rf (50:50 hept-EA)=0.40. LC-MS-conditions 02: $t_R$=0.73 min; $[M+H]^+$=201.46.

[5-(2-Methyl-[1,3]dioxolan-2-yl)-thiophen-2-yl]-acetonitrile

In a flame dried round-bottomed flask equipped with a magnetic stir bar and under inert atmosphere ($N_2$), a solution of [5-(2-methyl-[1,3]dioxolan-2-yl)-thiophen-2-yl]-methanol (10.00 g, 49.94 mmol) in dry $CH_2Cl_2$ (100 mL) was treated at 0° C. with $Et_3N$ (9.04 mL, 64.92 mmol) followed by DMAP (610 mg, 4.99 mmol) and Ms-Cl (4.65 mL, 59.92 mmol). After stirring at rt for 2 h, the reaction was quenched with water (200 mL). The org. layer was dried over $MgSO_4$, filtered, and the solvents were removed under reduced pressure to give crude 2-(5-chloromethyl-thiophen-2-yl)-2-methyl-[1,3]dioxolane as a yellow oil. In a flame dried round-bottomed flask equipped with a magnetic stir bar and under inert atmosphere ($N_2$), a solution of this crude 2-(5-chloromethyl-thiophen-2-yl)-2-methyl-[1,3]dioxolane in DMSO (400 mL) was treated with sodium cyanide (9.07 g, 185.09 mmol) and the reaction mixture was stirred at 80° C. for 1 h. Water (400 mL) was added to the cooled reaction mixture and the product was extracted with EA (2×500 mL). The combined org. extracts were dried over MgSO$_4$, filtered, and the solvents were removed under reduced pressure. Purification of the residue by FC (60:40 hept-EA) gave the title compound: TLC: rf (60:40 hept-EA)=0.34. LC-MS-conditions 02: $t_R$=0.89 min.

[5-(2-Methyl-[1,3]dioxolan-2-yl)-thiophen-2-yl]-acetic acid

In a flame dried round-bottomed flask equipped with a magnetic stir bar and under inert atmosphere (N$_2$), a solution of [5-(2-methyl-[1,3]dioxolan-2-yl)-thiophen-2-yl]-acetonitrile (2.67 g, 12.77 mmol) in a 1:1 mixture of MeOH and H$_2$O (11 mL) was treated at rt with KOH (1.43 g, 25.54 mmol). After stirring at reflux for 1.5 h, the cooled reaction mixture was washed with ether. The aq. phase was carefully acidified to pH 4-5 with 1M HCl and the product was extracted several times with CH$_2$CL$_2$. The combined org. extracts were dried over Na$_2$SO$_4$, filtered, and the solvents were removed under reduced pressure to give the title compound as a brown oil. LC-MS-conditions 02: $t_R$=0.79 min.

3-Hydroxy-2-{2-[5-(2-methyl-[1,3]dioxolan-2-yl)-thiophen-2-yl]-acetylamino}-propionic acid methyl ester In a flame dried round-bottomed flask equipped with a magnetic stir bar and under inert atmosphere (N$_2$), a solution of [5-(2-methyl-[1,3]dioxolan-2-yl)-thiophen-2-yl]-acetic acid (1.25 g, 5.48 mmol) in CH$_2$Cl$_2$ (20 mL) was treated sequentially with DMAP (135 mg, 1.10 mmol), HOBT (1.07 g, 6.80 mmol), EDC (2.68 g, 13.69 mmol) and DIPEA (3.85 mL, 21.9 mmol). After stirring for 1 h at rt, serine methylester hydrochloride (913 g, 5.75 mmol was added and the reaction mixture stirred for 1 h at rt. Sat. aq. NH$_4$Cl was added and the mixture was extracted twice with CH$_2$Cl$_2$. The combined org. extracts were dried over Na$_2$SO$_4$, filtered, and the solvent was removed under reduced pressure. Purification of the residue by FC (1000:25:2 CH$_2$Cl$_2$-MeOH—NH$_4$OH) gave the title compound as an orange oil. TLC: rf (EA)=0.3. LC-MS-conditions 01: $t_R$=0.68 min; [M+H]$^+$=329.94.

2-[5-(2-Methyl-[1,3]dioxolan-2-yl)-thiophen-2-ylmethyl]-4,5-dihydro-oxazole-4-carboxylic acid methyl ester In a flame dried round-bottomed flask equipped with a magnetic stir bar and under inert atmosphere (N$_2$), a solution of 3-hydroxy-2-{2-[5-(2-methyl-[1,3]dioxolan-2-yl)-thiophen-2-yl]-acetylamino}-propionic acid methyl ester (470 mg, 1.43 mmol) in dry THF (5 mL) was added at 0° C. to solution of (methoxycarbonylsulfamoyl)triethylammonium hydroxide (455 mg, 1.83 mmol) in dry THF (10 mL) and the resulting suspension was stirred at 0° C. for 20 min, followed by 15 min at rt. The reaction mixture was then stirred at reflux for 1 h. The mixture was then allowed to cool down to rt and filtered. The filter cake was rinsed with ether and EA and the filtrate was concentrated under reduced pressure. Purification of the residue by FC (1:1→1:0 EA-Hept) gave the title compound as a yellow oil. TLC: rf (EA)=0.6. LC-MS-conditions 02: $t_R$=0.70 min, [M+H$_2$O+H]$^+$=329.90.

2-[5-(2-Methyl-[1,3]dioxolan-2-yl)-thiophen-2-ylmethyl]-oxazole-4-carboxylic acid methyl ester In a flame dried round-bottomed flask equipped with a magnetic stir bar and under inert atmosphere (N$_2$), hexamethylenetetramine (273 mg, 1.92 mmol) and DBU (0.29 mL, 1.92 mmol) were added to a stirred suspension of copper (II) bromide (429 mg, 1.92 mmol) in deoxygenated dry CH$_2$Cl$_2$ (2.0 mL). After 20 min, a deoxygenated solution of 2-[5-(2-methyl-[1,3]dioxolan-2-yl)-thiophen-2-ylmethyl]-4,5-dihydro-oxazole-4-carboxylic acid methyl ester (240 mg, 0.77 mmol) in CH$_2$Cl$_2$ (5.0 mL) was added and the reaction mixture was stirred at rt for 2 h. The solvent was removed under reduced pressure and the residue was partitioned between EA (60 mL), and 40 mL of a 1:1 mixture of sat. aq. NH$_4$Cl and 25% aq. NH$_4$OH. The aq. layer was extracted with EA (40 mL) and the combined organic layers were washed with 40 mL of a 1:1 mixture of sat. aq. NH$_4$Cl and 25% aq. NH$_4$OH followed by 10% citric acid (40 mL), sat. aq. NaHCO$_3$ (40 mL) and brine (40 mL). The organic phase was dried over MgSO$_4$, filtered, and the solvent was removed under reduced pressure. Purification of the residue by FC (2:1→1:4 hept-EA) gave the title compound as a pale yellow oil. TLC: rf (1:3 hept-EA)=0.40. LC-MS-conditions 01: $t_R$=0.88 min, [M+H]$^+$= 309.98.

2-(5-Acetyl-thiophen-2-ylmethyl)-oxazole-4-carboxylic acid

In a flame dried round-bottomed flask equipped with a magnetic stir bar and under inert atmosphere (N$_2$), a solution of 2-[5-(2-methyl-[1,3]dioxolan-2-yl)-thiophen-2-ylmethyl]-oxazole-4-carboxylic acid methyl ester (570 mg, 1.84 mmol) in THF (20 mL) was treated at rt with 1N NaOH (10 mL, 10.00 mmol) and the reaction mixture was stirred for 1 h at rt. The reaction mixture was poured in 1N HCl (20 mL) and extracted twice with EA (20 mL). The combined org. extracts were dried over MgSO$_4$, filtered, and the solvent was removed under reduced pressure to give the title compound as a brown solid along with 2-[5-(2-methyl-[1,3]dioxolan-2-yl)-thiophen-2-ylmethyl]-oxazole-4-carboxylic acid.

2-(5-Acetyl-thiophen-2-ylmethyl)-oxazole-4-carbonyl azide

In a flame dried round-bottomed flask equipped with a magnetic stir bar and under inert atmosphere (N$_2$), a suspension of the above obtained mixture of 2-(5-acetyl-thiophen-2-ylmethyl)-oxazole-4-carboxylic acid and 2-[5-(2-methyl-[1,3]dioxolan-2-yl)-thiophen-2-ylmethyl]-oxazole-4-carboxylic acid (525 mg) in toluene (17 mL) was treated with a drop of DMF followed by oxalyl chloride (0.19 mL, 2.13 mmol) and the resulting yellow solution was stirred at rt for 2 h. The solvent was then removed under reduced pressure (co-evaporation with toluene) to give a mixture of 2-(5-acetyl-thiophen-2-ylmethyl)-oxazole-4-carbonyl chloride and 2-[5-(2-methyl-[1,3]dioxolan-2-yl)-thiophen-2-ylmethyl]-oxazole-4-carbonyl chloride.

In a flame dried round-bottomed flask equipped with a magnetic stir bar and under inert atmosphere (N$_2$), a solution of this crude mixture of 2-(5-acetyl-thiophen-2-ylmethyl)-oxazole-4-carbonyl chloride and 2-[5-(2-methyl-[1,3]dioxolan-2-yl)-thiophen-2-ylmethyl]-oxazole-4-carbonyl chloride in dry acetone (12.0 mL) was cooled to 0° C. and a solution of sodium azide (262 mg, 3.98 mmol) in H$_2$O (1.4 mL) was added over 1 h. The reaction mixture was stirred at 0° C. for 45 min. The mixture was concentrated under reduced pressure (co-evaporation with toluene) then dissolved in CH$_2$Cl$_2$ and filtered. The filtrated was concentrated under reduced pressure to give the title compound (LC-MS-conditions 01: $t_R$=0.85 min, [M+H]$^+$=276.91) along with 2-[5-(2-methyl-[1,3]dioxolan-2-yl)-thiophen-2-ylmethyl]- oxazole-4-carbonyl azide (LC-MS-conditions 01: $t_R$=0.91 min, [M+H]$^+$=320.92) as a brown solid.

2-(3-Bromo-phenyl)-2-methyl-[1,3]dioxolane

In a flame dried round-bottomed flask equipped with a magnetic stir bar and under inert atmosphere (N$_2$), a solution of 3'-bromoacetophenone (4.67 mL, 33.89 mmol) in ethylene glycol (36.4 mL) was treated with trimethylorthoformate (7.58 mL, 69.14 mmol) followed by LiBF$_4$ (648 mg, 6.78 mmol). The reaction mixture was heated at 95° C. for 3.5 h. The reaction mixture was cooled to rt and partitioned between ether (100 mL) and sat. aq. Na$_2$CO$_3$ (25 mL). The layers were separated and the aq. layer extracted twice with ether (50 mL). The combined org. extracts were dried over Na$_2$SO$_4$, filtered, and the solvent was removed under reduced pressure. Purification of the residue by FC (9:1 hept-EA) gave the title compound as a dark yellow oil. TLC: rf (9:1 hept-EA)=0.44. LC-MS-conditions 02: $t_R$=1.00 min.

[3-(2-Methyl-[1,3]dioxolan-2-yl)-phenyl]-acetic acid ethyl ester

In a flame dried round-bottomed flask equipped with a magnetic stir bar and under inert atmosphere (N$_2$), a suspension of 2-(3-bromo-phenyl)-2-methyl-[1,3]dioxolane (3.620 g, 14.89 mmol), 2-di-t-butylphosphino-2'-methylbiphenyl (931 mg, 2.98 mmol), tri-potassiumphosphate monohydrate (11.063 g, 52.12 mmol) and palladium(II)acetate (334 mg, 1.49 mmol) in toluene (74 mL) was treated with ethyl acetoacetate (2.45 mL, 19.36 mmol). The reaction mixture was heated at 90° C. for 2 h followed by 4 h at 100° C. The reaction mixture was cooled to rt, water (100 mL) was added and the mixture was stirred for 30 min at rt. The org. layers was separated and washed twice with 5% aq. NaCl (50 mL), brine (50 mL) dried over Na$_2$SO$_4$, filtered, and the solvent was removed under reduced pressure. Purification of the residue by FC (4:1 hept-EA) gave the title compound as an orange oil. TLC: rf (4:1 hept-EA)=0.37. LC-MS-conditions 02: $t_R$=0.96 min, [M+H]$^+$=251.21.

[3-(2-Methyl-[1,3]dioxolan-2-yl)-phenyl]-acetic acid

In a flame dried round-bottomed flask equipped with a magnetic stir bar and under inert atmosphere (N$_2$), a solution of [3-(2-methyl-[1,3]dioxolan-2-yl)-phenyl]-acetic acid ethyl ester (3.27 g, 13.07 mmol) in THF (131 mL) was treated at rt with 1N NaOH (64 mL, 64.00 mmol) and the reaction mixture was stirred for 1 h overnight. The reaction mixture was carefully acidified to pH 5-6 with 1N HCl and extracted twice with EA (200 mL). The combined org. extracts were dried over MgSO$_4$, and the solvent was removed under reduced pressure to give the title compound as a brown solid. LC-MS-conditions 02: $t_R$=0.79 min.

[3-(2-Methyl-[1,3]dioxolan-2-yl)-phenyl]-acetic acid tert-butyl ester

In a flame dried round-bottomed flask equipped with a magnetic stir bar and under inert atmosphere (N$_2$), a degassed solution of dicyclohexylamine (1.03 mL, 5.18 mmol) in toluene (30 mL) was treated 0° C. with n-BuLi (2.07 mL of a 2.5M solution in hexane, 5.18 mmol) and the reaction was stirred at 0° C. for 30 min. Acetic acid tert-butyl ester (0.59 mL, 4.40 mmol) was added dropwise and the reaction mixture was stirred at 0° C. for 50 min. To this solution was added a degassed suspension of 2-(3-bromo-phenyl)-2-methyl-[1,3] dioxolane (972 mg, 4.00 mmol) and {[P(t-Bu)$_3$]PdBr}$_2$ (25 mg, 0.03 mmol) and the reaction mixture was stirred at rt for 5 h. The reaction volume was reduced to half by rotary evaporation. The concentrated solution was washed with sat. aq. NH$_4$Cl (30 mL). A large amount of precipitate formed between the aq. and org. layers. The org. layer was separated, and the aq. layer was washed with ether (5×20 mL). The combined org. layers were dried over MgSO$_4$, filtered, and the solvent was removed under reduced. Purification of the residue by FC (9:1 hept-EA) gave the title compound as a yellow oil. TLC: rf (9:1 hept-EA)=0.26. LC-MS-conditions 02: $t_R$=1.05 min.

(3-Acetyl-phenyl)-acetic acid

In a flame dried round-bottomed flask equipped with a magnetic stir bar and under inert atmosphere (N$_2$), a solution of [3-(2-methyl-[1,3]dioxolan-2-yl)-phenyl]-acetic acid tert-butyl ester (268 mg, 0.96 mmol) in TFA (3.89 mL) was stirred for 45 min at rt. The solvent was removed under reduced pressure and the residue was partitioned between CH$_2$Cl$_2$ (25 mL) and 1N NaOH (10 mL). The layers were separated and the aq. layer was acidified with 1N HCl and extracted twice with CH$_2$Cl$_2$ (25 mL). The combined org. layers were dried over Na$_2$SO$_4$, filtered, and the solvent was removed under reduced pressure to give the title compound as a white solid. LC-MS-conditions 02: $t_R$=0.73 min.

3-Hydroxy-2-{2-[3-(2-methyl-[1,3]dioxolan-2-yl)-phenyl]-acetylamino}-propionic acid methyl ester In a flame dried round-bottomed flask equipped with a magnetic stir bar and under inert atmosphere (N$_2$), a solution of [3-(2-methyl-[1,3]dioxolan-2-yl)-phenyl]-acetic acid (2.20 g, 9.90 mmol) in CH$_2$Cl$_2$ (100 mL) was treated sequentially with DMAP (301 mg, 2.47 mmol), HOBT (1.61 g, 11.90 mmol), EDC (4.74 g, 24.75 mmol) and DIPEA (6.78 mL, 39.60 mmol). After stirring for 30 min at rt, serine methylester hydrochloride (1.62 g, 10.39 mmol) was added and the reaction mixture stirred overnight at rt. Water (100 mL) was added and the mixture was extracted twice with CH$_2$Cl$_2$ (100 mL). The combined org. extracts were dried over MgSO$_4$, filtered, and the solvent was removed under reduced pressure. Purification of the residue by FC (97:3 EA-MeOH) gave the title compound as a brown oil. TLC: rf (97:3 EA-MeOH)= 0.45. LC-MS-conditions 02: $t_R$=0.74 min; [M+H]$^+$=324.41.

2-[3-(2-Methyl-[1,3]dioxolan-2-yl)-benzyl]-4,5-dihydro-oxazole-4-carboxylic acid methyl ester In a flame dried round-bottomed flask equipped with a magnetic stir bar and under inert atmosphere (N$_2$), a solution of 3-hydroxy-2-{2-[3-(2-methyl-[1,3]dioxolan-2-yl)-phenyl]-acetylamino}-propionic acid methyl ester (2.30 g, 7.11 mmol) in dry THF (28.5 mL) was added at 0° C. to solution of (methoxycarbonylsulfamoyl)triethylammonium hydroxide (2.09 g, 8.50 mmol) in dry THF (28.5 mL) and the resulting suspension was stirred at 0° C. for 25 min. The reaction mixture was then stirred at reflux for 1 h. The mixture was then allowed to cool down to rt and filtered. The filter cake was rinsed with ether and EA and the filtrate was concentrated under reduced pressure. Purification of the residue by FC (7:3 EA-Hept) gave the title compound as a yellow oil. TLC: rf (7:3 EA-Hept)=0.34.

2-[3-(2-Methyl-[1,3]dioxolan-2-yl)-benzyl]-oxazole-4-carboxylic acid methyl ester In a flame dried round-bottomed flask equipped with a magnetic stir bar and under inert atmosphere (N$_2$), hexamethylenetetramine (1.10 g, 7.79 mmol) and DBU (1.17 mL, 7.75 mmol) were added to a stirred suspension of copper (II) bromide (1.73 g, 7.75 mmol) in deoxygenated dry $CH_2Cl_2$ (15 mL). After 20 min, a deoxygenated solution of 2-[3-(2-methyl-[1,3]dioxolan-2-yl)-benzyl]-4,5-dihydro-oxazole-4-carboxylic acid methyl ester (951 mg, 3.12 mmol) in $CH_2Cl_2$ (15.0 mL) was added and the reaction mixture was stirred at rt for 45 min. The solvent was removed under reduced pressure and the residue was partitioned between EA (50 mL), and 50 mL of a 1:1 mixture of sat. aq. $NH_4Cl$ and 25% aq. $NH_4OH$. The aq. layer was extracted with EA (50 mL) and the combined organic layers were washed with 50 mL of a 1:1 mixture of sat. aq. $NH_4Cl$ and 25% aq. $NH_4OH$ followed by 10% citric acid (50 mL), sat. aq. $NaHCO_3$ (50 mL) and brine (50 mL). The organic phase was dried over $MgSO_4$, filtered, and the solvent was removed under reduced pressure. Purification of the residue by FC (1:1 hept-EA) gave the title compound as a pale yellow solid. TLC: rf (1:1 hept-EA)=0.37. LC-MS-conditions 02: $t_R$=0.93 min, $[M+H]^+$=304.34.

2-(3-Acetyl-benzyl)-oxazole-4-carboxylic acid methyl ester

In a flame dried round-bottomed flask equipped with a magnetic stir bar and under inert atmosphere ($N_2$), a solution of 2-[3-(2-methyl-[1,3]dioxolan-2-yl)-benzyl]-oxazole-4-carboxylic acid methyl ester (383 mg, 1.26 mmol) in THF (21.5 mL) was treated with 1N HCl (3.4 mL) and the reaction mixture was stirred at rt overnight. Water was added and the reaction mixture was extracted twice with EA (25 mL). The combined organic layers were dried over $Na_2SO_4$, filtered, and the solvent was removed under reduced pressure to give the title compound as a white solid. LC-MS-conditions 02: $t_R$=0.88 min, $[M+AcCN+H]^+$=301.25.

2-(3-Acetyl-benzyl)-oxazole-4-carboxylic acid

In a flame dried round-bottomed flask equipped with a magnetic stir bar and under inert atmosphere ($N_2$), a solution of 2-(3-acetyl-benzyl)-oxazole-4-carboxylic acid methyl ester (330 mg, 1.27 mmol) in THF (12 mL) was treated at rt with 1N NaOH (6 mL, 6.00 mmol) and the reaction mixture was stirred for 1 h at rt. The reaction mixture was poured in 1N HCl and extracted twice with EA. The combined org. extracts were dried over $Na_2SO_4$, filtered, and the solvent was removed under reduced pressure to give the title compound as a colorless oil. LC-MS-conditions 02: $t_R$=0.78 min, $[M+AcCN+H]^+$=287.05.

2-(3-Acetyl-benzyl)-oxazole-4-carbonyl azide

In a flame dried round-bottomed flask equipped with a magnetic stir bar and under inert atmosphere ($N_2$), a suspension of 2-(3-acetyl-benzyl)-oxazole-4-carboxylic acid (314 mg, 1.28 mmol) in toluene (12.8 mL) was treated with a drop of DMF followed by oxalyl chloride (0.14 mL, 1.54 mmol) and the resulting yellow solution was stirred at rt for 1 h. The solvent was then removed under reduced pressure (coevaporation with toluene) to give 2-(3-acetyl-benzyl)-oxazole-4-carbonyl chloride.

In a flame dried round-bottomed flask equipped with a magnetic stir bar and under inert atmosphere ($N_2$), a solution of the crude 2-(3-acetyl-benzyl)-oxazole-4-carbonyl chloride in dry acetone (13.5 mL) was cooled to 0° C. and a solution of sodium azide (210 mg, 3.20 mmol) in $H_2O$ (1.7 mL) was added dropwise. The reaction mixture was stirred at 0° C. for 1 h. The mixture was concentrated under reduced pressure (coevaporation with toluene) then dissolved in $CH_2Cl_2$ and filtered. The filtrate was concentrated under reduced pressure to give the title compound as an orange oil. LC-MS-conditions 02: $t_R$=0.91 min $[M+AcCN+H]^+$=312.31.

[2-(3-Acetyl-benzyl)-oxazol-4-yl]-carbamic acid tert-butyl ester

In a flame dried round-bottomed flask equipped with a magnetic stir bar and under inert atmosphere ($N_2$), a solution of 2-(3-acetyl-benzyl)-oxazole-4-carbonyl azide (240 mg, 0.89 mmol) in xylene (5.0 mL) was heated to 140° C. for 5 min. tert-Butanol (0.83 mL, 8.88 mmol) was then added and the reaction mixture was further stirred at 140° C. for 5 min. The solvent was removed under reduced pressure. Purification of the residue by FC (7:3 hept-EA) gave the title compound as a pale white solid. TLC: rf (7:3 hept-EA)=0.29. LC-MS-conditions 02: $t_R$=1.00 min, $[M+H]^+$=317.28.

[2-(3-Acetyl-benzyl)-oxazol-4-yl]-[2-(4-trifluoromethyl-phenyl)-vinyl]-carbamic acid tert-butyl ester In a flame dried round-bottomed flask equipped with a magnetic stir bar and under inert atmosphere ($N_2$), a suspension of trans-4-(trifluoromethyl)cinnamic acid (20 mg, 0.10 mmol) in toluene (1.0 mL) was treated with a drop of DMF followed by oxalyl chloride (0.02 mL, 0.23 mmol) and the resulting yellow solution was stirred at rt for 30 min. The solvent was then removed under reduced pressure (coevaporation with toluene) to give 3-(4-trifluoromethyl-phenyl)-acryloyl chloride.

In a flame dried round-bottomed flask equipped with a magnetic stir bar and under inert atmosphere ($N_2$), a solution of [2-(3-acetyl-benzyl)-oxazol-4-yl]-carbamic acid tert-butyl ester (15 mg, 0.05 mmol) in THF (1.0 mL) was added to a suspension of NaH (5 mg, 0.12 mmol) in THF (0.5 mL) at 0° C. The resulting suspension was stirred at 0° C. for 5 min and at rt for 30 min. It was cooled to 0° C. and treated dropwise with a solution of the above prepared 3-(4-trifluoromethyl-phenyl)-acryloyl chloride in THF (1.0 mL). The resulting suspension was stirred for 5 min at 0° C. followed by 30 min at rt. Water was then added and the aq. layer was extracted several time with EA. The combined org. extracts were dried over $Na_2SO_4$, filtered, and the solvent was removed under reduced pressure to give the title compound as a yellow oil. TLC: rf (6:4 hept-EA)=0.20. LC-MS-conditions 02: $t_R$=1.17 min, $[M+H]^+$=515.82.

2-[5-(2-Methyl-[1,3]dioxolan-2-yl)-thiophen-2-yl]-thioacetamide

In a flame dried round-bottomed flask equipped with a magnetic stir bar and under inert atmosphere ($N_2$), hexamethyldisilthiane (8.9 mL, 42.31 mmol) was added dropwise to a solution of NaOMe (2.35 g, 42.31 mmol) in dry DMF (35 mL) and the reaction mixture was stirred at rt for 15 min. This dark blue solution was then added to a solution of [5-(2-methyl-[1,3]dioxolan-2-yl)-thiophen-2-yl]-acetonitrile (3.27 g, 16.93 mmol) in DMF (30 mL) and the reaction mixture was stirred for 2 days at rt. Water (100 mL) was then added and the mixture was extracted twice with EA (100 mL). The combined org. phases were dried over $MgSO_4$, filtered, and the solvent was removed under reduced pressure. Purification of the residue by FC (1:1 hept-EA) gave the title compound as a yellow oil. TLC: rf (1:1 hept-EA)=0.35. LC-MS-conditions 02: $t_R$=0.81 min, $[M+H]^+$=244.38.

2-(5-Acetyl-thiophen-2-ylmethyl)-thiazole-4-carboxylic acid ethyl ester

In a flame dried round-bottomed flask equipped with a magnetic stir bar and under inert atmosphere ($N_2$), a solution of 2-[5-(2-methyl-[1,3]dioxolan-2-yl)-thiophen-2-yl]-thioacetamide (2.88 g, 11.83 mmol) and ethylbromopyruvate (1.74 mL, 11.83 mmol) in ethanol (34.0 mL) was stirred for 16 h at reflux. The solvent was removed under reduced pressure and the residue was dissolved in EA (150 mL) and washed with 7% aq. $NaHCO_3$ (100 mL). The org. phase was dried over $MgSO_4$, filtered, and the solvent was removed under reduced pressure. Purification of the residue by FC (1:1 hept-EA) gave the title compound as an orange oil. TLC: rf (1:1 hept-EA)=0.24. LC-MS-conditions 02: $t_R$=0.93 min, $[M+H]^+$=296.37.

2-(5-Acetyl-thiophen-2-ylmethyl)-thiazole-4-carboxylic acid

In a flame dried round-bottomed flask equipped with a magnetic stir bar and under inert atmosphere ($N_2$), a solution of 2-(5-acetyl-thiophen-2-ylmethyl)-thiazole-4-carboxylic acid ethyl ester (2.20 g, 7.46 mmol) in THF (32 mL) was treated at rt with 1N NaOH (16 mL, 16.00 mmol) and the reaction mixture was stirred for 16 h at rt. The reaction mixture was poured in 1N HCl and extracted twice with EA. The combined org. extracts were dried over $MgSO_4$, filtered, and the solvent was removed under reduced pressure to give the title compound as a deep brown foam. LC-MS-conditions 02: $t_R$=0.78 min, $[M+H]^+$=268.08.

[2-(5-Acetyl-thiophen-2-ylmethyl)-thiazol-4-yl]-carbamic acid tert-butyl ester In a flame dried round-bottomed flask equipped with a magnetic stir bar and under inert atmosphere ($N_2$), a solution of 2-(5-acetyl-thiophen-2-ylmethyl)-thiazole-4-carboxylic acid (1.95 g, 7.29 mmol) in a mixture of toluene (20 mL) and t-butanol (10.3 mL) was treated at rt with $Et_3N$ (1.17 mL, 8.90 mmol) and DPPA (1.65 mL, 7.66 mmol). After stirring at rt for 5 min, the reaction mixture was stirred at 90° C. for 2 h. Cuprous chloride (112 mg, 1.09 mmol) was then added and the reaction mixture was stirred under reflux for 1 h. The reaction was allowed to cool down to rt and EA (50 mL) was added followed by $NaHCO_3$ (50 mL). The aq. layer was extracted twice with EA (50 mL) and the combined org. layers were washed with brine (100 mL), dried over $MgSO_4$, filtered, and the solvent was removed under reduced pressure. Purification of the residue by FC (6:4 hept-EA) gave the title compound as an orange oil. TLC: rf (6:4 hept-EA)=0.35. LC-MS-conditions 02: $t_R$=1.02 min, $[M+H]^+$=339.42.

1-[5-(4-Amino-thiazol-2-ylmethyl)-thiophen-2-yl]-ethanone hydrochloride

In a flame dried round-bottomed flask equipped with a magnetic stir bar and under inert atmosphere ($N_2$), a solution of [2-(5-acetyl-thiophen-2-ylmethyl)-thiazol-4-yl]-carbamic acid tert-butyl ester (75 mg, 0.22 mmol) in dry $CH_2Cl_2$ (2.2 mL) was treated at 0° C. with HCl (0.55 mL of a 4M solution in dioxane, 2.22 mmol). After stirring at 0° C. for 1 h, the reaction mixture was stirred at rt for 16 h. The solvents were removed under reduced pressure to give the title compound as a light brown solid. LC-MS-conditions 02: $t_R$=0.71 min, $[M+AcCN+H]^+$=280.14.

2-Furan-2-yl-2-methyl-[1,3]dioxolane

In a flame dried round-bottomed flask equipped with a magnetic stir bar and under inert atmosphere ($N_2$), a solution of 1-furan-2-yl-ethanone (50.00 g, 454.0 mmol) in ethylene glycol (500.0 mL) was treated with trimethylorthoformate (100.0 mL, 908.0 mmol) followed by $LiBF_4$ (7.00 g, 75 mmol). The reaction mixture was heated at 95° C. overnight. Sat. aq. $NaHCO_3$ (500 mL) was added and the mixture was extracted with EA (500 mL). The org. extracts were washed with brine (2×250 mL), dried over $MgSO_4$, filtered, and the solvent was removed under reduced pressure. Purification of the residue by distillation (11 mbar, 71-73° C.) gave the title compound as a colorless oil.

[5-(2-Methyl-[1,3]dioxolan-2-yl)-furan-2-yl]-methanol

In a flame dried round-bottomed flask equipped with a magnetic stir bar and under inert atmosphere ($N_2$), to a solution of n-BuLi (14.6 mL of a 1.6M solution in hexane, 23.35 mmol) in THF (21 mL) at −78° C. was added dropwise a solution of 2-furan-2-yl-2-methyl-[1,3]dioxolane (3.00 g, 19.46 mmol) in THF (6.0 mL). The reaction mixture was then stirred for 1 h at −78° C. before DMF (4.52 mL, 58.38 mmol) was added dropwise. The reaction mixture was stirred for 1 h at −78° C. Sat. aq. $NH_4Cl$ (50 mL) was added and the mixture was extracted with EA (2×50 mL). The combined org. extracts were dried over $MgSO_4$, filtered, and the solvent was removed under reduced pressure to give 5.91 g of crude 5-(2-methyl-[1,3]dioxolan-2-yl)-furan-2-carbaldehyde as an orange oil. LC-MS-conditions 02: $t_R$=0.75 min; $[M+H]^+$=183.23. The crude material was dissolved, under inert atmosphere ($N_2$) in MeOH (59.0 mL) and treated at 0° C., portionwise, over 20 min, with $NaBH_4$ (1.53 g, 38.92 mmol in five equal portions). The reaction mixture was stirred for 45 min at rt. The reaction mixture was poured on water (80 mL) and the aq. layer was extracted with EA (2×60 mL). The combined org. extracts were dried over $MgSO_4$, filtered, and the solvents were removed under reduced pressure. Purification of the residue by FC (50:50 hept-EA) gave the title compound: TLC: rf (50:50 hept-EA)=0.27. LC-MS-conditions 02: $t_R$=0.65 min; $[M+H]^+$=185.28.

2-(5-Chloromethyl-furan-2-yl)-2-methyl-[1,3]dioxolane

In a flame dried round-bottomed flask equipped with a magnetic stir bar and under inert atmosphere ($N_2$), a solution of [5-(2-methyl-[1,3]dioxolan-2-yl)-furan-2-yl]-methanol (3.50 g, 19.00 mmol) in dry $CH_2Cl_2$ (35.0 mL) was treated at 0° C. with $Et_3N$ (3.44 mL, 22.80 mmol) followed by DMAP (232 mg, 1.90 mmol) and Ms-Cl (1.77 mL, 22.80 mmol). After stirring at rt for 2 h, the reaction mixture was quenched with water (40 mL), extracted with $CH_2Cl_2$ (40 mL) and the combined org. extracts were dried over $MgSO_4$, filtered, and the solvents were removed under reduced. Purification of the residue by FC (8:2:0.1 hept-EA-$Et_3N$) gave the title compound as a yellow oil: TLC: rf (4:1 hept-EA)=0.35.

[5-(2-Methyl-[1,3]dioxolan-2-yl)-furan-2-yl]-acetonitrile

In a flame dried round-bottomed flask equipped with a magnetic stir bar and under inert atmosphere ($N_2$), a solution of 2-(5-chloromethyl-furan-2-yl)-2-methyl-[1,3]dioxolane (2.37 mg, 11.68 mmol) in DMSO (50 mL) was treated with sodium cyanide (2.29 g, 46.72 mmol) and the reaction mixture was stirred at 80° C. for 45 min. Water (100 mL) was added to the cooled reaction mixture and the product was extracted with EA (2×100 mL). The combined org. extracts were dried over MgSO$_4$, filtered, and the solvents were removed under reduced pressure. Purification of the residue by FC (2:1 hept-EA) gave the title compound as a yellow oil. LC-MS-conditions 02: $t_R$=0.83 min.

2-[5-(2-Methyl-[1,3]dioxolan-2-yl)-furan-2-yl]-thio-acetamide

In a flame dried round-bottomed flask equipped with a magnetic stir bar and under inert atmosphere (N$_2$), hexamethyldisilthiane (9.45 mL, 45.07 mmol) was added dropwise to a solution of NaOMe (2.51 g, 45.07 mmol) in dry DMF (40 mL) and the reaction mixture was stirred at rt for 15 min. This dark blue solution was then added to a solution of [5-(2-methyl-[1,3]dioxolan-2-yl)-furan-2-yl]-acetonitrile (3.48 g, 18.03 mmol) in DMF (30 mL) and the reaction mixture was stirred for 16 h at rt. Water (300 mL) was then added and the mixture was extracted twice with EA (300 mL). The combined org. phases were dried over MgSO$_4$, filtered, and the solvent was removed under reduced pressure. Purification of the residue by FC (6:4 hept-EA) gave the title compound as a yellow oil. TLC: rf (6:4 hept-EA)=0.18. LC-MS-conditions 02: $t_R$=0.74 min, [M+H]$^+$=228.44.

2-(5-Acetyl-furan-2-ylmethyl)-thiazole-4-carboxylic acid ethyl ester

In a flame dried round-bottomed flask equipped with a magnetic stir bar and under inert atmosphere (N$_2$), a solution of 2-[5-(2-methyl-[1,3]dioxolan-2-yl)-furan-2-yl]-thioacetamide (3.20 g, 14.06 mmol) and ethylbromopyruvate (2.07 mL, 14.06 mmol) in ethanol (40 mL) was stirred for 30 min at reflux. The solvent was removed under reduced pressure and the residue was dissolved in EA (150 mL) and washed with 7% aq. NaHCO$_3$ (100 mL). The org. phase was dried over MgSO$_4$, filtered, and the solvent was removed under reduced pressure. Purification of the residue by FC (1:1 hept-EA) gave the title compound as an orange oil. TLC: rf (1:1 hept-EA)= 0.24. LC-MS-conditions 02: $t_R$=0.86 min, [M+H]$^+$=280.30.

2-(5-Acetyl-furan-2-ylmethyl)-thiazole-4-carboxylic acid

In a flame dried round-bottomed flask equipped with a magnetic stir bar and under inert atmosphere (N$_2$), a solution of 2-(5-acetyl-furan-2-ylmethyl)-thiazole-4-carboxylic acid ethyl ester (1.71 g, 6.13 mmol) in THF (26 mL) was treated at rt with 1N NaOH (13 mL, 13.00 mmol) and the reaction mixture was stirred for 16 h at rt. The reaction mixture was poured in 1N HCl and extracted twice with EA. The combined org. extracts were dried over MgSO$_4$, filtered, and the solvent was removed under reduced pressure to give the title compound as a deep brown foam. LC-MS-conditions 02: $t_R$=0.71 min, [M+H]$^+$=252.29.

[2-(5-Acetyl-furan-2-ylmethyl)-thiazol-4-yl]-carbamic acid tert-butyl ester

In a flame dried round-bottomed flask equipped with a magnetic stir bar and under inert atmosphere (N$_2$), a solution of 2-(5-acetyl-furan-2-ylmethyl)-thiazole-4-carboxylic acid (1.00 g, 3.98 mmol) in a mixture of toluene (10.8 mL) and t-butanol (5.6 mL) was treated at rt with Et$_3$N (0.64 mL, 4.58 mmol) and DPPA (0.90 mL, 4.18 mmol). After stirring at rt for 5 min, the reaction mixture was stirred at 90° C. for 2 h. Cuprous chloride (61 mg, 0.60 mmol) was then added and the reaction mixture was stirred under reflux for 1 h. The reaction was allowed to cool down to rt and EA (50 mL) was added followed by NaHCO$_3$ (50 mL). The aq. layer was extracted twice with EA (50 mL) and the combined org. layers were washed with brine (100 mL), dried over MgSO$_4$, filtered, and the solvent was removed under reduced pressure. Purification of the residue by FC (6:4 hept-EA) gave the title compound as an orange oil. TLC: rf (6:4 hept-EA)=0.32. LC-MS-conditions 02: $t_R$=0.97 min, [M+H]$^+$=323.37.

1-[5-(4-Amino-thiazol-2-ylmethyl)-furan-2-yl]-ethanone hydrochloride

In a flame dried round-bottomed flask equipped with a magnetic stir bar and under inert atmosphere (N$_2$), a solution of [2-(5-acetyl-furan-2-ylmethyl)-thiazol-4-yl]-carbamic acid tert-butyl ester (167 mg, 0.52 mmol) in dry CH$_2$Cl$_2$ (5.2 mL) was treated at 0° C. with HCl (1.3 mL of a 4M solution in dioxane, 5.18 mmol). After stirring at 0° C. for 1 h, the reaction mixture was stirred at rt for 16 h. The solvents were removed under reduced pressure to give the title compound. LC-MS-conditions 02: $t_R$=0.65 min, [M+H]$^+$=223.36.

2-Methyl-5-m-tolyl-oxazole-4-carboxylic acid

Prepared starting from 3-oxo-3-m-tolyl-propionic acid ethyl ester following sequentially general procedure F, G and E. LC-MS-conditions 02: $t_R$=0.85 min; [M+H]$^+$=218.46.

5-(3-Fluoro-phenyl)-thiazole-4-carboxylic acid

Prepared starting from 3-fluoro-benzaldehyde following sequentially general procedures R, T, U, V and E. LC-MS-conditions 01: $t_R$=0.81 min; [M+H]$^+$=224.38.

5-(4-Fluoro-phenyl)-oxazole-4-carboxylic acid

Prepared starting from 4-fluoro-benzoic acid following sequentially general procedure K, J, I, H and E. LC-MS-conditions 02: $t_R$=0.80 min; [M+AcCN+H]$^+$=249.04.

2-Ethyl-5-phenyl-oxazole-4-carboxylic acid

Prepared starting from 3-oxo-3-phenyl-propionic acid ethyl ester following sequentially general procedure J, I, H and E. LC-MS-conditions 02: $t_R$=0.85 min; [M+H]$^+$=218.19.

2-Cyclopropyl-5-phenyl-thiazole-4-carboxylic acid

Prepared starting from benzaldehyde following sequentially general procedures R, S and E. LC-MS-conditions 02: $t_R$=0.91 min; [M+H]$^+$=246.69.

5-(3-Chloro-phenyl)-2-methyl-oxazole-4-carboxylic acid

Prepared starting from 3-chloro-benzoic acid following sequentially general procedure K, F, G and E. LC-MS-conditions 02: $t_R$=0.87 min; [M+H]$^+$=238.06.

PREPARATION OF EXAMPLES

Example 1

[2-(5-Oxo-hexyl)-oxazol-4-yl]-carbamic acid 2-chloro-benzyl ester

Following general procedure L, starting from {2-[4-(2-methyl-[1,3]dioxolan-2-yl)-butyl]-oxazol-4-yl}-carbamic acid 2-chloro-benzyl ester.
LC-MS-conditions 02: $t_R$=1.01 min; $[M+H]^+$=351.10.

Example 2

5-Phenyl-oxazole-4-carboxylic acid [2-(5-oxo-hexyl)-oxazol-4-yl]-amide

In a flame dried round-bottomed flask equipped with a magnetic stir bar and under inert atmosphere ($N_2$), a solution of [2-(5-oxo-hexyl)-oxazol-4-yl]-(5-phenyl-oxazole-4-carbonyl)-carbamic acid tert-butyl ester (31 mg, 0.06 mmol) in dry $CH_2Cl_2$ (1.0 mL) was treated at 0° C. with trifluoroacetic acid (0.05 mL, 0.64 mmol). After stirring at rt for 16 h, the reaction mixture was quenched with sat. aq. $NaHCO_3$, extracted with $CH_2Cl_2$ (3×10 mL) and the combined org. extracts were dried over $Na_2SO_4$, filtered, and the solvents were removed under reduced pressure. Purification of the residue by HPLC gave the title compound as a light brown solid. TLC: rf (1:1 hept-EA)=0.35. LC-MS-conditions 02: $t_R$=1.02 min, $[M+H]^+$=354.25.

Example 3

[2-(3-Acetyl-pyrazol-1-ylmethyl)-oxazol-4-yl]-carbamic acid 2-chloro-benzyl ester In a flame dried round-bottomed flask equipped with a magnetic stir bar and under inert atmosphere ($N_2$), a solution of 2-(3-acetyl-pyrazol-1-ylmethyl)-oxazole-4-carbonyl azide (129 mg, 0.50 mmol) in xylene (2.0 mL) was heated to 140° C. for 5 min. 2-chlorobenzyl alcohol (144 mg, 1.00 mmol) was then added and the reaction mixture was further stirred at 140° C. for 5 min. The solvent was removed under reduced pressure. Purification of the residue by FC (9:1→2:1 hept-EA) gave the title compound as a pale yellow solid. TLC: rf (1:1 hept-EA)=0.31. LC-MS-conditions 02: $t_R$=0.99 min $[M+H]^+$=375.19.

Example 4

[2-(5,5-Difluoro-hexyl)-oxazol-4-yl]-carbamic acid 2-chloro-benzyl ester

In a flame dried round-bottomed flask equipped with a magnetic stir bar and under inert atmosphere ($N_2$), a solution of 2-(5,5-difluoro-hexyl)-oxazole-4-carbonyl azide (100 mg, 0.39 mmol) in xylene (2.0 mL) was heated to 140° C. for 5 min. 2-Chlorobenzyl alcohol (558 mg, 3.87 mmol) was then added and the reaction mixture was further stirred at 140° C. for 5 min. The solvent was removed under reduced pressure. Purification of the residue by FC (4:1 hept-EA) gave the title compound as a white solid. TLC: rf (4:1 hept-EA)=0.30. LC-MS-conditions 02: $t_R$=1.10 min $[M+H]^+$=373.23.

Example 5

2-Methyl-5-m-tolyl-oxazole-4-carboxylic acid [2-(5,5-difluoro-hexyl)-oxazol-4-yl]-amide In a flame dried round-bottomed flask equipped with a magnetic stir bar and under inert atmosphere ($N_2$), a solution of [2-(5,5-difluoro-hexyl)-oxazol-4-yl]-(2-methyl-5-m-tolyl-oxazole-4-carbonyl)-carbamic acid tert-butyl ester (32 mg, 0.06 mmol) in dry $CH_2Cl_2$ (1.0 mL) was treated at 0° C. with trifluoroacetic acid (0.05 mL, 0.65 mmol). After stirring at rt for 16 h, the reaction mixture was quenched with sat. aq. $NaHCO_3$, extracted with $CH_2Cl_2$ (3×10 mL) and the combined org. extracts were dried over $Na_2SO_4$, filtered, and the solvents were removed under reduced pressure. Purification of the residue by HPLC gave the title compound as a light brown solid. TLC: rf (4:1 hept-EA)=0.21. LC-MS-conditions 02: $t_R$=1.17 min, $[M+H]^+$=404.43.

Example 6

2-Methyl-5-m-tolyl-oxazole-4-carboxylic acid [2-(5-oxo-hexyl)-oxazol-4-yl]-amide In a flame dried round-bottomed flask equipped with a magnetic stir bar and under inert atmosphere ($N_2$), a solution of (2-methyl-5-m-tolyl-oxazole-4-carbonyl)-[2-(5-oxo-hexyl)-oxazol-4-yl]-carbamic acid tert-butyl ester (50 mg, 0.10 mmol) in dry $CH_2Cl_2$ (1.0 mL) was treated at 0° C. with trifluoroacetic acid (0.08 mL, 1.07 mmol). After stirring at rt for 16 h, the reaction mixture was quenched with sat. aq. $NaHCO_3$, extracted with $CH_2Cl_2$ (3×10 mL) and the combined org. extracts were dried over $Na_2SO_4$, filtered, and the solvents were removed under reduced pressure. Purification of the residue by HPLC gave the title compound as a colorless oil. TLC: rf (6:4 hept-EA)=0.26. LC-MS-conditions 02: $t_R$=1.08 min, $[M+H]^+$=382.50.

Example 7

5-(3-Fluoro-phenyl)-thiazole-4-carboxylic acid [2-(5-oxo-hexyl)-oxazol-4-yl]-amide In a flame dried round-bottomed flask equipped with a magnetic stir bar and under inert atmosphere ($N_2$), a solution of [5-(3-fluoro-phenyl)-thiazole-4-carbonyl]-[2-(5-oxo-hexyl)-oxazol-4-yl]-carbamic acid tert-butyl ester (30 mg, 0.06 mmol) in dry $CH_2Cl_2$ (1.0 mL) was treated at 0° C. with trifluoroacetic acid (0.05 mL, 0.64 mmol). After stirring at rt for 3 h, the reaction mixture was quenched with sat. aq. $NaHCO_3$, extracted with $CH_2Cl_2$ (3×10 mL) and the combined org. extracts were dried over $Na_2SO_4$, filtered, and the solvents were removed under reduced pressure. Purification of the residue by HPLC gave the title compound as a colorless oil. LC-MS-conditions 01: $t_R$=0.99 min, $[M+H]^+$=388.04.

Example 8

5-(4-Fluoro-phenyl)-oxazole-4-carboxylic acid [2-(5-oxo-hexyl)-oxazol-4-yl]-amide In a flame dried round-bottomed flask equipped with a magnetic stir bar and under inert atmosphere ($N_2$), a solution of [5-(4-fluoro-phenyl)-oxazole-4-carbonyl]-[2-(5-oxohexyl)-oxazol-4-yl]-carbamic acid tert-butyl ester (41 mg, 0.09 mmol) in dry $CH_2Cl_2$ (1.0 mL) was treated at 0° C. with trifluoroacetic acid (0.07 mL, 0.90 mmol). After stirring at rt for 4 h, the reaction mixture was quenched with sat. aq. $NaHCO_3$, extracted with $CH_2Cl_2$ (3×10 mL) and the combined org. extracts were dried over $Na_2SO_4$, filtered, and the solvents were removed under reduced pressure. Purification of the residue by HPLC gave the title compound as a white solid. LC-MS-conditions 01: $t_R$=1.00 min, $[M+H]^+$=372.04.

Example 9

2-Ethyl-5-phenyl-oxazole-4-carboxylic acid [2-(5-oxo-hexyl)-oxazol-4-yl]-amide

In a flame dried round-bottomed flask equipped with a magnetic stir bar and under inert atmosphere ($N_2$), a solution of (2-ethyl-5-phenyl-oxazole-4-carbonyl)-[2-(5-oxo-hexyl)-oxazol-4-yl]-carbamic acid tert-butyl ester (43 mg, 0.09 mmol) in dry $CH_2Cl_2$ (1.0 mL) was treated at 0° C. with trifluoroacetic acid (0.07 mL, 0.90 mmol). After stirring at rt for 4 h, the reaction mixture was quenched with sat. aq. $NaHCO_3$, extracted with $CH_2Cl_2$ (3×10 mL) and the combined org. extracts were dried over $Na_2SO_4$, filtered, and the solvents were removed under reduced pressure. Purification of the residue by HPLC gave the title compound as a white solid. LC-MS-conditions 01: $t_R$=1.05 min, $[M+H]^+$=382.12.

Example 10

[2-(4-Bromo-pyrazol-1-ylmethyl)-oxazol-4-yl]-carbamic acid 2-chloro-benzyl ester In a flame dried round-bottomed flask equipped with a magnetic stir bar and under inert atmosphere ($N_2$), a solution of 2-(4-bromo-pyrazol-1-ylmethyl)-oxazole-4-carbonyl azide (152 mg, 0.51 mmol) in xylene (2.0 mL) was heated to 140° C. for 5 min. 2-Chlorobenzyl alcohol (147 mg, 1.02 mmol) was then added and the reaction mixture was further stirred at 140° C. for 30 min. The solvent was removed under reduced pressure. Purification of the residue by FC (9:1→2:1 hept-EA) gave the title compound as a white solid. TLC: rf (1:1 hept-EA)=0.31. LC-MS-conditions 02: $t_R$=1.04 min $[M+H]^+$=410.90.

Example 11

[2-(3-Acetyl-pyrazol-1-ylmethyl)-oxazol-4-yl]-carbamic acid 2-chloro-4-fluoro-benzyl ester In a flame dried round-bottomed flask equipped with a magnetic stir bar and under inert atmosphere ($N_2$), a solution of 2-(3-acetyl-pyrazol-1-ylmethyl)-oxazole-4-carbonyl azide (26 mg, 0.10 mmol) in xylene (0.5 mL) was heated to 140° C. for 5 min. 2-chlorobenzyl alcohol (33 mg, 0.20 mmol) was then added and the reaction mixture was further stirred at 140° C. for 5 min. The solvent was removed under reduced pressure. Purification of the residue by FC (9:1→2:1 hept-EA) gave the title compound as a pale yellow solid. TLC: rf (1:1 hept-EA)=0.33. LC-MS-conditions 01: $t_R$=0.95 min $[M+H]^+$=392.99.

Example 12

[2-(3-Acetyl-pyrazol-1-ylmethyl)-oxazol-4-yl]-carbamic acid 3-methoxy-benzyl ester In a flame dried round-bottomed flask equipped with a magnetic stir bar and under inert atmosphere ($N_2$), a solution of 2-(3-acetyl-pyrazol-1-ylmethyl)-oxazole-4-carbonyl azide (51 mg, 0.20 mmol) in xylene (1.0 mL) was heated to 140° C. for 5 min. 3-methoxybenzyl alcohol (55 mg, 0.39 mmol) was then added and the reaction mixture was further stirred at 140° C. for 5 min. The solvent was removed under reduced pressure. Purification of the residue by FC (9:1→2:1 hept-EA) gave the title compound as a pale yellow solid. TLC: rf (1:1 hept-EA)=0.32. LC-MS-conditions 05b: $t_R$=0.65 min, $[M+H]^+$=370.94.

Example 13

[2-(3-Acetyl-pyrazol-1-ylmethyl)-oxazol-4-yl]-carbamic acid 4-trifluoromethyl-benzyl ester In a flame dried round-bottomed flask equipped with a magnetic stir bar and under inert atmosphere ($N_2$), a solution of 2-(3-acetyl-pyrazol-1-ylmethyl)-oxazole-4-carbonyl azide (54 mg, 0.21 mmol) in xylene (1.0 mL) was heated to 140° C. for 5 min. 4-(trifluoromethyl)benzyl alcohol (75 mg, 0.42 mmol) was then added and the reaction mixture was further stirred at 140° C. for 5 min. The solvent was removed under reduced pressure. Purification of the residue by FC (9:1→2:1 hept-EA) gave the title compound as a pale yellow solid. TLC: rf (1:1 hept-EA)=0.29. LC-MS-conditions 07: $t_R$=1.42 min, $[M+H]^+$=409.20.

Example 14

[2-(5-Acetyl-thiophen-2-ylmethyl)-oxazol-4-yl]-carbamic acid 2-chloro-benzyl ester In a flame dried round-bottomed flask equipped with a magnetic stir bar and under inert atmosphere ($N_2$), a solution of a mixture of 2-(5-acetyl-thiophen-2-ylmethyl)-oxazole-4-carbonyl azide and 2-[5-(2-methyl-[1,3]dioxolan-2-yl)-thiophen-2-ylmethyl]-oxazole-4-carbonyl azide (138 mg) in xylene (0.5 mL) was heated to 140° C. for 5 min. 2-chlorobenzyl alcohol (144 mg, 1.00 mmol) was then added and the reaction mixture was further stirred at 140° C. for 5 min. The solvent was removed under reduced pressure. Purification of the residue by FC (20:1→1:1 hept-EA) followed by preparative HPLC gave the title compound as a white solid. LC-MS-conditions 07: $t_R$=1.50 min, $[M+H]^+$=391.10.

Example 15

[2-(3-Acetyl-benzyl)-oxazol-4-yl]-carbamic acid 3-trifluoromethoxy-benzyl ester

In a flame dried round-bottomed flask equipped with a magnetic stir bar and under inert atmosphere ($N_2$), a solution of 2-(3-acetyl-benzyl)-oxazole-4-carbonyl azide (100 mg, 0.37 mmol) in xylene (2.0 mL) was heated to 140° C. for 5 min. 3-(trifluoromethoxy)benzyl alcohol (711 mg, 3.70 mmol) was then added and the reaction mixture was further stirred at 140° C. for 5 min. The solvent was removed under reduced pressure. Purification of the residue by FC (9:1→3:7 hept-EA) followed by preparative HPLC gave the title compound as a white solid. LC-MS-conditions 02: $t_R$=1.09 min, $[M+H]^+$=434.88.

Example 16

2-Cyclopropyl-5-phenyl-thiazole-4-carboxylic acid [2-(3-acetyl-pyrazol-1-ylmethyl)-oxazol-4-yl]-amide In a flame dried round-bottomed flask equipped with a magnetic stir bar and under inert atmosphere ($N_2$), a solution of [2-(3-acetyl-pyrazol-1-ylmethyl)-oxazol-4-yl]-(2-cyclopropyl-5-phenyl-thiazole-4-carbonyl)-carbamic acid tert-butyl ester (13 mg, 0.02 mmol) in dry $CH_2Cl_2$ (1.0 mL) was treated at 0° C. with trifluoroacetic acid (0.08 mL, 1.00 mmol). After stirring at rt for 16 h, the reaction mixture was quenched with sat. aq. $NaHCO_3$, extracted with $CH_2Cl_2$ (3×10 mL) and the combined org. extracts were dried over $Na_2SO_4$, filtered, and the solvents were removed under reduced pressure. Purification of the residue by FC (5:1→3:1 hept:EA) gave the title compound as a white solid. TLC: rf (1:1 hept-EA)=0.34. LC-MS-conditions 02: $t_R$=1.08 min, $[M+H]^+$=433.89.

Example 17

(E)-N-[2-(3-Acetyl-benzyl)-oxazol-4-yl]-3-(4-trifluoromethyl-phenyl)-acrylamide

In a flame dried round-bottomed flask equipped with a magnetic stir bar and under inert atmosphere ($N_2$), a solution of [2-(3-acetyl-benzyl)-oxazol-4-yl]-[2-(4-trifluoromethyl-phenyl)-vinyl]-carbamic acid tert-butyl ester (25 mg, 0.05 mmol) in dry $CH_2Cl_2$ (1.0 mL) was treated at 0° C. with trifluoroacetic acid (0.04 mL, 0.50 mmol). After stirring at rt for 16 h, the reaction mixture was quenched with sat. aq. $NaHCO_3$, extracted with $CH_2Cl_2$ (3×10 mL) and the combined org. extracts were dried over $Na_2SO_4$, filtered, and the solvents were removed under reduced pressure. Purification of the residue by FC (6:4 hept:EA) gave the title compound as an orange oil. TLC: rf (6:4 hept-EA)=0.24. LC-MS-conditions 02: $t_R$=1.09 min, $[M+H]^+$=415.12.

Example 18

5-Phenyl-oxazole-4-carboxylic acid [2-(5-acetyl-thiophen-2-ylmethyl)-thiazol-4-yl]-amide In a flame dried round-bottomed flask equipped with a magnetic stir bar and under inert atmosphere ($N_2$), a solution of 5-phenyl-1,3-oxazole-4-carboxylic acid (40 mg, 0.21 mmol) in $CH_2Cl_2$ (2.0 mL) was treated sequentially with DMAP (6 mg, 0.05 mmol), HOBt (34 mg, 0.25 mmol), EDC.HCl (101 mg, 0.53 mmol) and DIPEA (0.14 mL, 0.85 mmol) and the resulting mixture was stirred at rt for 15 min. This solution was then added to a solution of 1-[5-(4-amino-thiazol-2-ylmethyl)-thiophen-2-yl]-ethanone hydrochloride (58 mg, 0.21 mmol) in dry $CH_2Cl_2$ (0.5 mL) and the reaction mixture was stirred for 2 days at rt. $CH_2Cl_2$ (20 mL) was then added and the org. phase was washed with brine (15 mL). The org. phase was then dried over $MgSO_4$, filtered, and the solvents were removed under reduced pressure. Purification of the residue by FC (1:1 hept:EA) followed by HPLC gave the title compound as a yellow solid. LC-MS-conditions 05: $t_R$=0.98 min, $[M+H]^+$=410.16.

Example 19

5-(3-Chloro-phenyl)-2-methyl-oxazole-4-carboxylic acid [2-(5-acetyl-thiophen-2-ylmethyl)-thiazol-4-yl]-amide In a flame dried round-bottomed flask equipped with a magnetic stir bar and under inert atmosphere ($N_2$), a solution of 5-(3-chloro-phenyl)-2-methyl-oxazole-4-carboxylic acid (57 mg, 0.24 mmol) in $CH_2Cl_2$ (2.4 mL) was treated sequentially with DMAP (7 mg, 0.06 mmol), HOBt (39 mg, 0.29 mmol), EDC.HCl (114 mg, 0.60 mmol) and DIPEA (0.16 mL, 0.96 mmol) and the resulting mixture was stirred at rt for 30 min. This solution was then treated with 1-[5-(4-amino-thiazol-2-ylmethyl)-thiophen-2-yl]-ethanone hydrochloride (66 mg, 0.24 mmol) and the reaction mixture was stirred for 2 days at rt. $CH_2Cl_2$ (20 mL) was then added and the org. phase was washed with water (15 mL) followed by brine (15 mL). The org. phase was then dried over $MgSO_4$, filtered, and the solvents were removed under reduced pressure. Purification of the residue by FC (6:4 hept:EA) gave the title compound as a yellow oil. TLC: rf (6:4 hept-EA)=0.19. LC-MS-conditions 02: $t_R$=1.18 min, $[M+H]^+$=458.08.

Example 20

5-Phenyl-oxazole-4-carboxylic acid [2-(5-acetyl-furan-2-ylmethyl)-thiazol-4-yl]-amide In a flame dried round-bottomed flask equipped with a magnetic stir bar and under inert atmosphere ($N_2$), a solution of 5-phenyl-1,3-oxazole-4-carboxylic acid (41 mg, 0.21 mmol) in $CH_2Cl_2$ (2.0 mL) was treated sequentially with DMAP (6 mg, 0.05 mmol), HOBt (30 mg, 0.22 mmol), EDC.HCl (89 mg, 0.46 mmol) and DIPEA (0.13 mL, 0.74 mmol) and the resulting mixture was stirred at rt for 15 min. This solution was then added to a solution of 1-[5-(4-amino-thiazol-2-ylmethyl)-furan-2-yl]-ethanone hydrochloride (41 mg, 0.19 mmol) in dry $CH_2Cl_2$ (0.5 mL) and the reaction mixture was stirred for 16 h at rt. $CH_2Cl_2$ (20 mL) was then added and the org. phase was washed with water (15 mL) and brine (15 mL). The org. phase was then dried over $MgSO_4$, filtered, and the solvents were removed under reduced pressure. Purification of the residue by FC (1:1 hept:EA) gave the title compound as a brown foam. TLC: rf (1:1 hept-EA)=0.30. LC-MS-conditions 02: $t_R$=1.04 min, $[M+H]^+$=394.37.

Example 21

2-Methyl-5-m-tolyl-oxazole-4-carboxylic acid [2-(5-acetyl-furan-2-ylmethyl)-thiazol-4-yl]-amide In a flame dried round-bottomed flask equipped with a magnetic stir bar and under inert atmosphere ($N_2$), a solution of 2-methyl-5-m-tolyl-oxazole-4-carboxylic acid (50 mg, 0.23 mmol) in $CH_2Cl_2$ (2.3 mL) was treated sequentially with DMAP (7 mg, 0.06 mmol), HOBt (37 mg, 0.28 mmol), EDC.HCl (110 mg, 0.58 mmol) and DIPEA (0.16 mL, 0.92 mmol) and the resulting mixture was stirred at rt for 1 h. This solution was then treated with 1-[5-(4-amino-thiazol-2-ylmethyl)-furan-2-yl]-ethanone hydrochloride (51 mg, 0.23 mmol) and the reaction mixture was stirred for 16 h at rt. $CH_2Cl_2$ (20 mL) was then added and the org. phase was washed with water (15 mL) and brine (15 mL). The org. phase was then dried over $MgSO_4$, filtered, and the solvents were removed under reduced pressure. Purification of the residue by FC (1:1 hept:EA) gave the title compound as an orange oil. TLC: rf (1:1 hept-EA)=0.28. LC-MS-conditions 02: $t_R$=1.11 min, $[M+H]^+$=421.93.

II. Biological Assays
In Vitro Assay

The ALX receptor agonistic activity of the compounds of formula (I) is determined in accordance with the following experimental method.
Experimental Method:
Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1,000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% $CO_2$ in AB supplemented with 1 µM Fluo-4 (AM) (Invitrogen, F14202) and 20 mM HEPES (Gibco, 15630-056), the cells were washed and resuspended in AB. They were then seeded onto 384-well FLIPR assay plates (Greiner, 781091) at 50,000 cells in 70 µl per well and sedimented by centrifugation at 1,000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR Tetra instrument (Molecular Devices) was operated according to the manufacturer's standard instructions, adding 4 µl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition).

Agonistic activities ($EC_{50}$ values) of exemplified compounds are displayed in Table 1.

TABLE 1

| Compound | $EC_{50}$ [nM] |
|---|---|
| Example 1: [2-(5-Oxo-hexyl)-oxazol-4-yl]-carbamic acid 2-chloro-benzyl ester | 0.3 |
| Example 2: 5-Phenyl-oxazole-4-carboxylic acid [2-(5-oxo-hexyl)-oxazol-4-yl]-amide | 18 |
| Example 3: [2-(3-Acetyl-pyrazol-1-ylmethyl)-oxazol-4-yl]-carbamic acid 2-chloro-benzyl ester | 0.7 |
| Example 4: [2-(5,5-Difluoro-hexyl)-oxazol-4-yl]-carbamic acid 2-chloro-benzyl ester | 13 |
| Example 5: 2-Methyl-5-m-tolyl-oxazole-4-carboxylic acid [2-(5,5-difluoro-hexyl)-oxazol-4-yl]-amide | 194 |
| Example 6: 2-Methyl-5-m-tolyl-oxazole-4-carboxylic acid [2-(5-oxo-hexyl)-oxazol-4-yl]-amide | 9.8 |
| Example 7: 5-(3-Fluoro-phenyl)-thiazole-4-carboxylic acid [2-(5-oxo-hexyl)-oxazol-4-yl]-amide | 784 |
| Example 8: 5-(4-Fluoro-phenyl)-oxazole-4-carboxylic acid [2-(5-oxo-hexyl)-oxazol-4-yl]-amide | 86 |
| Example 9: 2-Ethyl-5-phenyl-oxazole-4-carboxylic acid [2-(5-oxo-hexyl)-oxazol-4-yl]-amide | 3.2 |
| Example 10: [2-(4-Bromo-pyrazol-1-ylmethyl)-oxazol-4-yl]-carbamic acid 2-chloro-benzyl ester | 72 |
| Example 11: [2-(3-Acetyl-pyrazol-1-ylmethyl)-oxazol-4-yl]-carbamic acid 2-chloro-4-fluoro-benzyl ester | 0.5 |
| Example 12: [2-(3-Acetyl-pyrazol-1-ylmethyl)-oxazol-4-yl]-carbamic acid 3-methoxy-benzyl ester | 1.0 |
| Example 13: [2-(3-Acetyl-pyrazol-1-ylmethyl)-oxazol-4-yl]-carbamic acid 4-trifluoromethyl-benzyl ester | 12 |
| Example 14: [2-(5-Acetyl-thiophen-2-ylmethyl)-oxazol-4-yl]-carbamic acid 2-chloro-benzyl ester | 2.2 |
| Example 15: [2-(3-Acetyl-benzyl)-oxazol-4-yl]-carbamic acid 3-trifluoromethoxy-benzyl ester | 48 |
| Example 16: 2-Cyclopropyl-5-phenyl-thiazole-4-carboxylic acid [2-(3-acetyl-pyrazol-1-ylmethyl)-oxazol-4-yl]-amide | 6560 |
| Example 17: (E)-N-[2-(3-Acetyl-benzyl)-oxazol-4-yl]-3-(4-trifluoromethyl-phenyl)-acrylamide | 1310 |
| Example 18: 5-Phenyl-oxazole-4-carboxylic acid [2-(5-acetyl-thiophen-2-ylmethyl)-thiazol-4-yl]-amide | 1570 |
| Example 19: 5-(3-Chloro-phenyl)-2-methyl-oxazole-4-carboxylic acid [2-(5-acetyl-thiophen-2-ylmethyl)-thiazol-4-yl]-amide | 3640 |
| Example 20: 5-Phenyl-oxazole-4-carboxylic acid [2-(5-acetyl-furan-2-ylmethyl)-thiazol-4-yl]-amide | 62 |
| Example 21: 2-Methyl-5-m-tolyl-oxazole-4-carboxylic acid [2-(5-acetyl-furan-2-ylmethyl)-thiazol-4-yl]-amide | 216 |

The invention claimed is:
1. A compound of formula (I),

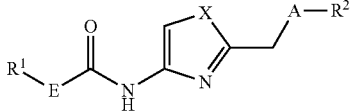

wherein
A represents a phenyl- or a heterocyclyl-group, wherein the two attachment-points of said groups are in a 1,3-arrangement; or A represents propan-1,3-diyl;
E represents *—($C_1$-$C_4$)alkyl-O—, —CH=CH— or

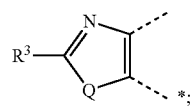

wherein the asterisk indicates the bond which is linked to $R^1$;
Q represents O or S;
$R^3$ represents hydrogen, ($C_1$-$C_4$)alkyl or cyclopropyl;
$R^1$ represents an aryl-group, which group is unsubstituted, mono- or di-substituted, wherein the substituents are independently selected from halogen, ($C_1$-$C_4$)alkyl, ($C_1$-$C_4$)alkoxy, ($C_1$-$C_4$)fluoroalkyl, ($C_1$-$C_4$)fluoroalkoxy or di-[($C_1$-$C_4$)alkyl]-amino;
$R^2$ represents halogen, —CO—($C_1$-$C_3$)alkyl, —CF$_2$—($C_1$-$C_3$)alkyl or —SO$_2$—($C_1$-$C_3$)alkyl; and
X represents O or S;
or a salt thereof.

2. The compound according to claim 1, wherein
A represents a thienyl- or a pyrazolyl-group, wherein the two attachment-points of said groups are in a 1,3-arrangement;
E represents *—CH$_2$—O— or

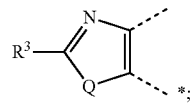

wherein the asterisks indicates the bond which is linked to $R^1$;
Q represents O or S;
$R^3$ represents hydrogen, methyl or ethyl;
$R^1$ represents phenyl, which is unsubstituted, mono- or di-substituted, wherein the substituents are independently selected from halogen, ($C_1$-$C_4$)alkyl, ($C_1$-$C_4$)alkoxy or ($C_1$-$C_4$)fluoroalkyl;
$R^2$ represents —CO—CH$_3$ or —CF$_2$—CH$_3$; and
X represents O;
or a salt thereof.

3. The compound according to claim 1, wherein
A represents a heterocyclyl-group, wherein the two attachment-points of said group are in a 1,3-arrangement;
or a salt thereof.

4. The compound according to claim 1, wherein E represents *—CH$_2$—O— or

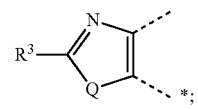

wherein the asterisk indicates the bond which is linked to $R^1$;
or a salt thereof.

5. The compound according to claim 1, wherein Q represents O;
or a salt thereof.

6. The compound according to claim 1, wherein $R^3$ represents hydrogen
or ($C_1$-$C_4$)alkyl;
or a salt thereof.

7. The compound according to claim 1, wherein
$R^1$ represents phenyl, which is unsubstituted, mono- or di-substituted, wherein the substituents are independently selected from halogen, ($C_1$-$C_4$)alkyl, ($C_1$-$C_4$)alkoxy or ($C_1$-$C_4$)fluoroalkyl;
or a salt thereof.

8. The compound according to claim 1, wherein $R^2$ represents —CO—($C_1$-$C_3$)alkyl or —CF$_2$—($C_1$-$C_3$)alkyl;
or a salt thereof.

9. The compound according to claim 1, wherein X represents O;
or a salt thereof.

10. The compound according to claim 1, selected from:
[2-(5-Oxo-hexyl)-oxazol-4-yl]-carbamic acid 2-chloro-benzyl ester;
5-Phenyl-oxazole-4-carboxylic acid [2-(5-oxo-hexyl)-oxazol-4-yl]-amide;
[2-(3-Acetyl-pyrazol-1-ylmethyl)-oxazol-4-yl]-carbamic acid 2-chloro-benzyl ester;
[2-(5,5-Difluoro-hexyl)-oxazol-4-yl]-carbamic acid 2-chloro-benzyl ester;
2-Methyl-5-m-tolyl-oxazole-4-carboxylic acid [2-(5,5-difluoro-hexyl)-oxazol-4-yl]-amide;
2-Methyl-5-m-tolyl-oxazole-4-carboxylic acid [2-(5-oxo-hexyl)-oxazol-4-yl]-amide;
5-(3-Fluoro-phenyl)-thiazole-4-carboxylic acid [2-(5-oxo-hexyl)-oxazol-4-yl]-amide;
5-(4-Fluoro-phenyl)-oxazole-4-carboxylic acid [2-(5-oxo-hexyl)-oxazol-4-yl]-amide;
2-Ethyl-5-phenyl-oxazole-4-carboxylic acid [2-(5-oxo-hexyl)-oxazol-4-yl]-amide;
[2-(4-Bromo-pyrazol-1-ylmethyl)-oxazol-4-yl]-carbamic acid 2-chloro-benzyl ester;
[2-(3-Acetyl-pyrazol-1-ylmethyl)-oxazol-4-yl]-carbamic acid 2-chloro-4-fluoro-benzyl ester;
[2-(3-Acetyl-pyrazol-1-ylmethyl)-oxazol-4-yl]-carbamic acid 3-methoxy-benzyl ester;
[2-(3-Acetyl-pyrazol-1-ylmethyl)-oxazol-4-yl]-carbamic acid 4-trifluoromethyl-benzyl ester;
[2-(5-Acetyl-thiophen-2-ylmethyl)-oxazol-4-yl]-carbamic acid 2-chloro-benzyl ester;
[2-(3-Acetyl-benzyl)-oxazol-4-yl]-carbamic acid 3-trifluoromethoxy-benzyl ester;
2-Cyclopropyl-5-phenyl-thiazole-4-carboxylic acid [2-(3-acetyl-pyrazol-1-ylmethyl)-oxazol-4-yl]-amide; or
(E)-N-[2-(3-Acetyl-benzyl)-oxazol-4-yl]-3-(4-trifluoromethyl-phenyl)-acrylamide;
or a salt thereof.

11. A pharmaceutical composition comprising a compound according to claim 1 or a pharmaceutically acceptable salt thereof, and at least one therapeutically inert excipient.

12. A method of treating a disease comprising administering to a subject in need thereof, a compound according to claim 1, or a pharmaceutically acceptable salt thereof, wherein the disease is selected from rheumatoid arthritis, acute lung injury, severe asthma, cystic fibrosis, inflammatory bowel disease, keratoconjunctivitis sicca or Alzheimer's disease.

13. A method of treating a disease comprising administering to a subject in need thereof, a composition according to claim 11, wherein the disease is selected from rheumatoid arthritis, acute lung injury, severe asthma, cystic fibrosis, inflammatory bowel disease, keratoconjunctivitis sicca or Alzheimer's disease.

* * * * *